(12) United States Patent
Tan et al.

(10) Patent No.: US 11,008,561 B2
(45) Date of Patent: May 18, 2021

(54) OPTIMIZED FACTOR IX GENE

(71) Applicant: BIOVERATIV THERAPEUTICS INC., Waltham, MA (US)

(72) Inventors: Siyuan Tan, Lexington, MA (US); Robert T. Peters, Needham, MA (US); Tongyao Liu, Lexington, MA (US)

(73) Assignee: BIOVERATIV THERAPEUTICS INC., Waltham, MA (US)

( * ) Notice: Subject to any disclaimer, the term of this patent is extended or adjusted under 35 U.S.C. 154(b) by 0 days.

(21) Appl. No.: 15/323,302

(22) PCT Filed: Jun. 30, 2015

(86) PCT No.: PCT/US2015/038678
§ 371 (c)(1),
(2) Date: Dec. 30, 2016

(87) PCT Pub. No.: WO2016/004113
PCT Pub. Date: Jan. 7, 2016

(65) Prior Publication Data
US 2017/0260516 A1 Sep. 14, 2017

Related U.S. Application Data

(60) Provisional application No. 62/168,565, filed on May 29, 2015, provisional application No. 62/019,069, filed on Jun. 30, 2014.

(51) Int. Cl.
| | | |
|---|---|---|
| *C07K 14/745* | (2006.01) | |
| *C07K 14/755* | (2006.01) | |
| *A61K 48/00* | (2006.01) | |
| *C12N 9/64* | (2006.01) | |

(52) U.S. Cl.
CPC ...... *C12N 9/644* (2013.01); *C12Y 304/21022* (2013.01); *C07K 2319/31* (2013.01); *C12N 2800/22* (2013.01)

(58) Field of Classification Search
None
See application file for complete search history.

(56) References Cited

U.S. PATENT DOCUMENTS

| | | |
|---|---|---|
| 4,683,195 A | 7/1987 | Mullis et al. |
| 4,683,202 A | 7/1987 | Mullis |
| 4,704,362 A | 11/1987 | Itakura et al. |
| 4,800,159 A | 1/1989 | Mullis et al. |
| 4,965,188 A | 10/1990 | Mullis et al. |
| 5,304,489 A | 4/1994 | Rosen |
| 5,648,260 A | 7/1997 | Winter et al. |
| 5,658,570 A | 8/1997 | Newman et al. |
| 5,712,122 A | 1/1998 | Boime et al. |
| 5,736,137 A | 4/1998 | Anderson et al. |
| 5,739,277 A | 4/1998 | Presta et al. |
| 5,741,957 A | 4/1998 | Deboer et al. |
| 5,834,250 A | 11/1998 | Wells et al. |
| 5,849,992 A | 12/1998 | Meade et al. |
| 5,869,046 A | 2/1999 | Presta et al. |
| 6,030,613 A | 2/2000 | Blumberg et al. |
| 6,086,875 A | 7/2000 | Blumberg et al. |
| 6,096,871 A | 8/2000 | Presta et al. |
| 6,121,022 A | 9/2000 | Presta et al. |
| 6,159,730 A | 12/2000 | Reff |
| 6,193,980 B1 | 2/2001 | Efstathiou et al. |
| 6,194,551 B1 | 2/2001 | Idusogie et al. |
| 6,242,195 B1 | 6/2001 | Idusogie et al. |
| 6,277,375 B1 | 8/2001 | Ward |
| 6,413,777 B1 | 7/2002 | Reff et al. |
| 6,485,726 B1 | 11/2002 | Blumberg et al. |
| 6,528,624 B1 | 3/2003 | Idusogie et al. |
| 6,531,298 B2 | 3/2003 | Stafford et al. |
| 6,538,124 B1 | 3/2003 | Idusogie et al. |
| 6,696,245 B2 | 2/2004 | Winter et al. |
| 6,737,056 B1 | 5/2004 | Presta |
| 6,808,905 B2 | 10/2004 | McArthur et al. |
| 6,821,505 B2 | 11/2004 | Ward |
| 6,998,253 B1 | 2/2006 | Presta et al. |
| 7,083,784 B2 | 8/2006 | Dall'Acqua et al. |
| 7,179,903 B2 | 2/2007 | McArthur et al. |
| 7,317,091 B2 | 1/2008 | Lazar et al. |
| 7,404,956 B2 | 7/2008 | Peters et al. |
| 7,745,179 B2 | 6/2010 | McArthur et al. |

(Continued)

FOREIGN PATENT DOCUMENTS

| | | |
|---|---|---|
| EP | 1395293 A1 | 3/2004 |
| EP | 2881463 | * 12/2013 |

(Continued)

OTHER PUBLICATIONS

Biochemistry, John Wiley and Sons, 1990, p. 126-129.*
Kimchi-Sarfaty Cet al., A "silent" polymorphism in the MDR1 gene changes substrate specificity.Science. Jan. 26, 2007;315(5811): 525-8.*
Cantore et al Hyperfunctional coagulation factor IX improves the efficacy of gene therapy in hemophilic mice Blood, Nov. 29, 2012 vol. 120, No. 23 pp. 4517-4520.*
Altschul, S.F., et al., "Basic Local Alignment Search Tool," Journal of Molecular Biology 215(3):403-410, Elsevier, England (Oct. 1990).
Andersson, L.O., et al., "Purification and Characterization of Human Factor IX," Thrombosis Research 7(3):451-459, Pergamon Press, Inc., United States (Sep. 1975).

(Continued)

*Primary Examiner* — Maria G Leavitt
(74) *Attorney, Agent, or Firm* — Lathrop GPM LLP; James V. DeGiulio, Esq.; James H. Velema, Esq.

(57) ABSTRACT

The present invention provides codon optimized Factor IX sequences, vectors and host cells comprising codon optimized Factor IX sequences, polypeptides encoded by codon optimized Factor IX sequences, and methods of producing such polypeptides. The present invention also provides methods of treating bleeding disorders such as hemophilia comprising administering to the subject a codon optimized Factor IX nucleic acid sequence or the polypeptide encoded thereby.

22 Claims, 11 Drawing Sheets
Specification includes a Sequence Listing.

(56) References Cited

U.S. PATENT DOCUMENTS

| | | | |
|---|---|---|---|
| 8,734,809 B2 | 5/2014 | Gao et al. | |
| 9,061,059 B2* | 6/2015 | Chakraborty | A61K 48/005 |
| 10,000,748 B2* | 6/2018 | Schuttrumpf | C12N 9/644 |
| 10,058,624 B2* | 8/2018 | Doering | A61K 48/0058 |
| 10,125,357 B2* | 11/2018 | Seifried | C12Y 304/21022 |
| 2003/0069395 A1 | 4/2003 | Sato et al. | |
| 2003/0235536 A1 | 12/2003 | Blumberg et al. | |
| 2007/0231329 A1 | 10/2007 | Lazar et al. | |
| 2007/0237765 A1 | 10/2007 | Lazar et al. | |
| 2007/0237766 A1 | 10/2007 | Lazar et al. | |
| 2007/0237767 A1 | 10/2007 | Lazar et al. | |
| 2007/0243188 A1 | 10/2007 | Lazar et al. | |
| 2007/0248603 A1 | 10/2007 | Lazar et al. | |
| 2007/0286859 A1 | 12/2007 | Lazar et al. | |
| 2008/0004206 A1 | 1/2008 | Rosen et al. | |
| 2008/0057056 A1 | 3/2008 | Lazar et al. | |
| 2008/0076174 A1 | 3/2008 | Selden et al. | |
| 2008/0153156 A1* | 6/2008 | Gray | A61K 48/0066 435/320.1 |
| 2008/0153751 A1 | 6/2008 | Rosen et al. | |
| 2008/0161243 A1 | 7/2008 | Rosen et al. | |
| 2008/0194481 A1 | 8/2008 | Rosen et al. | |
| 2008/0260738 A1 | 10/2008 | Moore et al. | |
| 2008/0261877 A1 | 10/2008 | Ballance et al. | |
| 2009/0087411 A1 | 4/2009 | Fares et al. | |
| 2010/0239554 A1 | 9/2010 | Schellenberger et al. | |
| 2010/0284971 A1 | 11/2010 | Samulski | |
| 2010/0292130 A1 | 11/2010 | Skerra et al. | |
| 2010/0323956 A1 | 12/2010 | Schellenberger et al. | |
| 2011/0046060 A1 | 2/2011 | Schellenberger et al. | |
| 2011/0046061 A1 | 2/2011 | Schellenberger et al. | |
| 2011/0077199 A1 | 3/2011 | Schellenberger et al. | |
| 2011/0172146 A1 | 7/2011 | Schellenberger et al. | |
| 2011/0244550 A1 | 10/2011 | Simioni | |
| 2012/0178691 A1 | 7/2012 | Schellenberger et al. | |
| 2013/0052191 A1 | 2/2013 | Blein et al. | |
| 2013/0195801 A1 | 8/2013 | Gao et al. | |
| 2014/0010861 A1 | 1/2014 | Bancel et al. | |
| 2016/0304851 A1* | 10/2016 | Schuttrumpf | C12N 9/644 |
| 2017/0326256 A1* | 11/2017 | Doering | A61K 48/0058 |

FOREIGN PATENT DOCUMENTS

| | | |
|---|---|---|
| RU | 2500816 C1 | 12/2013 |
| WO | WO-8807089 A1 | 9/1988 |
| WO | WO-9614339 A1 | 5/1996 |
| WO | WO-9712622 A1 | 4/1997 |
| WO | WO-9805787 A1 | 2/1998 |
| WO | WO-9809657 A2 | 3/1998 |
| WO | WO-9817815 A1 | 4/1998 |
| WO | WO-9817816 A1 | 4/1998 |
| WO | WO-9818934 A1 | 5/1998 |
| WO | WO-9823289 A1 | 6/1998 |
| WO | WO-9931251 A1 | 6/1999 |
| WO | WO-9951642 A1 | 10/1999 |
| WO | WO-9958572 A1 | 11/1999 |
| WO | WO-0009560 A2 | 2/2000 |
| WO | WO-0020561 A1 | 4/2000 |
| WO | WO-0032767 A1 | 6/2000 |
| WO | WO-0042072 A2 | 7/2000 |
| WO | WO-0240544 A2 | 5/2002 |
| WO | WO-0244215 A2 | 6/2002 |
| WO | WO-02060919 A2 | 8/2002 |
| WO | WO-02092134 A1 | 11/2002 |
| WO | WO-03020764 A2 | 3/2003 |
| WO | WO-03042361 A2 | 5/2003 |
| WO | WO-03052051 A2 | 6/2003 |
| WO | WO-03057780 A1 | 7/2003 |
| WO | WO-03074569 A2 | 9/2003 |
| WO | WO-03077834 A2 | 9/2003 |
| WO | WO-2004016750 A2 | 2/2004 |
| WO | WO-2004029207 A2 | 4/2004 |
| WO | WO-2004035752 A2 | 4/2004 |
| WO | WO-2004044859 A1 | 5/2004 |
| WO | WO-2004063351 A2 | 7/2004 |
| WO | WO-2004074455 A2 | 9/2004 |
| WO | WO-2004094642 A2 | 11/2004 |
| WO | WO-2004099249 A2 | 11/2004 |
| WO | WO-2005040217 A2 | 5/2005 |
| WO | WO-2005070963 A1 | 8/2005 |
| WO | WO-2005077981 A2 | 8/2005 |
| WO | WO-2005092925 A2 | 10/2005 |
| WO | WO-2005123780 A2 | 12/2005 |
| WO | WO-2006019447 A1 | 2/2006 |
| WO | WO-2006047350 A2 | 5/2006 |
| WO | WO-2006085967 A2 | 8/2006 |
| WO | WO-2007000668 A2 | 1/2007 |
| WO | WO-2007004670 A1 | 1/2007 |
| WO | WO-2007021494 A2 | 2/2007 |
| WO | WO-2007148971 A2 | 12/2007 |
| WO | WO-2007149406 A2 | 12/2007 |
| WO | WO-2007149852 A2 | 12/2007 |
| WO | WO-2008012543 A1 | 1/2008 |
| WO | WO-2008033413 A2 | 3/2008 |
| WO | WO-2008118507 A2 | 10/2008 |
| WO | WO-2008143954 A2 | 11/2008 |
| WO | WO-2008155134 A1 | 12/2008 |
| WO | WO-2009051717 A2 | 4/2009 |
| WO | WO-2009058322 A1 | 5/2009 |
| WO | WO-2009130198 A2 | 10/2009 |
| WO | WO-2009137254 A2 | 11/2009 |
| WO | WO-2009140015 A2 | 11/2009 |
| WO | WO-2010029178 A1 | 3/2010 |
| WO | WO-2010055413 A1 | 5/2010 |
| WO | WO-2010091122 A1 | 8/2010 |
| WO | WO-2010125471 A2 | 11/2010 |
| WO | WO-2010140148 A1 | 12/2010 |
| WO | WO-2010144502 A2 | 12/2010 |
| WO | WO-2010144508 A1 | 12/2010 |
| WO | WO-2011028228 A1 | 3/2011 |
| WO | WO-2011028229 A1 | 3/2011 |
| WO | WO-2011028344 A2 | 3/2011 |
| WO | WO-2012006624 A2 | 1/2012 |
| WO | WO-2012006635 A1 | 1/2012 |
| WO | WO-2013122617 A1 | 8/2013 |
| WO | WO2016168728 * | 10/2016 |
| WO | WO 2016168728 * | 10/2016 |
| WO | WO-2016168728 A1 | 10/2016 |

OTHER PUBLICATIONS

Armour, K.L., et al., "Recombinant Human IgG Molecules Lacking Fcgamma Receptor I Binding and Monocyte Triggering Activities," European Journal of Immunology 29(8):2613-2624, Wiley-VCH, Germany (Aug. 1999).

Baldassarre, H., et al., "Production of Transgenic Goats by Pronuclear Microinjection of In Vitro Produced Zygotes Derived From Oocytes Recovered by Laparoscopy," Theriogenology 59(3-4):831-839, Elsevier, United States (Feb. 2003).

Benhar, I. and Pastan, I., "Cloning, Expression and Characterization of the Fv Fragments of the Anti-carbohydrate mAbs B1 and B5 as Single-chain Immunotoxins," Protein Engineering Design and Selection 7(11):1509-1515, Oxford University Press, England (Dec. 1994).

Brinster, R.L., et al., "Expression of a Microinjected Immunoglobulin Gene in the Spleen of Transgenic Mice," Nature 306(5941):332-336, Nature Publishing Group, England (Nov. 1983).

Brinster, R.L., et al., "Factors Affecting the Efficiency of Introducing Foreign DNA into Mice by Microinjecting Eggs," Proceedings of the National Academy of Sciences USA 82(13):4438-4442, National Academy of Sciences, United States (Jul. 1985).

Brown, B.D., et al., "Endogenous MicroRNA Regulation Suppresses Transgene Expression in Hematopoietic Lineages and Enables Stable Gene Transfer," Nature Medicine 12(5):585-591, Nature Publishing Company, United States (May 2006).

Burgess-Brown, N.A., et al., "Codon Optimization can Improve Expression of Human Genes in Escherichia coli: a Multi-gene Study," Protein Expression and Purification 59(1):94-102, Academic Press, United States (May 2008).

(56) References Cited

OTHER PUBLICATIONS

Burmeister, W.P., et al., "Crystal Structure of the Complex of Rat Neonatal Fc Receptor with Fc," Nature 372(6504):379-383, Nature Publishing Group, England (Nov. 1994).
Capon, D.J., et al., "Designing CD4 Immunoadhesins for AIDS Therapy," Nature 337(6207):525-531, Nature Publishing Group, England (Feb. 1989).
Chabner, B.A., et al., "Antineoplastic Agents," in Goodman & Gilman's The Pharmacological Basis of Therapeutics, 9th ed., Hardman, G.H., et al., eds.,pp. 1233-1287, McGraw-Hill, United States (1996).
Liu, T., et al., "Codon optimization improves factor IX expression in Hemophilia B mice by more than 15-fold," Human Gene Therapy 26(10): Abstract P004 (Oct. 2015).
Chiorini, J.A., et al., "Cloning and Characterization of Adeno-associated Virus Type 5," Journal of Virology 73(2):1309-1319, American Society for Microbiology, United States (1999).
Chiorini, J.A., et al., "Cloning of Adeno-associated Virus Type 4 (AAV4) and Generation of Recombinant AAV4 Particles," Journal of Virology 71(9):6823-6833, American Society for Microbiology, United States (1997).
"Codon Usage Database" accessed at http://www.kazusa.or.jp/codon/ on Apr. 23, 2013, 1 page.
Costa, R.H., et al., "Transcriptional Control of the Mouse Prealbumin (Transthyretin) Gene: Both Promoter Sequences and a Distinct Enhancer Are Cell Specific," Molecular and Cellular Biology 6(12):4697-4708, American Society for Microbiology, United States (Dec. 1986).
Dalkara, D., et al., "In Vivo-directed Evolution of a New Adeno-associated Virus for Therapeutic Outer Retinal Gene Delivery From the Vitreous," Science Translational Medicine 5(189):189ra76, American Association for the Advancement of Science, United States (Jun. 12, 2013).
Dennis, M.S., et al., "Albumin Binding as a General Strategy for Improving the Pharmacokinetics of Proteins," The Journal of Biological Chemistry 277(38):35035-35043, American Society for Biochemistry and Molecular Biology, United States (Sep. 2002).
Ellman, J., et al., "Biosynthetic Method for Introducing Unnatural Amino Acids Site-Specifically into Proteins," Methods in Enzymology 202:301-336, Elsevier, United States (1991).
Friend, P.J., et al., "Phase I Study of an Engineered Aglycosylated Humanized CD3 Antibody in Renal Transplant Rejection," Transplantation 68(11):1632-1637, Lippincott Williams & Wilkins, Inc., United States (Dec. 1999).
Gaspar, P., et al., "Eugene: Maximizing Synthetic Gene Design for Heterologous Expression," Bioinformatics 28(20):2683-2684, Oxford University Press, England (Oct. 2012).
GenBank, "*Homo sapiens* Transferrin (TF), mRNA," Accession No. NM001063.3 published on May 25, 2014, accessed at http://www.ncbi.nlm.nih.gov/nuccore/NM_001063, accessed on Sep. 24, 2014, 5 pages.
GenBank, "*Homo sapiens* Transferrin (TF), mRNA," Accession No. XM002793 published on May 13, 2002, accessed at https://www.ncbi.nlm.nih.gov/nuccore/XM_002793.7?report=genbank, accessed on Sep. 24, 2014, 2 pages.
GenBank, "*Homo sapiens* Transferrin (TF), mRNA," Accession No. XM039847 published on Jul. 16, 2001, accessed at http://www.ncbi.nlm.nih.gov/nuccore/XM_039847.1?report=genbank, accessed on Sep. 24, 2014, 2 pages.
GenBank, "*Homo sapiens* Transferrin (TF), mRNA," Accession No. XM039845 published Jul. 16, 2001, accessed at https://www.ncbi.nlm.nih.gov/nuccore/XM_039845.1?report=genbank, accessed on Sep. 24, 2014, 2 pages.
GenBank, "Human Transferrin mRNA, Complete cds," Accession No. M12530.1, published on Jan. 14, 1995, accessed at http://www.ncbi.nlm.nih.gov/nuccore/M1253014, accessed on Jan. 15, 2015, 2 pages.
GenBank, "Transferrin [human, liver, mRNA, 2347 nt]," Accession No. S95936.1, published on May 7, 1993, accessed at http://www.ncbi.nlm.nih.gov/nuccore/S95936, accessed on Sep. 24, 2014, 2 pages.
Genbank, "transferrin precursor [*Homo sapiens*]" Accession AAA61140.1, accessed at http://www.ncbi.nlm.nih.gov/protein/AAA61140, accessed on Mar. 29, 2016, 3 pages.
Genbank, "Synthetic Construct Hepatocyte-restricted Expression Cassette," accessed at https://www.ncbi.nlm.nih.gov/nuccore/AY661265, accessed on Sep. 29, 2009.
Genbank,"Adeno-associated Virus 2, Complete Genome," Accession AF043303.1, accessed at http://www.ncbi.nlm.nih.gov/nuccore/AF043303.
Genbank,"Adeno-associated Virus 2, Complete Genome," Accession J01901.1, accsessed at http://www.ncbi.nlm.nih.gov/nuccore/J01901.
Genbank,"Adeno-associated Virus 4, Complete Genome," Accession U89790.1, accessed at http://www.ncbi.nlm.nih.gov/nuccore/U89790.
Genbank,"Adeno-associated virus 5 DNA Binding trs Helicase (Rep22) and capsid protein (VP1) genes, complete cds," Accession AF085716.1, accessed at http://www.ncbi.nlm.nih.gov/nuccore/AF085716.
Giangrande, P., "Haemophilia B: Christmas Disease," Expert Opinion on Pharmacotherapy 6(9):1517-1524, Ashley Publications Ltd., England (Aug. 2005).
Nair, N., et al, "Computationally designed liver-specific transcriptional modules and hyperactive factor IX improve hepatic gene therapy," Blood 123(20): 3195-3199, American Society of Hematology, United States (2014).
Suwanmanee, T., et al, "Integration-deficient Lentiviral Vectors Expressing Codon-optimized R338L Human FIX Restore Normal Hemostasis in Hemophilia B Mice," Molecular Therapy 22(3): 567-574, Elsevier, Netherlands (2014).
Ho, S.N., et al., "Site-directed Mutagenesis by Overlap Extension using the Polymerase Chain Reaction," Gene 77(1):51-59, Elsevier Science Publishers B.V., Netherlands (Apr. 1989).
Holt, L.J., et al., "Anti-Serum Albumin Domain Antibodies for Extending the Half-lives of Short Lived Drugs," Protein Engineering, Design and Selection 21(5):283-288, Oxford University Press, England (May 2008).
Horton, R.M., et al., "Gene Splicing by Overlap Extension," Methods in Enzymology 217:270-279, Academic Press, United States (1993).
Ill, C.R., et al., "Optimization of the Human Factor VIII Complementary DNA Expression Plasmid for Gene Therapy of Hemophilia A," Blood Coagulation & Fibrinolysis 8(2):S23-S30, Lippincott Williams and Wilkins, England (Dec. 1997).
International Search Report and Written Opinion of the International Searching Authority for International Application No. PCT/US2015/038678, ISA/US, Alexandria, Virginia, dated Dec. 8, 2015, 12 pages.
Israel, E.J., et al., "Expression of the Neonatal Fc Receptor, FcRn, on Human Intestinal Epithelial Cells," Immunology 92(1):69-74, Blackwell Sciences, England (Sep. 1997).
Kobayashi, N., et al., "FcRn-Mediated Transcytosis of Immunoglobulin G in Human Renal Proximal Tubular Epithelial Cells," American Journal of Physiology 282(2):F358-F365, American Physiological Society, United States (Feb. 2002).
Konig, T. and Skerra, A., "Use of an Albumin-binding Domain for the Selective Immobilisation of Recombinant Capture Antibody Fragments on ELISA Plates," Journal of Immunological Methods 218(1-2):73-83, Elsevier Science B.V., Netherlands (Sep. 1998).
Kotterman, M.A. and Schaffer, D.V., "Engineering Adeno-associated Viruses for Clinical Gene Therapy," Nature Reviews. Genetics 15(7):445-451, Nature Pub. Group, England (Jul. 2014).
Kraulis, P.J., et al., "The Serum Albumin-binding Domain of Streptococcal Protein G is a Three-helical Bundle: A Heteronuclear NMR Study," FEBS Letters 378(2):190-194, Elsevier Science B.V, Netherlands (Jan. 1996).
Kudla, G., et al., "High Guanine and Cytosine Content Increases mRNA Levels in Mammalian Cells," PLoS Biology 4(6):e180, Public Library of Science, United States (Jun. 2006).

(56) References Cited

OTHER PUBLICATIONS

Larrick, J.W., et al., "Rapid Cloning of Rearranged Immunoglobulin Genes from Human Hybridoma Cells using Mixed Primers and the Polymerase Chain Reaction," Biochemical and Biophysical Research Communications 160(3):1250-1256, Academic Press, United States (May 1989).

Linhult, M., et al., "Mutational Analysis of the Interaction Between Albumin-Binding Domain from Streptococcal Protein G and Human Serum Albumin," Protein Science 11(2):206-213, Cold Spring Harbor Laboratory Press, United States (Feb. 2002).

Malassagne, B., et al., "Hypodermin A, A New Inhibitor of Human Complement for the Prevention of Xenogeneic Hyperacute Rejection," Xenotransplantation 10(3):267-277, John Wiley & Sons, United States (May 2003).

McKnight, G.S., et al., "Expression of the Chicken Transferrin Gene in Transgenic Mice," Cell 34(2):335-341, Cell Press, United States (Sep. 1983).

Mount, J.D., et al., "Sustained Phenotypic Correction of Hemophilia B dogs with a Factor IX Null Mutation by Liver-directed Gene Therapy," Blood 99(8):2670-2676, The American Society of Hematology, United States (Apr. 2002).

Muller, D. and Kontermann, R.E., "Recombinant Bispecific Antibodies for Cellular Cancer Immunotherapy," Current Opinion in Molecular Therapeutics 9(4):319-326, The Thomson Corporation, United States (Aug. 2007).

Database Geneseq, Human codon-optimized clotting factor IX (hFIX) gene, SEQ ID No. 2, BBB41169, Dec. 10, 2013.

Nakamura, Y., et al., "Codon Usage Tabulated from International DNA Sequence Databases: Status for the Year 2000," Nucleic Acids Research 28(1):292, Oxford University Press, United Kingdom (Jan. 2000).

Narita, M., et al., "The Low-density Lipoprotein Receptor-related Protein (LRP) Mediates Clearance of Coagulation Factor Xa In Vivo," Blood 91(2):555-560, The American Society of Hematology, United States (Jan. 1998).

Neumann, E., et al., "Gene Transfer into Mouse Lyoma Cells by Electroporation in High Electric Fields," The EMBO Journal 1(7):841-845, IRL Press Limited, England (Feb. 1982).

Noren, C.J., et al., "A General Method for Site-specific Incorporation of Unnatural Amino Acids into Proteins," Science 244(4901):182-188, Association for the Advancement of Science, United States (Apr. 1989).

Remington's Pharmaceutical Sciences (Mack Pub. Co., Easton, Pa. 1980).

Ridgway, A. A. G., et al., "Introduction of Vector into Host Cells," in Mammalian Expression Vectors, Chapter 24.2, Rodriguez and Denhardt, Eds.,pp. 470-472, Butterworths, Boston, Mass. (1988).

Ritchie, K.A., et al., "Allelic Exclusion and Control of Endogenous Immunoglobulin Gene Rearrangement in Kappa Transgenic Mice," Nature 312(5994):517-520, Nature Publishing Group, England (Dec. 1984).

Robl, J.M., et al., "Artificial Chromosome Vectors and Expression of Complex Proteins in Transgenic Animals," Theriogenology 59(1):107-113, Elsevier, United States (Jan. 2003).

Roovers, R.C., et al., "Efficient Inhibition of EGFR Signaling and of Tumour Growth by Antagonistic Anti-EGFR Nanobodies," Cancer Immunology, Immunotherapy 56(3):303-317, Springer Verlag, Germany (Mar. 2007).

Rouet, P., et al., "A Potent Enhancer Made of Clustered Liver-specific Elements in the Transcription Control Sequences of Human Alpha 1-microglobulin/bikunin Gene," The Journal of Biological Chemistry 267(29):20765-20773, American Society for Biochemistry and Molecular Biology, United States (Oct. 1992).

Rouet, P., et al., "An Array of Binding Sites for Hepatocyte Nuclear Factor 4 of High and Low Affinities Modulates the Liver-specific Enhancer for the Human alpha1-microglobulin/bikunin Precursor," The Biochemical Journal 334(3):577-584, Portland Press, England (Sep. 1998).

Rouet, P., et al., "Hierarchy and Positive/negative Interplays of the Hepatocyte Nuclear Factors HNF-1, -3 and -4 in the Liver-specific Enhancer for the Human Alpha-1-microglobulin/bikunin Precursor," Nucleic Acids Research 23(3):395-404, Oxford University Press, England (Feb. 1995).

Routledge, E.G., et al., "The Effect of Aglycosylation on the Immunogenicity of a Humanized Therapeutic CD3 Monoclonal Antibody," Transplantation 60(8):847-853, Lippincott Williams & Wilkins, United States (Oct. 1995).

Ruberti, F., et al., "The Use of the RACE Method to Clone Hybridoma cDNA when V Region Primers Fail," Journal of Immunological Methods 173(1):33-39, Elsevier, United States (Jul. 1994).

Ruther, U. and Muller-Hill, B., "Easy Identification of cDNA Clones," The EMBO Journal 2(10):1791-1794, IRL Press Ltd, England (1983).

Rutledge, E.A., et al., "Infectious Clones and Vectors Derived From Adeno-associated Virus (AAV) Serotypes Other than AAV Type 2," Journal of Virology 72(1):309-319, American Society for Microbiology, United States (1998).

Sambrook, J., et al., "Molecular Cloning: A Laboratory Manual," Second Edition, Cold Spring Harbor Laboratory Press, United States (1989).

Sharp, P.M. and Li, W.H., "The Codon Adaptation Index—A Measure of Directional Synonymous Codon Usage Bias, and Its Potential Applications," Nucleic Acids Research 15(3):1281-1295, Oxford University Press, England (Feb. 1987).

Shields, R.L., et al., "High Resolution Mapping of the Binding Site on Human IgG1 for Fc gamma RI, Fc gamma RII, Fc gamma RIII, and FcRn and Design of IgG1 Variants with Improved Binding to the Fc gamma R," The Journal of Biological Chemistry 276(9):6591-6604, American Society for Biochemistry and Molecular Biology, United States (Mar. 2001).

Srivastava, A., et al., "Nucleotide Sequence and Organization of the Adeno-associated Virus 2 Genome," Journal of Virology 45(2):555-564, American Society for Microbiology, United States (1983).

Story, C.M., et al., "A Major Histocompatibility Complex Class I-like Fc Receptor Cloned from Human Placenta: Possible Role in Transfer of Immunoglobulin G from Mother to Fetus," The Journal of Experimental Medicine 180(6):2377-2381, The Rockefeller University Press, United States (Dec. 1994).

Torres-Torronteras, J., et al., "Gene Therapy Using a Liver-targeted AAV Vector Restores Nucleoside and Nucleotide Homeostasis in a Murine Model of MNGIE," Molecular Therapy 22(5):901-907, Cell Press, United States (May 2014).

Trussel, S., et al., "New Strategy for the Extension of the Serum Half-life of Antibody Fragments," Bioconjugate Chemistry 20(12):2286-2292, American Chemical Society, United States (Dec. 2009).

Vigna, E., et al., "Efficient Tet-dependent Expression of Human Factor IX in vivo by a New Self-regulating Lentiviral Vector," Molecular Therapy 11(5):763-775, Cell Press, United States (May 2005).

Wagner, T.E., et al., "Microinjection of a Rabbit beta-globin Gene into Zygotes and Its Subsequent Expression in Adult Mice and their Offspring," Proceedings of the National Academy of Sciences USA 78(10):6376-6380, National Academy of Sciences, United States (Oct. 1981).

Ward, E.S. and Ghetie, V., "The Effector Functions of Immunoglobulins: Implications for Therapy," Therapeutic Immunology 2(2):77-94, Blackwell Science Ltd., England (Apr. 1995).

Wigler, M., et al., "Biochemical Transfer of Single-copy Eucaryotic Genes using Total Cellular DNA as Donor," Cell 14(3):725-731, Cell Press, United States (Jul. 1978).

Wu, P., et al., "Mutational Analysis of the Adeno-associated Virus Type 2 (AAV2) Capsid Gene and Construction of AAV2 Vectors with Altered Tropism," Journal of Virology 74(18):8635-8647, American Society for Microbiology, United States (2000).

Cantore, A., et al., "Hyperfunctional coagulation factor IX improves the efficacy of gene therapy in hemophilic mice," Blood 120(23): 4517-4521, American Society of Hematology, United States (2012).

Partial European Search Report received for European Patent Application No. 15814881.7, dated Jan. 12, 2018, 6 pages.

Supplementary European Search Report received for European Patent Application No. 15814881.7, dated Apr. 13, 2015, 7 pages.

(56) References Cited

OTHER PUBLICATIONS

Third party observations against European Application No. 15814881.7, dated Oct. 2, 2020, 107 pages.

* cited by examiner

Optimized Human Factor IX Sequence (SEQ ID NO:1)

ATGCAGAGAGTCAACATGATTATGGCTGAGTCACCTGGGCTGATTACTATTTGCCTGCTG
GGCTACCTGCTGTCCGCCGAGTGTACCGTGTTCCTGGACCATGAGAACGCAAATAAGATC
CTGAACAGGCCCAAAAGATACAATAGTGGGAAGCTGGAAGAATTTGTCCAGGGCAACCTG
GAGAGAGAATGCATGGAAGAAAAGTGTAGCTTCGAGGAAGCCCGCGAGGTGTTTGAAAAT
ACAGAGCGAACCACAGAGTTCTGGAAGCAGTATGTGGACGGCGATCAGTGCGAGAGCAAC
CCCTGTCTGAATGGCGGAAGTTGCAAAGACGATATCAACTCATACGAATGCTGGTGTCCT
TTCGGGTTTGAAGGCAAAAATTGCGAGCTGGACGTGACATGTAACATTAAGAATGGACGG
TGCGAGCAGTTTTGTAAAAACTCTGCCGATAATAAGGTGGTGTGCAGCTGTACTGAAGGA
TATCGCCTGGCTGAGAACCAGAAGTCCTGCGAACCAGCAGTGCCCTTCCCTTGTGGGAGG
GTGAGCGTCTCCCAGACTTCAAAAACTGACCAGAGCAGAGACAACATTACTCAGTCTACCCAGAGT
TACGTCAACAGCACTGAGGCCGAAACCATCCTGGACAACATCACTCAGTCTACCCAGAGT
TTCAATGACTTTACTCGGGTCGTCGGTGGAAGGTGGATGCATTTTGCGGAGGGTCTATCGTGAATGAGAAA
CAGGTGGTCCTGAACGGGAAAGGTGGATGCATTTTGCGGAGGGTCTATCGTGAATGAGAAA
TGGATTGTCACCGCCGCTCACTGCGTGTGAAACCGGAGTCAAGATCACAGTCGGTCCGCTGGG
GAGCACAACATTGAGGAAACAGAACATACTGAGCAGAAGCGGAATGTGATCCGCATCATT
CCTCACCATAACTACAATGCAGCCATCAACATTACAATCATGACATTGCCCTGCTGGAA
CTGGATGAGCCCTCTGGTCTGAACAGCTGCGAACAGCTACGTCACTGCCATTCTGACAAAGAG
TATACCAATATCTTCCTGAAGTTTGGATCAGGGTACCGTCAGGGGCCCTCGGTCGATCGAGCT
CACAAGGGCAGGAGCGCCTGGTGCTCCAGTATCGTGCGAGTGCCCTCGGTCGATCGAGCT
ACCTGTCTGAGGTCTCCAAGTTTACAATCTACAACAACATGTTCTGCGCTGGGTTTCAC
GAGGGAGGACGAGACTCCGTGTCAGGGCGATTCTCAGGGCGAATGTGACAGAGGTCGAA
GGCACCAGCTTCCTGACTGGCATCATTCCTGGGGAGAGGAATGTGCAATGAAGGGAAAA
TACGGGATCTACACCAAAGTGAGCCGCTATGTGAACTGGATCAAGGAAAAAAACCAAACTG
ACCTAATGA

FIG. 1

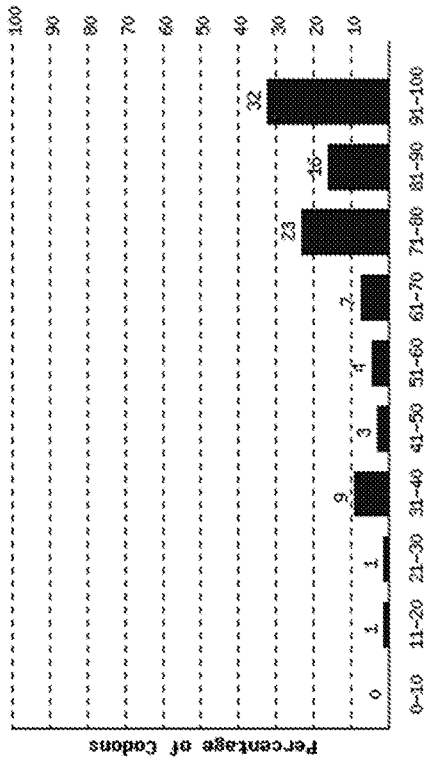
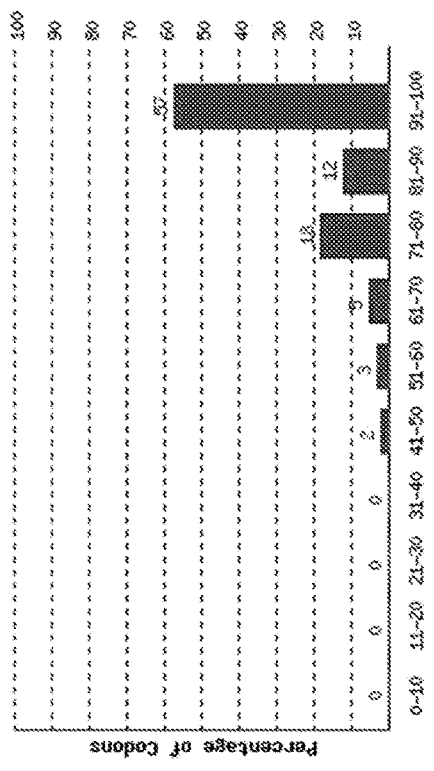
FIG. 3

A.
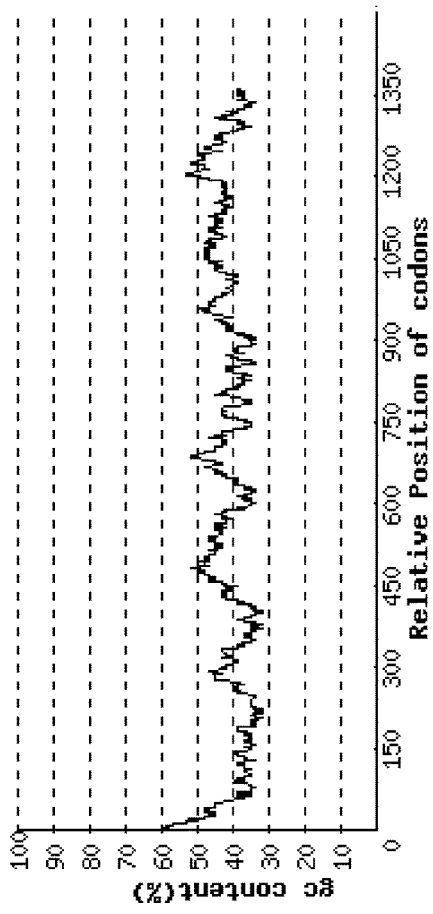
B.
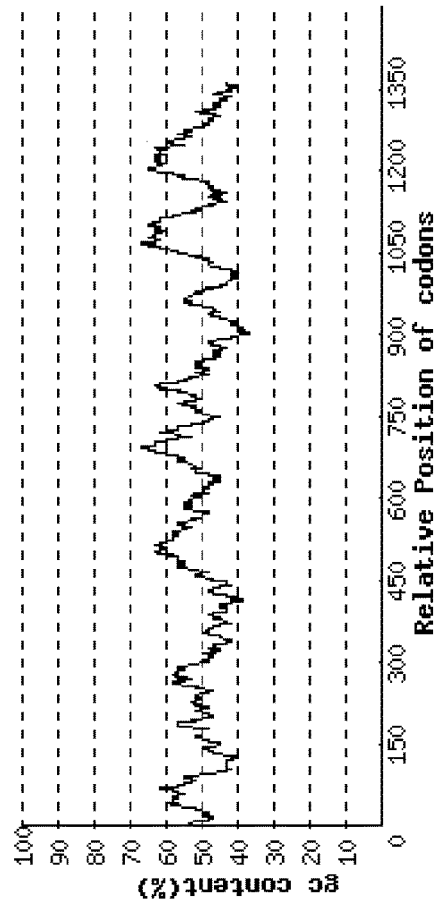
FIG. 4

Alignment of Optimized and Original Human Factor IX Sequences (SEQ ID NO:1 and SEQ ID NO:2)

```
Optimized   16  ATGCAGAGAGTCAACATGATTATGGCTGAGTCACCTGGGCTGATTACTATTTGCCTGCCTG
Original    16  ATGCAGCGCGTGAACATGATCATGGCAGAATCACCAGGCCTCATCACCATCTGCCTTTTA Optimized   76  GGCTACCTGCTGTCCGCCGAGTGTACCGTGTTCCTGGACCATGAGAACGCAAATAAGATC
Original    76  GGATATCTACTCAGTGCTGAATGTACAGTTTTTCTTGATCATGAAAACGCCAACAAATT Optimized  136  CTGAACAGGCCCAAAAGATACAATAGTGGGAAGCTGGAGGAATTTGTGCAGGGCAACCTG
Original   136  CTGAATCGGCCCAAAGAGAGGTATAATTCAGGTAAATTGGAAGAGTTTGTTCAAGGGAATCTA Optimized  196  GAGAGAGAATGCATGGAGGAAAAGTGTAGCTTCGAGGAAGCCCGCGAGGTGTTTGAAAAT
Original   196  GAGAGAGAATGTATGGAAGAAAAGTGTAGTTTTGAAGAAGCACGAGAAGTTTTTGAAAAC Optimized  256  ACAGAGCGAACCACAGAGTTCTGGAAGCAGTATGTGGACGGCGATCAGTGCGAGAGCAAC
Original   256  ACTGAAAGAACAACTGAATTTTGGAAGCAGTATGTTGATGGAGATCAGTGTGAGTCCAAT Optimized  316  CCCTGTCTCGAATGGCGGAAGTTGCAAAGACGATACAACTCATACGAATGCTGGTGTCCT
Original   316  CCATGTTTAAATGGCGGCAGTTGCAAGGATGACATTAATTCCTATGAATGTTGGTGTCCC Optimized  376  TTCGGGTTTGAAGGCCAAAAATTGCCAGCTGGACGTCACATGTAACATTAAGAATGGACGG
Original   376  TTTGGATTTGAAGGAAAGAACTGTGAATTAGATGTAACATGTAACATTAAGAATGGCAGA Optimized  436  TGCGAGCAGTTTTGTAAAAACTCTGCCGATAATAAGGTGGTGTGCAGCTGTACTGAAGGA
Original   436  TGCGAGCAGTTTTGTAAAAATAGTGCTGATAACAAGGTGGTTTGCTCCTGTACTGAGGGA
```

FIG. 5

```
Optimized 496  TATCGCCCTGGCTGAGAATCCAGAAGTCCTGCGAACCAGCAGTGCCCTTCCCTTGTGGGAGG
Original  496  TATCGACTTGCAGAAAACCAGAAGTCCTGTGAACCAGCAGTGCCATTTCCATGTGGAAGA Optimized 556  GTGAGCCGTCTCCCAGACTTCAAAACTGACCAGAGACAGTGTTTCCCGACTGTGCAT
Original  556  GTTTCTGTTTCACAAACTTCTAAGCTCACCCGTGCTGAGACTGTTTTCCTGATGTGGAC Optimized 616  TACGTCAAACAGCACTGAGGCCGAAACCATCCTGGACAACATTACTCAGTCTACCCAGAGT
Original  616  TATGTAAATTCTACTGAAGCTGAAACCATTTTGGATAACATCACTCAAAGCACCCAATCA Optimized 676  TTCAATGACTTTACTCGGGTGGTCTCGGGGGCCGAGGATGCTAAACCAGGCCAGTTCCCTGG
Original  676  TTTAATGACTTCACTCGGGTTGTTGTTGGTGGAGAAGATGCCAAACCAGGTCAATTCCCTTGG Optimized 736  CAGGTGGTCCTGAAACGGAAAAGGTGGATGCATTTTGCGGAGGGTCTATCGTGAATGAGAAA
Original  736  CAGGTTGTTTTGAATGGTAAAGTTGATGCATTCTGTGGAGGCTCTATCGTTAATGAAAAA Optimized 796  TGGATTGTCACCGCCGCTCACTGCGTGGAAACCGAGTCAAGATCACAGTGGTCGCTGG
Original  796  TGGATTGTAACTGCTGCCCACTGTGTTGAAACTGGTGTTAAATTACAGTTGTCGCAGGT Optimized 856  CAGCACAACATTGAGGAAACAGAACATACTGAGCAGAAGCGGAATGTGATCCGATCATT
Original  856  GAACATAATATTGAGGAGACAGAACATACAGAGCAAAAGCGAAATGTGATTCGAATTATT Optimized 916  CCTCACCATAACTACAATGCAGCCATCAACAAATACAATCATGACATTGCCCTGCTGGAA
Original  916  CCTCACCACCAACTACAATGCAATGCTATTAATAAGTACAACCATGACATTGCCCTTCTGGAA
```

FIG. 5, cont'd

```
Optimized  976  CTGGATGAGCCCTCTGGTGCTGAACAGCTACGTCACTCCAATCTGCATTGCTGACAAAGAG
Original   976  CTGGACGAACCCTTAGTGCTAAACAGCTACGTTACACCTATTGCATTTGCTGACAAGGAA Optimized 1036  TATACCAATATCTTCCTGAAGTTTGGATCAGGGTACGTGAGCGGCTGGGAAGAGTCTTC
Original  1036  TACACGAACATCTTCCTCAAATTTGGATCTGGCTATGTAAGTGGCTGGGAAGAGTCTTC Optimized 1096  CACAAGGGCAGGAGCGCCCTGGTGCTCCAGTATCTGCGAGTGCCCTTGGTCGATCGACCT
Original  1096  CACAAAGGGAGATCAGCTTTAGTTCTTCAGTACCTTAGAGTTCCACTTGTTGACCGAGCC Optimized 1156  ACCTGTCTGAGCTCTACCAAGTTTACAATCTACAACAACATGTTCTCGCTGGTTTCAC
Original  1156  ACATGTCTTCGATCTACAAAGTTCACCATCTATAACAACATGTTCTGTGCTGGCTTCCAT Optimized 1216  GAGGAGGAACGAGACTCCTGTCAGGCGATTCTGGGGCCCACATGTGACAGAGGTCGAA
Original  1216  GAAGGAGGTAGAGATTCATGTCAAGGAGGAGATAGTGGGGACCCCATGTTACTGAAGTGGAA Optimized 1276  GGCACCAGCTTCCTGACTGGCATCATTCCTGGGGAGGAATGTGCAATGAAGGAAAA
Original  1276  GGGACCAGTTTCTTAACTGGAATTATTAGCTGGGGTGAAGAGTGTGCAATGAAAGGCAAA Optimized 1336  TACGGGATCTACACCAAAGTGAGCGCCTATGTGAACTGGATCAAGGAAAAAACCAAACTG
Original  1336  TATGGAATATATACCAAGGTATCCCGGTATGTCAACTGGATTAAGGAAAAAACAAAGCTC Optimized 1396  ACCTAAATGA
Original  1396  ACTTGATAA
```

FIG. 5, cont'd

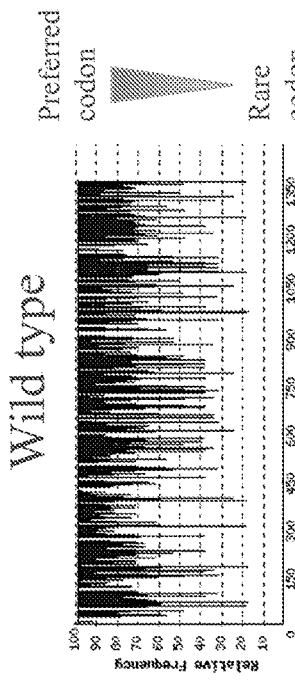
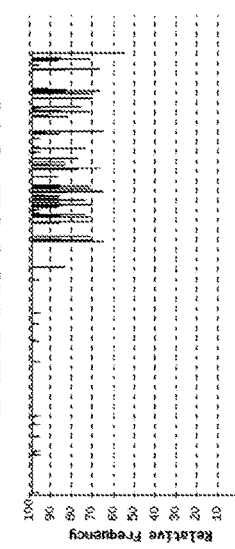
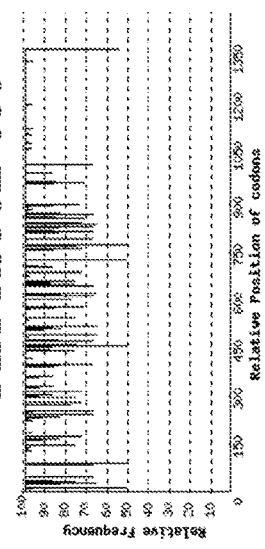
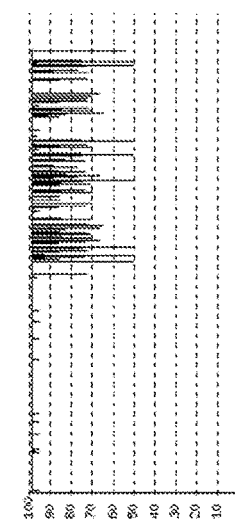
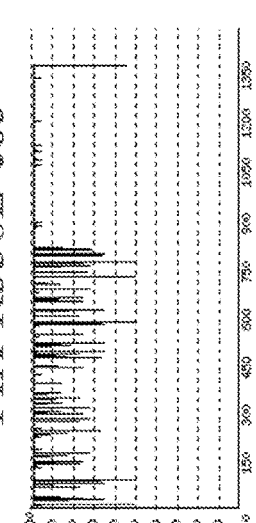
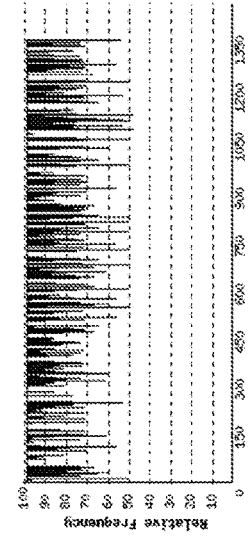
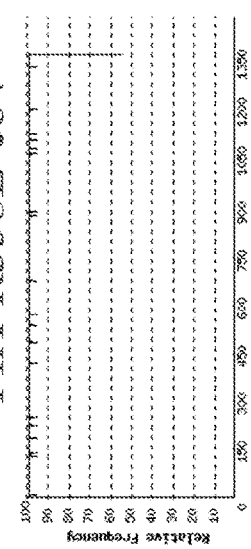
FIG. 6

SEQUENCE LISTING

<160> NUMBER OF SEQ ID NOS: 58

<210> SEQ ID NO 1
<211> LENGTH: 1389
<212> TYPE: DNA
<213> ORGANISM: Artificial Sequence
<220> FEATURE:
<223> OTHER INFORMATION: optimized human factor IX nucleotide sequence

<400> SEQUENCE: 1

```
atgcagagag tcaacatgat tatggctgag tcacctgggc tgattactat ttgcctgctg     60
ggctacctgc tgtccgccga gtgtaccgtg ttcctggacc atgagaacgc aaataagatc    120
ctgaacaggc ccaaaagata caatagtggg aagctggagg aatttgtgca gggcaacctg    180
gagagagaat gcatggagga aaagtgtagc ttcgaggaag cccgcgaggt gtttgaaaat    240
acagagcgaa ccacagagtt ctggaagcag tatgtggacg gcgatcagtg cgagagcaac    300
ccctgtctga atggcggaag ttgcaaagac gatatcaact catacgaatg ctggtgtcct    360
ttcgggtttg aaggcaaaaa ttgcgagctg gacgtgacat gtaacattaa gaatggacgg    420
tgcgagcagt tttgtaaaaa ctctgccgat aataaggtgg tgtgcagctg tactgaagga    480
tatcgcctgg ctgagaacca gaagtcctgc gaaccagcag tgcccttccc ttgtgggagg    540
gtgagcgtct cccagacttc aaaactgacc agagcagaga cagtgttttcc cgacgtggat    600
tacgtcaaca gcactgaggc cgaaaccatc ctggacaaca ttactcagtc tacccagagt    660
ttcaatgact ttactcgggt ggtcgggggc gaggatgcta aaccaggcca gttcccctgg    720
caggtggtcc tgaacggaaa ggtggatgca ttttgcggag ggtctatcgt gaatgagaaa    780
tggattgtca ccgccgctca ctgcgtggaa accggagtca agatcacagt ggtcgctggg    840
gagcacaaca ttgaggaaac agaacatact gagcagaagc ggaatgtgat ccgcatcatt    900
cctcaccata actacaatgc agccatcaac aaatacaatc atgacattgc cctgctggaa    960
ctggatgagc ctctggtgct gaacagctac gtcactccaa tctgcattgc tgacaaagag   1020
tataccaata tcttcctgaa gtttggatca gggtacgtga gcggctgggg aagagtcttc   1080
cacaagggca ggagcgccct ggtgctccag tatctgcgag tgcctctggt cgatcgagct   1140
acctgtctga ggtctaccaa gtttacaatc tacaacaaca tgttctgcgc tgggtttcac   1200
gagggaggac gagactcctg tcagggcgat tctgggggcc acatgtgaca gaggtcgaa   1260
ggcaccagct tcctgactgg catcatttcc tggggagagg aatgtgcaat gaagggaaaa   1320
tacgggatct acaccaaagt gagccgctat gtgaactgga tcaaggaaaa aaccaaactg   1380
acctaatga                                                          1389
```

<210> SEQ ID NO 2
<211> LENGTH: 1389
<212> TYPE: DNA
<213> ORGANISM: Homo sapiens

<400> SEQUENCE: 2

```
atgcagcgcg tgaacatgat catggcagaa tcaccaggcc tcatcaccat ctgccttttta    60
ggatatctac tcagtgctga atgtacagtt tttcttgatc atgaaaacgc caacaaaatt   120
```

```
ctgaatcggc caaagaggta taattcaggt aaattggaag agtttgttca agggaatcta      180
gagagagaat gtatggaaga aaagtgtagt tttgaagaag cacgagaagt ttttgaaaac      240
actgaaagaa caactgaatt ttggaagcag tatgttgatg agatcagtg tgagtccaat       300 ccatgtttaa atggcggcag ttgcaaggat gacattaatt cctatgaatg ttggtgtccc      360
tttggatttg aaggaaagaa ctgtgaatta gatgtaacat gtaacattaa gaatggcaga     420
tgcgagcagt tttgtaaaaa tagtgctgat aacaaggtgg tttgctcctg tactgaggga     480
tatcgacttg cagaaaacca gaagtcctgt gaaccagcag tgccatttcc atgtggaaga    540
gtttctgttt cacaaacttc taagctcacc cgtgctgaga ctgttttttcc tgatgtggac     600 tatgtaaatt ctactgaagc tgaaaccatt ttggataaca tcactcaaag cacccaatca     660
tttaatgact tcactcgggt tgttggtgga agatgccaa aaccaggtca attcccttgg       720
caggttgttt tgaatggtaa agttgatgca ttctgtggag gctctatcgt taatgaaaaa    780
tggattgtaa ctgctgccca ctgtgttgaa actggtgtta aaattacagt tgtcgcaggt     840
gaacataata ttgaggagac agaacataca gagcaaaagc gaaatgtgat tcgaattatt     900
cctcaccaca actacaatgc agctattaat aagtacaacc atgacattgc ccttctggaa     960
ctggacgaac ccttagtgct aaacagctac gttacaccta tttgcattgc tgacaaggaa   1020
tacacgaaca tcttcctcaa atttggatct ggctatgtaa gtggctgggg aagagtcttc  1080
cacaaaggga atcagctttt agttcttcag taccttagag ttccacttgt tgaccgagcc    1140
acatgtcttc gatctacaaa gttcaccatc tataacaaca tgttctgtgc tggcttccat     1200
gaaggaggta gagattcatg tcaaggagat agtgggggac cccatgttac tgaagtggaa  1260
gggaccagtt tcttaactgg aattattagc tggggtgaag agtgtgcaat gaaaggcaaa    1320
tatggaatat ataccaaggt atcccggtat gtcaactgga ttaaggaaaa aacaaagctc    1380
acttgataa                                                              1389
```

<210> SEQ ID NO 3
<211> LENGTH: 461
<212> TYPE: PRT
<213> ORGANISM: Homo sapiens
<220> FEATURE:
<221> NAME/KEY: SIGNAL
<222> LOCATION: (1)..(28)
<223> OTHER INFORMATION: FIX Signal Peptide
<220> FEATURE:
<221> NAME/KEY: PROPEP
<222> LOCATION: (29)..(46)
<223> OTHER INFORMATION: FIX Propeptide

<400> SEQUENCE: 3

Met Gln Arg Val Asn Met Ile Met Ala Glu Ser Pro Gly Leu Ile Thr
1               5                   10                  15

Ile Cys Leu Leu Gly Tyr Leu Leu Ser Ala Glu Cys Thr Val Phe Leu
            20                  25                  30

Asp His Glu Asn Ala Asn Lys Ile Leu Asn Arg Pro Lys Arg Tyr Asn
        35                  40                  45

Ser Gly Lys Leu Glu Glu Phe Val Gln Gly Asn Leu Glu Arg Glu Cys
    50                  55                  60

Met Glu Glu Lys Cys Ser Phe Glu Glu Ala Arg Glu Val Phe Glu Asn
65                  70                  75                  80

Thr Glu Arg Thr Thr Glu Phe Trp Lys Gln Tyr Val Asp Gly Asp Gln
                85                  90                  95

```
Cys Glu Ser Asn Pro Cys Leu Asn Gly Ser Cys Lys Asp Asp Ile
             100                 105                 110

Asn Ser Tyr Glu Cys Trp Cys Pro Phe Gly Phe Glu Gly Lys Asn Cys
         115                 120                 125

Glu Leu Asp Val Thr Cys Asn Ile Lys Asn Gly Arg Cys Glu Gln Phe
    130                 135                 140

Cys Lys Asn Ser Ala Asp Asn Lys Val Val Cys Ser Cys Thr Glu Gly
145                 150                 155                 160

Tyr Arg Leu Ala Glu Asn Gln Lys Ser Cys Glu Pro Ala Val Pro Phe
                165                 170                 175

Pro Cys Gly Arg Val Ser Val Ser Gln Thr Ser Lys Leu Thr Arg Ala
            180                 185                 190

Glu Thr Val Phe Pro Asp Val Asp Tyr Val Asn Ser Thr Glu Ala Glu
        195                 200                 205

Thr Ile Leu Asp Asn Ile Thr Gln Ser Thr Gln Ser Phe Asn Asp Phe
    210                 215                 220

Thr Arg Val Val Gly Gly Glu Asp Ala Lys Pro Gly Gln Phe Pro Trp
225                 230                 235                 240

Gln Val Val Leu Asn Gly Lys Val Asp Ala Phe Cys Gly Gly Ser Ile
                245                 250                 255

Val Asn Glu Lys Trp Ile Val Thr Ala Ala His Cys Val Glu Thr Gly
            260                 265                 270

Val Lys Ile Thr Val Val Ala Gly Glu His Asn Ile Glu Glu Thr Glu
        275                 280                 285

His Thr Glu Gln Lys Arg Asn Val Ile Arg Ile Pro His His Asn
    290                 295                 300

Tyr Asn Ala Ala Ile Asn Lys Tyr Asn His Asp Ile Ala Leu Leu Glu
305                 310                 315                 320

Leu Asp Glu Pro Leu Val Leu Asn Ser Tyr Val Thr Pro Ile Cys Ile
                325                 330                 335

Ala Asp Lys Glu Tyr Thr Asn Ile Phe Leu Lys Phe Gly Ser Gly Tyr
            340                 345                 350

Val Ser Gly Trp Gly Arg Val Phe His Lys Gly Arg Ser Ala Leu Val
        355                 360                 365

Leu Gln Tyr Leu Arg Val Pro Leu Val Asp Arg Ala Thr Cys Leu Leu
    370                 375                 380

Ser Thr Lys Phe Thr Ile Tyr Asn Asn Met Phe Cys Ala Gly Phe His
385                 390                 395                 400

Glu Gly Gly Arg Asp Ser Cys Gln Gly Asp Ser Gly Gly Pro His Val
                405                 410                 415

Thr Glu Val Glu Gly Thr Ser Phe Leu Thr Gly Ile Ile Ser Trp Gly
            420                 425                 430

Glu Glu Cys Ala Met Lys Gly Lys Tyr Gly Ile Tyr Thr Lys Val Ser
        435                 440                 445

Arg Tyr Val Asn Trp Ile Lys Glu Lys Thr Lys Leu Thr
    450                 455                 460

<210> SEQ ID NO 4
<211> LENGTH: 6
<212> TYPE: DNA
<213> ORGANISM: Artificial Sequence
<220> FEATURE:
<223> OTHER INFORMATION: Potential Splice Site

<400> SEQUENCE: 4
```

```
ggtgat                                                              6
```

<210> SEQ ID NO 5
<211> LENGTH: 6
<212> TYPE: DNA
<213> ORGANISM: Artificial Sequence
<220> FEATURE:
<223> OTHER INFORMATION: Potential Splice Site

<400> SEQUENCE: 5

```
ggtaag                                                              6
```

<210> SEQ ID NO 6
<211> LENGTH: 5
<212> TYPE: DNA
<213> ORGANISM: Artificial Sequence
<220> FEATURE:
<223> OTHER INFORMATION: Destabilizing Sequence

<400> SEQUENCE: 6

```
attta                                                               5
```

<210> SEQ ID NO 7
<211> LENGTH: 6
<212> TYPE: DNA
<213> ORGANISM: Artificial Sequence
<220> FEATURE:
<223> OTHER INFORMATION: poly-T Sequence

<400> SEQUENCE: 7

```
tttttt                                                              6
```

<210> SEQ ID NO 8
<211> LENGTH: 7
<212> TYPE: DNA
<213> ORGANISM: Artificial Sequence
<220> FEATURE:
<223> OTHER INFORMATION: poly-A Sequence

<400> SEQUENCE: 8

```
aaaaaaa                                                             7
```

<210> SEQ ID NO 9
<211> LENGTH: 6
<212> TYPE: DNA
<213> ORGANISM: Artificial Sequence
<220> FEATURE:
<223> OTHER INFORMATION: poly-A Sequence

<400> SEQUENCE: 9

```
aataaa                                                              6
```

<210> SEQ ID NO 10
<211> LENGTH: 6
<212> TYPE: DNA
<213> ORGANISM: Artificial Sequence
<220> FEATURE:
<223> OTHER INFORMATION: poly-A Sequence

<400> SEQUENCE: 10

```
attaaa                                                              6
```

<210> SEQ ID NO 11
<211> LENGTH: 5
<212> TYPE: DNA
<213> ORGANISM: Artificial Sequence
<220> FEATURE:
<223> OTHER INFORMATION: antiviral motif

<400> SEQUENCE: 11 tgtgt                                                                 5

<210> SEQ ID NO 12

<400> SEQUENCE: 12

000

<210> SEQ ID NO 13

<400> SEQUENCE: 13

000

<210> SEQ ID NO 14
<211> LENGTH: 8
<212> TYPE: DNA
<213> ORGANISM: Artificial Sequence
<220> FEATURE:
<223> OTHER INFORMATION: AU Rich Sequence Elements (ARE)

<400> SEQUENCE: 14 attttatt                                                              8

<210> SEQ ID NO 15
<211> LENGTH: 8
<212> TYPE: DNA
<213> ORGANISM: Artificial Sequence
<220> FEATURE:
<223> OTHER INFORMATION: AU Rich Sequence Elements (ARE)

<400> SEQUENCE: 15 attttaa                                                               8

<210> SEQ ID NO 16

<400> SEQUENCE: 16

000

<210> SEQ ID NO 17
<211> LENGTH: 32
<212> TYPE: PRT
<213> ORGANISM: Artificial Sequence
<220> FEATURE:
<223> OTHER INFORMATION: CTP peptide

<400> SEQUENCE: 17

Asp Pro Arg Phe Gln Asp Ser Ser Ser Ser Lys Ala Pro Pro Pro Ser
1               5                   10                  15

Leu Pro Ser Pro Ser Arg Leu Pro Gly Pro Ser Asp Thr Pro Ile Leu
            20                  25                  30

<210> SEQ ID NO 18
<211> LENGTH: 28
<212> TYPE: PRT
<213> ORGANISM: Artificial Sequence
<220> FEATURE:
<223> OTHER INFORMATION: CTP peptide

<400> SEQUENCE: 18

Ser Ser Ser Ser Lys Ala Pro Pro Pro Ser Leu Pro Ser Pro Ser Arg

```
1               5                   10                  15
Leu Pro Gly Pro Ser Asp Thr Pro Ile Leu Pro Gln
            20                  25

<210> SEQ ID NO 19
<211> LENGTH: 11
<212> TYPE: PRT
<213> ORGANISM: Artificial Sequence
<220> FEATURE:
<223> OTHER INFORMATION: albumin-binding peptides core sequence

<400> SEQUENCE: 19

Asp Ile Cys Leu Pro Arg Trp Gly Cys Leu Trp
1               5                   10

<210> SEQ ID NO 20
<211> LENGTH: 20
<212> TYPE: PRT
<213> ORGANISM: Artificial Sequence
<220> FEATURE:
<223> OTHER INFORMATION: PAS Sequence

<400> SEQUENCE: 20

Ala Ser Pro Ala Ala Pro Ala Pro Ala Ser Pro Ala Ala Pro Ala Pro
1               5                   10                  15

Ser Ala Pro Ala
            20

<210> SEQ ID NO 21
<211> LENGTH: 20
<212> TYPE: PRT
<213> ORGANISM: Artificial Sequence
<220> FEATURE:
<223> OTHER INFORMATION: PAS Sequence

<400> SEQUENCE: 21

Ala Ala Pro Ala Ser Pro Ala Pro Ala Ala Pro Ser Ala Pro Ala Pro
1               5                   10                  15

Ala Ala Pro Ser
            20

<210> SEQ ID NO 22
<211> LENGTH: 20
<212> TYPE: PRT
<213> ORGANISM: Artificial Sequence
<220> FEATURE:
<223> OTHER INFORMATION: PAS Sequence

<400> SEQUENCE: 22

Ala Pro Ser Ser Pro Ser Pro Ser Ala Pro Ser Ser Pro Ser Pro Ala
1               5                   10                  15

Ser Pro Ser Ser
            20

<210> SEQ ID NO 23
<211> LENGTH: 19
<212> TYPE: PRT
<213> ORGANISM: Artificial Sequence
<220> FEATURE:
<223> OTHER INFORMATION: PAS Sequence

<400> SEQUENCE: 23

Ala Pro Ser Ser Pro Ser Pro Ser Ala Pro Ser Ser Pro Ser Pro Ala
1               5                   10                  15
```

Ser Pro Ser

<210> SEQ ID NO 24
<211> LENGTH: 20
<212> TYPE: PRT
<213> ORGANISM: Artificial Sequence
<220> FEATURE:
<223> OTHER INFORMATION: PAS Sequence

<400> SEQUENCE: 24

Ser Ser Pro Ser Ala Pro Ser Pro Ser Ser Pro Ala Ser Pro Ser Pro
1               5                   10                  15

Ser Ser Pro Ala
            20

<210> SEQ ID NO 25
<211> LENGTH: 24
<212> TYPE: PRT
<213> ORGANISM: Artificial Sequence
<220> FEATURE:
<223> OTHER INFORMATION: PAS Sequence

<400> SEQUENCE: 25

Ala Ala Ser Pro Ala Ala Pro Ser Ala Pro Pro Ala Ala Ala Ser Pro
1               5                   10                  15

Ala Ala Pro Ser Ala Pro Pro Ala
            20

<210> SEQ ID NO 26
<211> LENGTH: 20
<212> TYPE: PRT
<213> ORGANISM: Artificial Sequence
<220> FEATURE:
<223> OTHER INFORMATION: PAS Sequence

<400> SEQUENCE: 26

Ala Ser Ala Ala Ala Pro Ala Ala Ala Ser Ala Ala Ala Ser Ala Pro
1               5                   10                  15

Ser Ala Ala Ala
            20

<210> SEQ ID NO 27

<400> SEQUENCE: 27

000

<210> SEQ ID NO 28

<400> SEQUENCE: 28

000

<210> SEQ ID NO 29
<211> LENGTH: 4
<212> TYPE: PRT
<213> ORGANISM: Artificial Sequence
<220> FEATURE:
<223> OTHER INFORMATION: human IgG1 amino acids 233-236

<400> SEQUENCE: 29

Glu Leu Leu Gly
1

<210> SEQ ID NO 30

<211> LENGTH: 42
<212> TYPE: PRT
<213> ORGANISM: Artificial Sequence
<220> FEATURE:
<223> OTHER INFORMATION: XTEN AE42-4

<400> SEQUENCE: 30

Gly Ala Pro Gly Ser Pro Ala Gly Ser Pro Thr Ser Thr Glu Glu Gly
1               5                   10                  15

Thr Ser Glu Ser Ala Thr Pro Glu Ser Gly Pro Gly Ser Glu Pro Ala
            20                  25                  30

Thr Ser Gly Ser Glu Thr Pro Ala Ser Ser
        35                  40

<210> SEQ ID NO 31
<211> LENGTH: 126
<212> TYPE: DNA
<213> ORGANISM: Artificial Sequence
<220> FEATURE:
<223> OTHER INFORMATION: XTEN AE42-4

<400> SEQUENCE: 31
ggcgcgccag gttctcctgc tggctccccc acctcaacag aagaggggac aagcgaaagc       60
gctacgcctg agagtggccc tggctctgag ccagccacct ccggctctga aacccctgcc      120
tcgagc                                                                 126

<210> SEQ ID NO 32
<211> LENGTH: 144
<212> TYPE: PRT
<213> ORGANISM: Artificial Sequence
<220> FEATURE:
<223> OTHER INFORMATION: XTEN AE144-2A

<400> SEQUENCE: 32

Thr Ser Thr Glu Pro Ser Glu Gly Ser Ala Pro Gly Ser Pro Ala Gly
1               5                   10                  15

Ser Pro Thr Ser Thr Glu Glu Gly Thr Ser Thr Glu Pro Ser Glu Gly
            20                  25                  30

Ser Ala Pro Gly Thr Ser Thr Glu Pro Ser Glu Gly Ser Ala Pro Gly
        35                  40                  45

Thr Ser Glu Ser Ala Thr Pro Glu Ser Gly Pro Gly Thr Ser Thr Glu
    50                  55                  60

Pro Ser Glu Gly Ser Ala Pro Gly Thr Ser Glu Ser Ala Thr Pro Glu
65                  70                  75                  80

Ser Gly Pro Gly Ser Glu Pro Ala Thr Ser Gly Ser Glu Thr Pro Gly
                85                  90                  95

Thr Ser Thr Glu Pro Ser Glu Gly Ser Ala Pro Gly Thr Ser Thr Glu
            100                 105                 110

Pro Ser Glu Gly Ser Ala Pro Gly Thr Ser Glu Ser Ala Thr Pro Glu
        115                 120                 125

Ser Gly Pro Gly Thr Ser Glu Ser Ala Thr Pro Glu Ser Gly Pro Gly
    130                 135                 140

<210> SEQ ID NO 33
<211> LENGTH: 450
<212> TYPE: DNA
<213> ORGANISM: Artificial Sequence
<220> FEATURE:
<223> OTHER INFORMATION: XTEN AE144-2A

<400> SEQUENCE: 33

```
ggcgcgccaa ccagtacgga gccgtccgag gggagcgcac caggaagccc ggctgggagc    60
ccgacttcta ccgaagaggg tacatctacc gaaccaagtg aaggttcagc accaggcacc   120
tcaacagaac cctctgaggg ctcggcgcct ggtacaagtg agtccgccac cccagaatcc   180
gggcctggga caagcacaga accttcggaa gggagtgccc ctggaacatc cgaatcggca   240
accccagaat cagggccagg atctgagccc gcgacttcgg gctccgagac gcctgggaca   300
tccaccgagc cctccgaagg atcagcccca ggcaccagca cggagccctc tgagggaagc   360
gcacctggta ccagcgaaag cgcaactccc gaatcaggtc ccggtacgag cgagtcggcg   420
accccggaga gcgggccagg tgcctcgagc                                    450
```

<210> SEQ ID NO 34
<211> LENGTH: 144
<212> TYPE: PRT
<213> ORGANISM: Artificial Sequence
<220> FEATURE:
<223> OTHER INFORMATION: XTEN AE144-3B

<400> SEQUENCE: 34

```
Ser Pro Ala Gly Ser Pro Thr Ser Thr Glu Glu Gly Thr Ser Glu Ser
1               5                   10                  15

Ala Thr Pro Glu Ser Gly Pro Gly Ser Glu Pro Ala Thr Ser Gly Ser
                20                  25                  30

Glu Thr Pro Gly Thr Ser Glu Ser Ala Thr Pro Glu Ser Gly Pro Gly
            35                  40                  45

Thr Ser Thr Glu Pro Ser Glu Gly Ser Ala Pro Gly Thr Ser Thr Glu
        50                  55                  60

Pro Ser Glu Gly Ser Ala Pro Gly Thr Ser Thr Glu Pro Ser Glu Gly
65                  70                  75                  80

Ser Ala Pro Gly Thr Ser Thr Glu Pro Ser Glu Gly Ser Ala Pro Gly
                85                  90                  95

Thr Ser Thr Glu Pro Ser Glu Gly Ser Ala Pro Gly Thr Ser Thr Glu
            100                 105                 110

Pro Ser Glu Gly Ser Ala Pro Gly Ser Pro Ala Gly Ser Pro Thr Ser
        115                 120                 125

Thr Glu Glu Gly Thr Ser Thr Glu Pro Ser Glu Gly Ser Ala Pro Gly
    130                 135                 140
```

<210> SEQ ID NO 35
<211> LENGTH: 450
<212> TYPE: DNA
<213> ORGANISM: Artificial Sequence
<220> FEATURE:
<223> OTHER INFORMATION: XTEN AE144-3B

<400> SEQUENCE: 35

```
ggcgcgccaa gtcccgctgg aagcccaact agcaccgaag agggacctc agagtccgcc     60 accccgagt ccggccctgg ctctgagcct gccactagcg gctccgagac tcctggcaca    120
tccgaaagcg ctacacccga gagtggaccc ggcacctcta ccgagcccag tgagggctcc   180
gcccctggaa caagcaccga gcccagcgaa ggcagcgccc cagggacctc cacagagccc   240
agtgaaggca gtgctcctgg caccagcacc gaaccaagcg agggctctgc acccgggacc   300
tccaccgagc caagcgaagg ctctgcccct ggcacttcca ccgagcccag cgaaggcagc   360
gcccctggga gcccgctggg ctctcccacc agcactgagg agggcacatc taccgaacca   420
agtgaaggct ctgcaccagg tgcctcgagc                                    450
```

<210> SEQ ID NO 36
<211> LENGTH: 144
<212> TYPE: PRT
<213> ORGANISM: Artificial Sequence
<220> FEATURE:
<223> OTHER INFORMATION: XTEN AE144-4A

<400> SEQUENCE: 36

Thr Ser Glu Ser Ala Thr Pro Glu Ser Gly Pro Gly Ser Glu Pro Ala
1               5                   10                  15

Thr Ser Gly Ser Glu Thr Pro Gly Thr Ser Glu Ser Ala Thr Pro Glu
            20                  25                  30

Ser Gly Pro Gly Ser Glu Pro Ala Thr Ser Gly Ser Glu Thr Pro Gly
        35                  40                  45

Thr Ser Glu Ser Ala Thr Pro Glu Ser Gly Pro Gly Thr Ser Thr Glu
    50                  55                  60

Pro Ser Glu Gly Ser Ala Pro Gly Thr Ser Glu Ser Ala Thr Pro Glu
65                  70                  75                  80

Ser Gly Pro Gly Ser Pro Ala Gly Ser Pro Thr Ser Thr Glu Glu Gly
                85                  90                  95

Ser Pro Ala Gly Ser Pro Thr Ser Thr Glu Glu Gly Ser Pro Ala Gly
            100                 105                 110

Ser Pro Thr Ser Thr Glu Glu Gly Thr Ser Glu Ser Ala Thr Pro Glu
        115                 120                 125

Ser Gly Pro Gly Thr Ser Thr Glu Pro Ser Glu Gly Ser Ala Pro Gly
    130                 135                 140

<210> SEQ ID NO 37
<211> LENGTH: 450
<212> TYPE: DNA
<213> ORGANISM: Artificial Sequence
<220> FEATURE:
<223> OTHER INFORMATION: XTEN AE144-4A

<400> SEQUENCE: 37
ggcgcgccaa cgtccgaaag tgctacccct gagtcaggcc ctggtagtga gcctgccaca      60
agcggaagcg aaactccggg gacctcagag tctgccactc ccgaatcggg gccaggctct     120
gaaccggcca cttcagggag cgaaacacca ggaacatcgg agagcgctac cccggagagc     180
gggccaggaa ctagtactga gcctagcgag ggaagtgcac tggtacaagc gagtccgcc      240 acacccgagt ctggccctgg ctctccagcg ggctcaccca cgagcactga gagggctct      300 cccgctggca gcccaacgtc gacagaagaa ggatcaccag caggctcccc cacatcaaca     360
gaggagggta catcagaatc tgctactccc gagagtggac ccggtacctc cactgagccc     420
agcgagggga gtgcaccagg tgcctcgagc                                      450

<210> SEQ ID NO 38
<211> LENGTH: 144
<212> TYPE: PRT
<213> ORGANISM: Artificial Sequence
<220> FEATURE:
<223> OTHER INFORMATION: XTEN AE144-5A

<400> SEQUENCE: 38

Thr Ser Glu Ser Ala Thr Pro Glu Ser Gly Pro Gly Ser Glu Pro Ala
1               5                   10                  15

Thr Ser Gly Ser Glu Thr Pro Gly Thr Ser Glu Ser Ala Thr Pro Glu
            20                  25                  30

Ser Gly Pro Gly Ser Glu Pro Ala Thr Ser Gly Ser Glu Thr Pro Gly
         35                  40                  45

Thr Ser Glu Ser Ala Thr Pro Glu Ser Gly Pro Gly Thr Ser Thr Glu
 50                  55                  60

Pro Ser Glu Gly Ser Ala Pro Gly Ser Pro Ala Gly Ser Pro Thr Ser
 65                  70                  75                  80

Thr Glu Glu Gly Thr Ser Glu Ser Ala Thr Pro Glu Ser Gly Pro Gly
                 85                  90                  95

Ser Glu Pro Ala Thr Ser Gly Ser Glu Thr Pro Gly Thr Ser Glu Ser
                100                 105                 110

Ala Thr Pro Glu Ser Gly Pro Gly Ser Pro Ala Gly Ser Pro Thr Ser
                115                 120                 125

Thr Glu Glu Gly Ser Pro Ala Gly Ser Pro Thr Ser Thr Glu Glu Gly
                130                 135                 140

<210> SEQ ID NO 39
<211> LENGTH: 450
<212> TYPE: DNA
<213> ORGANISM: Artificial Sequence
<220> FEATURE:
<223> OTHER INFORMATION: XTEN AE144-5A

<400> SEQUENCE: 39
ggcgcgccaa catcagagag cgccacccct gaaagtggtc ccgggagcga gccagccaca      60
tctgggtcgg aaacgccagg cacaagtgag tctgcaactc ccgagtccgg acctggctcc     120
gagcctgcca ctagcggctc cgagactccg ggaacttccg agagcgctac accagaaagc     180
ggacccggaa ccagtaccga acctagcgag ggctctgctc cgggcagccc agccggctct     240
cctacatcca cggaggaggg cacttccgaa tccgccaccc cggagtcagg gccaggatct     300
gaacccgcta cctcaggcag tgagacgcca ggaacgagcg agtccgctac accggagagt     360
gggccaggga gccctgctgg atctcctacg tccactgagg aagggtcacc agcgggctcg     420
cccaccagca ctgaagaagg tgcctcgagc                                       450

<210> SEQ ID NO 40
<211> LENGTH: 144
<212> TYPE: PRT
<213> ORGANISM: Artificial Sequence
<220> FEATURE:
<223> OTHER INFORMATION: XTEN AE144-6B

<400> SEQUENCE: 40

Thr Ser Thr Glu Pro Ser Glu Gly Ser Ala Pro Gly Thr Ser Glu Ser
 1               5                  10                  15

Ala Thr Pro Glu Ser Gly Pro Gly Thr Ser Glu Ser Ala Thr Pro Glu
                 20                  25                  30

Ser Gly Pro Gly Thr Ser Glu Ser Ala Thr Pro Glu Ser Gly Pro Gly
                 35                  40                  45

Ser Glu Pro Ala Thr Ser Gly Ser Glu Thr Pro Gly Ser Glu Pro Ala
                 50                  55                  60

Thr Ser Gly Ser Glu Thr Pro Gly Ser Pro Ala Gly Ser Pro Thr Ser
 65                  70                  75                  80

Thr Glu Glu Gly Thr Ser Thr Glu Pro Ser Glu Gly Ser Ala Pro Gly
                 85                  90                  95

Thr Ser Thr Glu Pro Ser Glu Gly Ser Ala Pro Gly Ser Glu Pro Ala
                100                 105                 110

Thr Ser Gly Ser Glu Thr Pro Gly Thr Ser Glu Ser Ala Thr Pro Glu
            115                 120                 125

Ser Gly Pro Gly Thr Ser Thr Glu Pro Ser Glu Gly Ser Ala Pro Gly
    130                 135                 140

<210> SEQ ID NO 41
<211> LENGTH: 450
<212> TYPE: DNA
<213> ORGANISM: Artificial Sequence
<220> FEATURE:
<223> OTHER INFORMATION: XTEN AE144-6B

<400> SEQUENCE: 41
ggcgcgccaa catctaccga gccttccgaa ggctctgccc ctgggacctc agaatctgca     60
acccctgaaa gcggccctgg aacctccgaa agtgccactc ccgagagcgg cccagggaca    120
agcgagtcag caaccccctga gtctggaccc ggcagcgagc ctgcaacctc tggctcagag    180
actcccggct cagaacccgc tacctcaggc tccgagacac ccggctctcc tgctgggagt    240
cccacttcca ccgaggaagg aacatccact gagcctagtg agggctctgc ccctggaacc    300
agcacagagc caagtgaggg cagtgcacca ggatccgagc cagcaaccag cgggtccgag    360
actcccggga cctctgagtc tgccacccca gagagcggac ccggcacttc aaccgagccc    420
tccgaaggat cagcaccagg tgcctcgagc                                     450

<210> SEQ ID NO 42
<211> LENGTH: 144
<212> TYPE: PRT
<213> ORGANISM: Artificial Sequence
<220> FEATURE:
<223> OTHER INFORMATION: XTEN AG144-1

<400> SEQUENCE: 42

Pro Gly Ser Ser Pro Ser Ala Ser Thr Gly Thr Gly Pro Gly Ser Ser
1               5                   10                  15

Pro Ser Ala Ser Thr Gly Thr Gly Pro Gly Thr Pro Gly Ser Gly Thr
            20                  25                  30

Ala Ser Ser Ser Pro Gly Ser Ser Thr Pro Ser Gly Ala Thr Gly Ser
        35                  40                  45

Pro Gly Ser Ser Pro Ser Ala Ser Thr Gly Thr Gly Pro Gly Ala Ser
    50                  55                  60

Pro Gly Thr Ser Ser Thr Gly Ser Pro Gly Thr Pro Gly Ser Gly Thr
65                  70                  75                  80

Ala Ser Ser Ser Pro Gly Ser Ser Thr Pro Ser Gly Ala Thr Gly Ser
                85                  90                  95

Pro Gly Thr Pro Gly Ser Gly Thr Ala Ser Ser Ser Pro Gly Ala Ser
            100                 105                 110

Pro Gly Thr Ser Ser Thr Gly Ser Pro Gly Ala Ser Pro Gly Thr Ser
        115                 120                 125

Ser Thr Gly Ser Pro Gly Thr Pro Gly Ser Gly Thr Ala Ser Ser Ser
    130                 135                 140

<210> SEQ ID NO 43
<211> LENGTH: 450
<212> TYPE: DNA
<213> ORGANISM: Artificial Sequence
<220> FEATURE:
<223> OTHER INFORMATION: XTEN AG144-1

<400> SEQUENCE: 43

```
ggcgcgccac ccgggtcgtc cccgtcggcg tccaccggaa cagggccagg gtcatccccg    60
tcagcgtcga ctgggacggg acccgggaca cccggttcgg ggactgcatc ctcctcgcct   120
ggttcgtcca ccccgtcagg agccacgggt tcgccgggaa gcagcccaag cgcatccact   180
ggtacagggc ctggggcttc accgggtact tcatccacgg ggtcaccggg aacgcccgga   240
tcggggacgg cttcctcatc accaggatcg tcaacaccct cgggcgcaac gggcagcccc   300
ggaacccctg gttcgggtac ggcgtcgtcg agccccggtg cgagcccggg aacaagctcg   360
acaggatcgc ctggggcgtc acccggcacg tcgagcacag gcagcccgg aaccccagga   420 tcgggaaccg cgtcgtcaag cgcctcgagc                                    450
```

<210> SEQ ID NO 44
<211> LENGTH: 144
<212> TYPE: PRT
<213> ORGANISM: Artificial Sequence
<220> FEATURE:
<223> OTHER INFORMATION: XTEN AG144-A

<400> SEQUENCE: 44

Gly Ala Ser Pro Gly Thr Ser Ser Thr Gly Ser Pro Gly Ser Ser Pro
1               5                   10                  15

Ser Ala Ser Thr Gly Thr Gly Pro Gly Ser Ser Pro Ser Ala Ser Thr
            20                  25                  30

Gly Thr Gly Pro Gly Thr Pro Gly Ser Gly Thr Ala Ser Ser Ser Pro
        35                  40                  45

Gly Ser Ser Thr Pro Ser Gly Ala Thr Gly Ser Pro Gly Ser Ser Pro
    50                  55                  60

Ser Ala Ser Thr Gly Thr Gly Pro Gly Ala Ser Pro Gly Thr Ser Ser
65                  70                  75                  80

Thr Gly Ser Pro Gly Thr Pro Gly Ser Gly Thr Ala Ser Ser Ser Pro
                85                  90                  95

Gly Ser Ser Thr Pro Ser Gly Ala Thr Gly Ser Pro Gly Thr Pro Gly
            100                 105                 110

Ser Gly Thr Ala Ser Ser Ser Pro Gly Ala Ser Pro Gly Thr Ser Ser
        115                 120                 125

Thr Gly Ser Pro Gly Ala Ser Pro Gly Thr Ser Ser Thr Gly Ser Pro
    130                 135                 140

<210> SEQ ID NO 45
<211> LENGTH: 450
<212> TYPE: DNA
<213> ORGANISM: Artificial Sequence
<220> FEATURE:
<223> OTHER INFORMATION: XTEN AG144-A

<400> SEQUENCE: 45

```
ggcgcgccag gtgcctcgcc gggaacatca tcaactggtt cacccgggtc atccccctcg    60
gcctcaaccg ggacgggtcc cggctcatcc cccagcgcca gcactggaac aggtcctggc   120
actcctggtt ccggtacggc atcgtcatcc ccgggaagct caacaccgtc cggagcgaca   180
ggatcacctg gctcgtcacc ttcggcgtca ctggaacgg ggccaggggc ctcacccgga   240
acgtcctcga ctgggtcgcc tggtacgccg ggatcaggaa cggcctcatc ctcgcctggg   300
tcctcaacgc cctcgggtgc gactggttcg ccgggaactc ctggctcggg acggcctcg   360 tcgtcgcctg gggcatcacc ggggacgagc tccacggggt ccctggagc gtcaccgggg   420 acctcctcga caggtagccc ggcctcgagc                                    450
```

<210> SEQ ID NO 46
<211> LENGTH: 144
<212> TYPE: PRT
<213> ORGANISM: Artificial Sequence
<220> FEATURE:
<223> OTHER INFORMATION: XTEN AG144-B

<400> SEQUENCE: 46

Gly Thr Pro Gly Ser Gly Thr Ala Ser Ser Pro Gly Ser Ser Thr
1               5                   10                  15

Pro Ser Gly Ala Thr Gly Ser Pro Gly Ala Ser Pro Gly Thr Ser Ser
                20                  25                  30

Thr Gly Ser Pro Gly Thr Pro Gly Ser Gly Thr Ala Ser Ser Ser Pro
            35                  40                  45

Gly Ser Ser Thr Pro Ser Gly Ala Thr Gly Ser Pro Gly Ser Ser Pro
    50                  55                  60

Ser Ala Ser Thr Gly Thr Gly Pro Gly Ser Ser Pro Ser Ala Ser Thr
65                  70                  75                  80

Gly Thr Gly Pro Gly Ser Ser Thr Pro Ser Gly Ala Thr Gly Ser Pro
                85                  90                  95

Gly Ser Ser Thr Pro Ser Gly Ala Thr Gly Ser Pro Gly Ala Ser Pro
            100                 105                 110

Gly Thr Ser Ser Thr Gly Ser Pro Gly Ala Ser Pro Gly Thr Ser Ser
        115                 120                 125

Thr Gly Ser Pro Gly Ala Ser Pro Gly Thr Ser Ser Thr Gly Ser Pro
    130                 135                 140

<210> SEQ ID NO 47
<211> LENGTH: 450
<212> TYPE: DNA
<213> ORGANISM: Artificial Sequence
<220> FEATURE:
<223> OTHER INFORMATION: XTEN AG144-B

<400> SEQUENCE: 47
ggcgcgccag gtacaccggg cagcggcacg gcttcgtcgt cacccggctc gtccacaccg        60
tcgggagcta cgggaagccc aggagcgtca ccgggaacgt cgtcaacggg gtcaccgggt       120
acgccaggta gcggcacggc cagcagctcg ccaggttcat cgaccccgtc gggagcgact       180
gggtcgcccg gatcaagccc gtcagcttcc actggaacag acccgggtc gtcgccgtca       240 gcctcaacgg ggacaggacc tggttcatcg acgccgtcag gggcgacagg ctcgcccgga       300
tcgtcaacac cctcggggc aacggggagc cctggtgcgt cgcctggaac ctcatccacc       360
ggaagcccgg gggcctcgcc gggtacgagc tccacgggat cgcccggagc gtcccccgga       420
acttcaagca cagggagccc tgcctcgagc                                        450

<210> SEQ ID NO 48
<211> LENGTH: 144
<212> TYPE: PRT
<213> ORGANISM: Artificial Sequence
<220> FEATURE:
<223> OTHER INFORMATION: XTEN AG144-C

<400> SEQUENCE: 48

Gly Thr Pro Gly Ser Gly Thr Ala Ser Ser Pro Gly Ala Ser Pro
1               5                   10                  15

Gly Thr Ser Ser Thr Gly Ser Pro Gly Ala Ser Pro Gly Thr Ser Ser
                20                  25                  30

Thr Gly Ser Pro Gly Ala Ser Pro Gly Thr Ser Ser Thr Gly Ser Pro
         35                  40                  45

Gly Ser Ser Pro Ser Ala Ser Thr Gly Thr Gly Pro Gly Thr Pro Gly
     50                  55                  60

Ser Gly Thr Ala Ser Ser Ser Pro Gly Ala Ser Pro Gly Thr Ser Ser
65                  70                  75                  80

Thr Gly Ser Pro Gly Ala Ser Pro Gly Thr Ser Ser Thr Gly Ser Pro
             85                  90                  95

Gly Ala Ser Pro Gly Thr Ser Ser Gly Ser Pro Gly Ser Ser Thr
                100                 105                 110

Pro Ser Gly Ala Thr Gly Ser Pro Gly Ser Ser Thr Pro Ser Gly Ala
            115                 120                 125

Thr Gly Ser Pro Gly Ala Ser Pro Gly Thr Ser Ser Thr Gly Ser Pro
            130                 135                 140

<210> SEQ ID NO 49
<211> LENGTH: 450
<212> TYPE: DNA
<213> ORGANISM: Artificial Sequence
<220> FEATURE:
<223> OTHER INFORMATION: XTEN AG144-C

<400> SEQUENCE: 49
ggcgcgccag gtacacccgg atcgggtaca gcgtcatcga gccccggtgc gtcacctggt      60
acgtcgagca cggggtcgcc aggggcgtcc cctgggacgt cctcaacagg ctcgcccggt     120
gcgtcacccg gcacgtcgtc cacgggttca cctggtagct ccccttccgc gtccactggc     180
accgggcctg gaactccggg gagcggcaca gcagagctcgt cgccgggagc atcgcctggg    240
acatcgagca ccgggtcgcc aggagcatcg cccggaacat ccagcacagg aagcccggc     300 gcgtcgcccg ggacatcaag cacaggttcc ccgggatcga gcacgccgtc cggagccact    360
ggatcaccag ggagctcgac accttccggc gcaacgggat cgcccggagc cagcccgggt    420
acgtcaagca ctggctcccc tgcctcgagc                                      450

<210> SEQ ID NO 50
<211> LENGTH: 144
<212> TYPE: PRT
<213> ORGANISM: Artificial Sequence
<220> FEATURE:
<223> OTHER INFORMATION: XTEN AG144-F

<400> SEQUENCE: 50

Gly Ser Ser Pro Ser Ala Ser Thr Gly Thr Gly Pro Gly Ser Ser Pro
1               5                   10                  15

Ser Ala Ser Thr Gly Thr Gly Pro Gly Ala Ser Pro Gly Thr Ser Ser
            20                  25                  30

Thr Gly Ser Pro Gly Ala Ser Pro Gly Thr Ser Ser Thr Gly Ser Pro
            35                  40                  45

Gly Ser Ser Thr Pro Ser Gly Ala Thr Gly Ser Pro Gly Ser Ser Pro
        50                  55                  60

Ser Ala Ser Thr Gly Thr Gly Pro Gly Ala Ser Pro Gly Thr Ser Ser
65                  70                  75                  80

Thr Gly Ser Pro Gly Ser Ser Pro Ser Ala Ser Thr Gly Thr Gly Pro
            85                  90                  95

Gly Thr Pro Gly Ser Gly Thr Ala Ser Ser Ser Pro Gly Ser Ser Thr
            100                 105                 110

Pro Ser Gly Ala Thr Gly Ser Pro Gly Ser Ser Thr Pro Ser Gly Ala

```
          115                 120                 125
Thr Gly Ser Pro Gly Ala Ser Pro Gly Thr Ser Thr Gly Ser Pro
    130                 135                 140

<210> SEQ ID NO 51
<211> LENGTH: 450
<212> TYPE: DNA
<213> ORGANISM: Artificial Sequence
<220> FEATURE:
<223> OTHER INFORMATION: XTEN AG144-F

<400> SEQUENCE: 51
ggcgcgccag gctccagccc ctccgcgagc acgggaaccg gaccaggttc gtcaccctca      60
gcatcaacgg ggacgggacc gggggcgtca ccaggaacgt cctccaccgg ctcgccgggt     120
gcatcacccg gaacgtcatc gaccggatcg ccagggagct cgacgccatc aggcgcaaca     180
ggatcacctg gctcaagccc tagcgcgtca accggcacgg gtccgggtgc ctcccctggc     240
acgtccagca ccggatcacc cggatcgagc ccatccgcct caaccggaac cggaccggt     300 acaccagggt cgggaacagc ctcctcgtca ccaggctcct caaccccctc gggagccacg     360
ggttcgcccg gttcgtcaac gccttccgga gcaactggta gccccggagc atcgccagga     420
acttcgagca cggggtcgcc cgcctcgagc                                      450

<210> SEQ ID NO 52
<211> LENGTH: 461
<212> TYPE: PRT
<213> ORGANISM: Homo sapiens

<400> SEQUENCE: 52

Met Gln Arg Val Asn Met Ile Met Ala Glu Ser Pro Gly Leu Ile Thr
1               5                   10                  15

Ile Cys Leu Leu Gly Tyr Leu Leu Ser Ala Glu Cys Thr Val Phe Leu
            20                  25                  30

Asp His Glu Asn Ala Asn Lys Ile Leu Asn Arg Pro Lys Arg Tyr Asn
        35                  40                  45

Ser Gly Lys Leu Glu Glu Phe Val Gln Gly Asn Leu Glu Arg Glu Cys
    50                  55                  60

Met Glu Glu Lys Cys Ser Phe Glu Glu Ala Arg Glu Val Phe Glu Asn
65                  70                  75                  80

Thr Glu Arg Thr Thr Glu Phe Trp Lys Gln Tyr Val Asp Gly Asp Gln
                85                  90                  95

Cys Glu Ser Asn Pro Cys Leu Asn Gly Gly Ser Cys Lys Asp Asp Ile
            100                 105                 110

Asn Ser Tyr Glu Cys Trp Cys Pro Phe Gly Phe Glu Gly Lys Asn Cys
        115                 120                 125

Glu Leu Asp Val Thr Cys Asn Ile Lys Asn Gly Arg Cys Glu Gln Phe
    130                 135                 140

Cys Lys Asn Ser Ala Asp Asn Lys Val Val Cys Ser Cys Thr Glu Gly
145                 150                 155                 160

Tyr Arg Leu Ala Glu Asn Gln Lys Ser Cys Glu Pro Ala Val Pro Phe
                165                 170                 175

Pro Cys Gly Arg Val Ser Val Ser Gln Thr Ser Lys Leu Thr Arg Ala
            180                 185                 190

Glu Thr Val Phe Pro Asp Val Asp Tyr Val Asn Ser Thr Glu Ala Glu
        195                 200                 205

Thr Ile Leu Asp Asn Ile Thr Gln Ser Thr Gln Ser Phe Asn Asp Phe
```

```
                    210                 215                 220
Thr Arg Val Val Gly Gly Glu Asp Ala Lys Pro Gly Gln Phe Pro Trp
225                 230                 235                 240

Gln Val Val Leu Asn Gly Lys Val Asp Ala Phe Cys Gly Gly Ser Ile
                245                 250                 255

Val Asn Glu Lys Trp Ile Val Thr Ala Ala His Cys Val Glu Thr Gly
                260                 265                 270

Val Lys Ile Thr Val Val Ala Gly Glu His Asn Ile Glu Glu Thr Glu
            275                 280                 285

His Thr Glu Gln Lys Arg Asn Val Ile Arg Ile Ile Pro His His Asn
    290                 295                 300

Tyr Asn Ala Ala Ile Asn Lys Tyr Asn His Asp Ile Ala Leu Leu Glu
305                 310                 315                 320

Leu Asp Glu Pro Leu Val Leu Asn Ser Tyr Val Thr Pro Ile Cys Ile
                325                 330                 335

Ala Asp Lys Glu Tyr Thr Asn Ile Phe Leu Lys Phe Gly Ser Gly Tyr
                340                 345                 350

Val Ser Gly Trp Gly Arg Val Phe His Lys Gly Arg Ser Ala Leu Val
            355                 360                 365

Leu Gln Tyr Leu Arg Val Pro Leu Val Asp Arg Ala Thr Cys Leu Arg
    370                 375                 380

Ser Thr Lys Phe Thr Ile Tyr Asn Asn Met Phe Cys Ala Gly Phe His
385                 390                 395                 400

Glu Gly Gly Arg Asp Ser Cys Gln Gly Asp Ser Gly Gly Pro His Val
                405                 410                 415

Thr Glu Val Glu Gly Thr Ser Phe Leu Thr Gly Ile Ile Ser Trp Gly
                420                 425                 430

Glu Glu Cys Ala Met Lys Gly Lys Tyr Gly Ile Tyr Thr Lys Val Ser
            435                 440                 445

Arg Tyr Val Asn Trp Ile Lys Glu Lys Thr Lys Leu Thr
    450                 455                 460

<210> SEQ ID NO 53
<211> LENGTH: 1386
<212> TYPE: DNA
<213> ORGANISM: Artificial Sequence
<220> FEATURE:
<223> OTHER INFORMATION: nucleotide sequence of factor IX variant, R338L

<400> SEQUENCE: 53
atgcagagag tcaacatgat tatggctgag tcacctgggc tgattactat ttgcctgctg      60
ggctacctgc tgtccgccga gtgtaccgtg ttcctggacc atgagaacgc aaataagatc     120
ctgaacaggc caaaagata caatagtggg aagctggaga aatttgtgca ggcaacctg      180 gagagagaat gcatggagga aaagtgtagc ttcgaggaag cccgcgaggt gtttgaaaat     240
acagagcgaa ccacagagtt ctggaagcag tatgtggacg gcgatcagtg cgagagcaac     300
ccctgtctga atggcggaag ttgcaaagac gatatcaact catacgaatg ctggtgtcct     360
ttcgggtttg aaggcaaaaa ttgcgagctg acgtgacat gtaacattaa gaatggacgg     420
tgcgagcagt tttgtaaaaa ctctgccgat aataaggtgg tgtgcagctg tactgaagga     480
tatcgcctgg ctgagaacca gaagtcctgc gaaccagcag tgcccttccc ttgtgggagg     540
gtgagcgtct cccagacttc aaaactgacc agagcagaga cagtgtttcc cgacgtggat     600
tacgtcaaca gcactgaggc cgaaaccatc ctggacaaca ttactcagtc tacccagagt     660
```

| | |
|---|---|
| ttcaatgact ttactcgggt ggtcgggggc gaggatgcta aaccaggcca gttcccctgg | 720 |
| caggtggtcc tgaacggaaa ggtggatgca ttttgcggag ggtctatcgt gaatgagaaa | 780 |
| tggattgtca ccgccgctca ctgcgtggaa accggagtca agatcacagt ggtcgctggg | 840 |
| gagcacaaca ttgaggaaac agaacatact gagcagaagc ggaatgtgat ccgcatcatt | 900 |
| cctcaccata actacaatgc agccatcaac aaatacaatc atgacattgc cctgctggaa | 960 |
| ctggatgagc tctggtgct gaacagctac gtcactccaa tctgcattgc tgacaaagag | 1020 |
| tataccaata tcttcctgaa gtttggatca gggtacgtga gcggctgggg aagagtcttc | 1080 |
| cacaagggca ggagcgccct ggtgctccag tatctgcgag tgcctctggt cgatcgagct | 1140 |
| acctgtctgc tgtctaccaa gtttacaatc tacaacaaca tgttctgcgc tgggtttcac | 1200 |
| gagggaggac gagactcctg tcagggcgat tctggggcc cacatgtgac agaggtcgaa | 1260 |
| ggcaccagct tcctgactgg catcatttcc tggggagagg aatgtgcaat gaagggaaaa | 1320 |
| tacgggatct acaccaaagt gagccgctat gtgaactgga tcaaggaaaa aaccaaactg | 1380 |
| acctaa | 1386 |

<210> SEQ ID NO 54
<211> LENGTH: 1386
<212> TYPE: DNA
<213> ORGANISM: Artificial Sequence
<220> FEATURE:
<223> OTHER INFORMATION: FIX-R338L-co2

<400> SEQUENCE: 54

| | |
|---|---|
| atgcagaggg tgaacatgat catggccgag agccccggcc tgatcaccat ctgcctgctg | 60 |
| ggctacctgc tgagcgccga gtgcaccgtg ttcctggacc acgagaacgc caacaagatc | 120 |
| ctgaacaggc caagaggta caacagcggc aagctggagg agttcgtgca gggcaacctg | 180 |
| gagagggagt gcatggagga gaagtgcagc ttcgaggagg ccagggaggt gttcgagaac | 240 |
| accgagagga ccaccgagtt ctggaagcag tacgtggacg gcgaccagtg cgagagcaac | 300 |
| ccctgcctga acggcggcag ctgcaaggac gacatcaaca gctacgagtg ctggtgcccc | 360 |
| ttcggcttcg agggcaagaa ctgcgagctg gacgtgacct gcaacatcaa gaacggcagg | 420 |
| tgcgagcagt tctgcaagaa cagcgccgac aacaaggtgg tgtgcagctg caccgagggc | 480 |
| tacaggctgg ccgagaacca gaagagctgc gagcccgccg tgcccttccc ctgcggcagg | 540 |
| gtgagcgtga gccagaccag caagctgacc agggccgaga ccgtgttccc cgacgtggac | 600 |
| tacgtgaaca gcaccgaggc cgagaccatc ctggacaaca tcacccagag cacccagagc | 660 |
| ttcaacgact tcaccagagt ggtggggggc gaggacgcca agcccggcca gttcccctgg | 720 |
| caggtcgtgc tgaatggcaa agtcgatgcc ttctgcgggg gcagcatcgt caacgagaag | 780 |
| tggattgtga ctgccgccca ttgcgtggaa accggggtga agatcactgt ggtggctggg | 840 |
| gagcacaaca tcgaggaaac cgagcacacc gagcagaaga ggaacgtgat caggattatc | 900 |
| ccccatcaca actacaatgc cgccatcaat aagtacaacc atgatattgc cctgctggag | 960 |
| ctggatgaac cctggtcct gaacagctat gtgactccca tctgcattgc cgacaaggag | 1020 |
| tataccaaca tcttcctgaa atttggcagc ggctatgtct ctggctgggg cagggtgttc | 1080 |
| cataagggga ggagcgccct ggtcctgcag tacctgagag tgcccctggt ggacagggcc | 1140 |
| acctgcctgc tgagcaccaa gttcaccatc tacaacaata tgttttgcgc tggcttccat | 1200 |
| gagggggca gggacagctg ccaggggac agcgggggcc cccatgtgac tgaggtggag | 1260 |
| ggcaccagct tcctgaccgg catcatcagc tggggggagg agtgcgccat gaaggggaag | 1320 |

```
<210> SEQ ID NO 55
<211> LENGTH: 1386
<212> TYPE: DNA
<213> ORGANISM: Artificial Sequence
<220> FEATURE:
<223> OTHER INFORMATION: FIX-R338L-co3

<400> SEQUENCE: 55
atgcagaggg tgaacatgat catggccgag agccccggcc tgatcaccat ctgcctgctg      60
ggctacctgc tgagcgccga gtgcaccgtg ttcctggacc acgagaacgc caacaagatc     120
ctgaacaggc caagaggta caacagcggc aagctggagg agttcgtgca gggcaacctg     180
gagagggagt gcatggagga aagtgcagc ttcgaggagg ccagggaggt gttcgagaac     240
accgagagga ccaccgagtt ctggaagcag tacgtggacg cgaccagtg cgagagcaac     300
ccctgcctga cggcggcag ctgcaaggac gacatcaaca gctacgagtg ctggtgcccc     360
ttcggcttcg agggcaagaa ctgcgagctg gacgtgacct gcaacatcaa gaacggcagg     420
tgcgagcagt tctgcaagaa cagcgccgac aacaaggtgg tgtgcagctg caccgagggc     480
tacaggctgg ccgagaacca gaagagctgc gagcccgccg tgcccttccc ctgcggcagg     540
gtgagcgtga gccagaccag caagctgacc agggccgaga ccgtgttccc cgacgtggac     600
tacgtgaaca gcaccgaggc cgagaccatc ctggacaaca tcacccagag cacccagagc     660
ttcaacgact caccagggt ggtgggcggc gaggacgcca agcccggcca gtttccctgg     720
caggtggtgc tgaacggcaa ggtggacgcc ttctgcggcg gcagcatcgt gaacgagaag     780
tggatcgtga ccgctgccca ttgcgtggaa accggcgtga agatcaccgt ggtggccggc     840
gagcacaaca tcgaagagac cgagcacacc gaacagaaaa ggaacgtgat caggatcatc     900
cctcaccata actacaatgc cgccattaac aagtacaatc acgacatcgc tctgctggaa     960
ctggatgaac ccctggtgct gaacagctac gtgacccta tctgcatcgc cgacaaggag    1020
tatactaaca tctttctgaa gtttggcagc ggctatgtga gcggctgggg cagggtgttc    1080
cacaaaggca ggagcgccct ggtgctgcag tacctgaggg tgcccctggt ggatagggct    1140
acctgcctgc tgagcaccaa gttcaccatc tacaacaaca tgttctgtgc cggcttccac    1200
gaaggcggca gggactcttg ccagggcgac agcggcggcc ccatgtgacg aggtggaa    1260
ggcactagct ttctgaccgg catcatcagc tggggcgagg agtgcgccat gaagggcaag    1320
tacggcatct acactaaggt gagcaggtac gtgaactgga tcaaagaaaa gaccaagctg    1380
acctaa                                                               1386

<210> SEQ ID NO 56
<211> LENGTH: 1386
<212> TYPE: DNA
<213> ORGANISM: Artificial Sequence
<220> FEATURE:
<223> OTHER INFORMATION: FIX-R338L-co4

<400> SEQUENCE: 56
atgcagaggg tgaacatgat catggccgag agccccggcc tgatcaccat ctgcctgctg      60
ggctacctgc tgagcgccga gtgcaccgtg ttcctggacc acgagaacgc caacaagatc     120
ctgaacaggc caagaggta caacagcggc aagctggagg agttcgtgca gggcaacctg     180
```

| | |
|---|---|
| gagagggagt gcatggagga gaagtgcagc ttcgaggagg ccagggaggt gttcgagaac | 240 |
| accgagagga ccaccgagtt ctggaagcag tacgtggacg gcgaccagtg cgagagcaac | 300 |
| ccctgcctga acggcggcag ctgcaaggac gacatcaaca gctacgagtg ctggtgcccc | 360 |
| ttcggcttcg agggcaagaa ctgcgagctg gacgtgacct gcaacatcaa gaacggcagg | 420 |
| tgcgagcagt tctgcaagaa cagcgccgac aacaaggtgg tgtgcagctg caccgagggc | 480 |
| tacaggctgg ccgagaacca gaagagctgc gagcccgccg tgcccttccc ctgcggcagg | 540 |
| gtgagcgtga gccagaccag caagctgacc agggccgaga ccgtgttccc cgacgtggac | 600 |
| tacgtgaaca gcaccgaggc cgagaccatc ctggacaaca tcacccagag cacccagagc | 660 |
| ttcaacgact tcaccagggt ggtgggcggc gaggacgcca agcccggcca gttcccctgg | 720 |
| caggtggtgc tgaacggcaa ggtggacgcc ttctgcggcg gcagcatcgt gaacgagaag | 780 |
| tggatcgtga ccgccgccca ctgcgtggag accggcgtga agatcaccgt ggtggccggc | 840 |
| gagcacaaca tcgaggagac cgagcacacc gagcagaaga ggaacgtgat caggatcatc | 900 |
| ccccaccaca actacaacgc cgccatcaac aagtacaacc acgacatcgc cctgctggag | 960 |
| ctggacgagc ccctggtgct gaacagctac gtgacccccca tctgcatcgc cgacaaggag | 1020 |
| tacaccaaca tcttcctgaa gttcggcagc ggctacgtga gcggctgggg cagggtgttc | 1080 |
| cacaagggca ggagcgccct ggtgctgcag tacctgaggg tgcccctggt ggacagggcc | 1140 |
| acctgcctgc tgagcaccaa gttcaccatc tacaacaaca tgttctgcgc cggcttccac | 1200 |
| gagggcggca gggacagctg ccagggcgac agcggcggcc ccacgtgac cgaggtggag | 1260 |
| ggcaccagct tcctgaccgg catcatcagc tggggcgagg agtgcgccat gaagggcaag | 1320 |
| tacggcatct acaccaaggt gagcaggtac gtgaactgga tcaaggagaa gaccaagctg | 1380 |
| acctaa | 1386 |

<210> SEQ ID NO 57
<211> LENGTH: 1386
<212> TYPE: DNA
<213> ORGANISM: Artificial Sequence
<220> FEATURE:
<223> OTHER INFORMATION: FIX-R338L-co5

<400> SEQUENCE: 57

| | |
|---|---|
| atgcagaggg tcaacatgat catggctgag tctcctggcc tgatcaccat ctgcctgctg | 60 |
| ggctatctgc tgtccgctga gtgcactgtc ttcctggacc acgagaacgc caacaagatc | 120 |
| ctgaacaggc caagaggta taactctggc aagctggagg agtttgtgca ggggaacctg | 180 |
| gagagggagt gcatggagga gaagtgcagc ttcgaggagg ccagggaggt gtttgagaac | 240 |
| actgagagga ccaccgagtt ctggaagcag tatgtggacg gggaccagtg cgagtctaac | 300 |
| ccttgcctga acggggggcag ctgcaaggat gacatcaaca gctatgagtg ctggtgccct | 360 |
| ttcggcttcg agggcaagaa ctgcgagctg gatgtgacct gcaacatcaa gaacggcagg | 420 |
| tgcgagcagt tctgcaagaa ctctgccgac aacaaggtgg tgtgcagctg cactgagggc | 480 |
| tataggctgg ctgagaacca gaagagctgt gagcctgctg tgcccttccc ctgcggcaga | 540 |
| gtgtctgtga ccagaccag caagctgacc agagctgaga ctgtcttccc cgacgtggac | 600 |
| tatgtgaaca gcaccgaggc tgagaccatc ctggacaaca tcacccagtc tacccagtct | 660 |
| ttcaacgact tcaccagagt ggtgggggc gaggacgcca agcctggcca gttcccctgg | 720 |
| caggtcgtgc tgaacggcaa agtggacgcc ttctgcgggg gcagcatcgt caacgagaag | 780 |
| tggatcgtga ctgctgctca ctgcgtggaa accggggtga agatcaccgt ggtggccggc | 840 |

-continued

| | |
|---|---:|
| gagcacaaca tcgaggagac cgagcacacc gagcagaaga ggaacgtgat caggatcatc | 900 |
| ccccaccaca actacaacgc cgccatcaac aagtacaacc acgacatcgc cctgctggag | 960 |
| ctggacgagc ccctggtgct gaacagctac gtgaccccca tctgcatcgc cgacaaggag | 1020 |
| tacaccaaca tcttcctgaa gttcggcagc ggctacgtga gcggctgggg cagggtgttc | 1080 |
| cacaagggca ggagcgccct ggtgctgcag tacctgaggg tgcccctggt ggacagggcc | 1140 |
| acctgcctgc tgagcaccaa gttcaccatc tacaacaaca tgttctgcgc cggcttccac | 1200 |
| gagggcggca gggacagctg ccagggcgac agcggcggcc cccacgtgac cgaggtggag | 1260 |
| ggcaccagct tcctgaccgg catcatcagc tggggcgagg agtgcgccat gaagggcaag | 1320 |
| tacggcatct acaccaaggt gagcaggtac gtgaactgga tcaaggagaa gaccaagctg | 1380 |
| acctaa | 1386 |

<210> SEQ ID NO 58
<211> LENGTH: 1386
<212> TYPE: DNA
<213> ORGANISM: Artificial Sequence
<220> FEATURE:
<223> OTHER INFORMATION: FIX-R338L-co6

<400> SEQUENCE: 58

| | |
|---|---:|
| atgcagaggg tcaacatgat catggctgag tctcctggcc tgatcactat ctgcctgctg | 60 |
| ggctacctgc tgagcgccga gtgcactgtc ttcctggacc acgagaacgc caacaagatc | 120 |
| ctgaacaggc ccaagagata caactctggc aagctggagg agtttgtgca ggggaacctg | 180 |
| gagagggagt gcatggagga aagtgcagc ttcgaggagg ccagggaggt gtttgagaac | 240 |
| actgagagga ccactgagtt ctggaagcag tatgtggacg gggaccagtg cgagtctaac | 300 |
| ccttgcctga acggggcag ctgcaaggat gacatcaaca gctacgagtg ctggtgccct | 360 |
| ttcggcttcg agggcaagaa ctgcgagctg gatgtgactt gcaacatcaa gaacggcagg | 420 |
| tgcgagcagt tctgcaagaa ctctgccgac aacaaagtcg tgtgcagctg cactgagggc | 480 |
| tacagactgg ctgagaacca gaagagctgt gagcctgctg tgccctttcc ctgcggcaga | 540 |
| gtgtctgtga gccagaccag caagctgacc agagccgaaa ccgtgttccc cgacgtggac | 600 |
| tatgtgaaca gcactgaggc tgagaccatc ctggacaaca tcactcagtc tacccagtct | 660 |
| ttcaacgact tcaccagagt ggtggggggc gaggacgcca agcctggcca gttcccctgg | 720 |
| caggtcgtgc tgaacggcaa ggtggacgcc ttctgcgggg gcagcatcgt caacgagaag | 780 |
| tggatcgtga ctgccgccca ctgcgtggag actggggtga agatcactgt ggtggctggg | 840 |
| gagcacaaca tcgaggaaac cgagcacact gagcagaaga ggaacgtgat caggattatc | 900 |
| ccccaccaca actacaacgc cgccatcaac aagtacaacc acgacatcgc cctgctggag | 960 |
| ctggatgaac ccctggtgct gaacagctac gtgaccccta tctgcatcgc cgacaaggag | 1020 |
| tacactaaca tcttcctgaa gttcggcagc ggctacgtga gcggctgggg cagggtgttc | 1080 |
| cacaagggca ggagcgccct ggtgctgcag tacctgaggg tgcccctggt ggacagggcc | 1140 |
| acctgcctgc tgagcaccaa gttcaccatc tacaacaaca tgttctgcgc cggcttccac | 1200 |
| gagggcggca gggacagctg ccagggcgac agcggcggcc cccacgtgac cgaggtggag | 1260 |
| ggcaccagct tcctgaccgg catcatcagc tggggcgagg agtgcgccat gaagggcaag | 1320 |
| tacggcatct acaccaaggt gagcaggtac gtgaactgga tcaaggagaa gaccaagctg | 1380 |
| acctaa | 1386 |

OPTIMIZED FACTOR IX GENE

REFERENCE TO SEQUENCE LISTING SUBMITTED ELECTRONICALLY

The content of the electronically submitted sequence listing (Name 2159_4510002_SequenceListing_ST25.txt; Size: 51,015 bytes; and Date of Creation: Dec. 30, 2016) was originally submitted in the International Application No. PCT/US2015/038678 and is incorporated herein by reference in its entirety.

BACKGROUND OF THE INVENTION

The blood coagulation pathway, in part, involves the formation of an enzymatic complex of Factor VIIIa (FVIIIa) and Factor IXa (FIXa) (Xase complex) on the surface of platelets. FIXa is a serine protease with relatively weak catalytic activity without its cofactor FVIIIa. The Xase complex cleaves Factor X (FX) into Factor Xa (FXa), which in turn interacts with Factor Va (FVa) to cleave prothrombin and generate thrombin.

In hemophilia, blood clotting is disturbed by a lack of certain plasma blood clotting factors. Hemophilia B (also known as Christmas disease) is one of the most common inherited bleeding disorders in the world. It is caused by a deficiency in Factor IX that may result from either the decreased synthesis of the Factor IX protein or a defective molecule with reduced activity. It results in decreased in vivo and in vitro blood clotting activity and requires extensive medical monitoring throughout the life of the affected individual. Without effective prophylaxis, recurrent haemarthroses lead to the development of progressive and disabling arthropathy and poor quality of life (Giangrande P., Expert Opin Pharmacother. 2005; 6:1517-24).

Treatment of hemophilia B occurs by replacement of the missing clotting factor by exogenous factor concentrates highly enriched in Factor IX. However, generating such a concentrate from blood is fraught with technical difficulties. Although purification of Factor IX from plasma (plasma derived Factor IX; pdFIX) almost exclusively yields active Factor IX, such purification of Factor IX from plasma is very difficult because Factor IX is only present in low concentration in plasma (5 µg/mL). Andersson, Thrombosis Research 7: 451 459 (1975). Further, purification from blood requires the removal or inactivation of infectious agents such as HIV and HCV. In addition, pdFIX has a short half-life and therefore requires frequent dosing, which contributes to reduced adherence to prophylactic treatment.

Recombinant factor IX (rFIX) is also available, but suffers from the same short half-life and need for frequent dosing (e.g., 2-3 times per week for prophylaxis) as pdFIX. In addition, there exists a need in the art for FIX sequences that express efficiently in heterologous systems.

SUMMARY OF THE INVENTION

The present invention provides an isolated nucleic acid molecule comprising a nucleotide sequence at least 85% identical to SEQ ID NO:1, wherein the nucleotide sequence encodes a polypeptide with Factor IX activity. In one embodiment, the invention provides an isolated nucleic acid molecule comprising a nucleotide sequence at least 90% identical to SEQ ID NO: 1. In another embodiment, the invention provides an isolated nucleic acid molecule comprising a nucleotide sequence at least 95%, at least 96%, at least 97%, at least 98%, at least 99%, or 100% identical to SEQ ID NO:1. In other embodiments, the invention provides an isolated nucleic acid molecule comprising SEQ ID NO:1. The present invention provides an isolated nucleic acid molecule comprising a nucleotide sequence at least 80% identical to SEQ ID NO: 54, 55, 56, 57, or 58, wherein the nucleotide sequence encodes a polypeptide with Factor IX activity. In another embodiment, the invention provides an isolated nucleic acid molecule comprising a nucleotide sequence at least 85%, at least 90%, at least 95%, at least 96%, at least 97%, at least 98%, at least 99%, or 100% identical to SEQ ID NO: 54, 55, 56, 57, or 58, wherein the nucleotide sequence encodes a polypeptide with Factor IX activity.

In some embodiments, the isolated nucleic acid molecule of the invention has a human codon adaptation index that is increased relative to SEQ ID NO:2. In other embodiments, the isolated nucleic acid molecule of the invention has a human codon adaptation index that is at least about 0.75, at least about 0.76, at least about 0.77, at least about 0.78, at least about 0.79, or at least about 0.80. In still other embodiments, the isolated nucleic acid molecule of the invention has a human codon adaptation index that is at least about 0.80, at least about 0.81, at least about 0.82, at least about 0.83, at least about 0.84, at least about 0.85, at least about 0.86, at least about 0.87, at least about 0.88, at least about 0.89, or at least about 0.90.

In certain embodiments, the isolated nucleic acid molecule of the invention contains a higher percentage of G/C nucleotides compared to the percentage of G/C nucleotides in SEQ ID NO:2. In other embodiments, the isolated nucleic acid molecule of the invention contains a percentage of G/C nucleotides that is at least about 42%, at least about 43%, at least about 44%, at least about 45%, at least about 46%, at least about 47%, at least about 48%, at least about 49%, at least about 50%, or at least about 51%.

In some embodiments, the isolated nucleic acid molecule of the invention contain the splice site GGTGAT (SEQ ID NO:4) or GGTAAG (SEQ ID NO:5).

In certain embodiments, the isolated nucleic acid molecule of the invention contains fewer destabilizing element ATTTA (SEQ ID NO:6) relative to SEQ ID NO:2. In other embodiments, the isolated nucleic acid molecule of the invention does not contain a destabilizing element sequence.

In certain embodiments, the isolated nucleic acid molecule of the invention contains less repeat sequences relative to SEQ ID NO:2. In some embodiments, the repeat sequences include direct repeat, inverted repeat, or dyad repeat sequences.

In certain embodiments, the isolated nucleic acid molecule of the invention contains less antiviral motifs, e.g., TGTGT, which is located at 802 bp downstream from the start site ATG (SEQ ID NO:11) relative to SEQ ID NO:2. In some embodiments, the isolated nucleic acid molecule of the invention does not contain an antiviral motif.

In other embodiments, the isolated nucleic acid molecule of the invention does not contain a poly-T sequence (SEQ ID NO:7). In yet other embodiments, the isolated nucleic acid molecule of the invention does not contain a poly-A sequence (SEQ ID NOs:8-10), or any combination thereof.

In one embodiment, the isolated nucleic acid molecule of the invention further comprises a heterologous nucleotide sequence. For example, the heterologous nucleotide sequence can encode a heterologous amino acid sequence that is a half-life extender. In some embodiments, the heterologous amino acid sequence is an immunoglobulin constant region or a portion thereof, transferrin, albumin, albumin-binding polypeptide, an XTEN sequence, Fc, the C-terminal peptide (CTP) of the β subunit of human chorionic gonadotropin, or a PAS sequence. In other embodiments, the heterologous amino acid sequence is an Fc region or an FcRn binding partner. In still other embodiments, the heterologous amino acid sequence is linked to the FIX amino acid sequence encoded by the nucleotide sequence.

In a particular embodiment, the isolated nucleic acid molecule of the invention encodes a monomer-dimer hybrid molecule comprising Factor IX.

In another embodiment, the isolated nucleic acid molecule of the invention is operatively linked to at least one transcription control sequence.

The present invention also provides a vector comprising the nucleic acid molecule of the invention.

The present invention also provides a host cell comprising the nucleic acid molecule of the invention. In some embodiments, the host cell is selected from the group consisting of: a CHO cell, a HEK293 cell, a BHK21 cell, a PER.C6 cell, a NS0 cell, and a CAP cell.

The present invention also provides a polypeptide encoded by the nucleic acid molecule of the invention or the vector of the invention or produced by the host cell of the invention.

The present invention also provides a method of producing a polypeptide with Factor IX activity, comprising: culturing the host cell of the invention under conditions whereby a polypeptide with Factor IX activity is produced; and, recovering the polypeptide with Factor IX activity. In other embodiments of the method of producing a polypeptide with Factor IX activity, the expression of the polypeptide with Factor IX activity is increased relative to a host cell cultured under the same conditions comprising a reference nucleotide sequence comprising SEQ ID NO: 2. In other embodiments of the method, the host cell is a CHO cell. In other embodiments of the method, the host cell is a HEK293 cell.

The present invention also provides a method of increasing expression of a polypeptide with Factor IX activity in a subject comprising administering the isolated nucleic acid molecule of the invention or the vector of the invention to a subject in need thereof, wherein the expression of the polypeptide with Factor IX activity is increased relative to a reference nucleic acid molecule comprising SEQ ID NO: 2 or the vector comprising the reference nucleic acid molecule.

The present invention also provides a method of increasing expression of a polypeptide with Factor IX activity comprising culturing the host cell of the invention under conditions whereby a polypeptide with Factor IX activity is expressed by the nucleic acid molecule, wherein the expression of the polypeptide with Factor IX activity is increased relative to a host cell cultured under the same conditions comprising a reference nucleic acid sequence comprising SEQ ID NO: 2.

The present invention also provides a method of improving yield of a polypeptide with Factor IX activity comprising culturing the host cell of the invention under conditions whereby a polypeptide with Factor IX activity is produced by the nucleic acid molecule, wherein the yield of the polypeptide with Factor IX activity is increased relative to a host cell cultured under the same conditions comprising a reference nucleic acid sequence comprising SEQ ID NO: 2.

The present invention also provides a method of treating a bleeding disorder comprising: administering to a subject in need thereof a nucleic acid molecule of the invention, a vector of the invention, or a polypeptide of the invention. In some embodiments of the method of treating a bleeding disorder, the bleeding disorder is characterized by a deficiency in Factor IX. In some embodiments, the bleeding disorder is hemophilia. In some embodiments, the bleeding disorder is hemophilia B.

In some embodiments of the method of treating a bleeding disorder, plasma Factor IX activity at 24 hours post administration is increased relative to a subject administered a reference nucleic acid molecule comprising SEQ ID NO: 2, a vector comprising the reference nucleic acid molecule, or a polypeptide encoded by the reference nucleic acid molecule.

EMBODIMENTS

E1. A nucleotide molecule encoding a FIX polypeptide, the molecule comprising a codon optimized nucleic acid sequence encoding a C-terminal portion of the FIX polypeptide ("C-terminal portion nucleotides") and a codon optimized nucleic acid sequence encoding an N-terminal portion of the FIX polypeptide ("N-terminal portion nucleotides"), wherein (a) a relative frequency of codon usage of the C-terminal portion nucleotides is between about 90% to about 100%, and (b) a relative frequency of codon usage of the N-terminal portion nucleotides is between about 40% to about 85%, and wherein the nucleotide molecule exhibits enhanced expression of the FIX polypeptide from a cell compared to a wild-type FIX nucleotide molecule.

E2. The nucleotide molecule of E1, wherein the relative frequency of codon usage of the C-terminal portion nucleotides is between about 95% to about 100%.

E3. The nucleotide molecule of E1 or E2, wherein the relative frequency of codon usage of the N-terminal portion nucleotides is between about 50% to about 80%.

E4. The nucleotide molecule of any one of E1 to E3, wherein the relative frequency of codon usage of the N-terminal portion nucleotides is between about 60% to about 75%.

E5. The nucleotide molecule of any one of claims E1 to E4, wherein the C-terminal portion nucleotides encode amino acids 1 to 150-300 corresponding to SEQ ID NO: 3 and the N terminal portion nucledotides encode amino acids 151-301 to 461 corresponding to SEQ ID NO: 3.

E6. A method of making a Factor IX nucleotide molecule comprising codon optimizing C terminal portion nucleotides and N terminal portion nucleotides, wherein a relative frequency of codon usage of the C-terminal portion nucleotides is between about E7. The method of E6, wherein the relative frequency of codon usage of the C-terminal portion nucleotides is between about 95% to about 100%.

E8. The method of E6 or E7, wherein the relative frequency of codon usage of the N-terminal portion nucleotides is between about 50% to about 80%.

E9. The method of any one of E6 to E8, wherein the relative frequency of codon usage of the N-terminal portion nucleotides is between about 60% to about 75%.

E10. The method of any one of claims E6 to E9, wherein the C-terminal portion nucleotides encode amino acids 1 to 150-300 corresponding to SEQ ID NO: 3 and the N terminal portion nucleotides encode amino acids 151-301 to 461 corresponding to SEQ ID NO: 3.

BRIEF DESCRIPTION OF THE DRAWINGS

FIG. 1 is the nucleotide sequence of the optimized human Factor IX (SEQ ID NO:1), described in Example 1.

FIG. 2A shows the relative frequency of codons in the original human FIX sequence (SEQ ID NO:2) before codon optimization. The human codon adaptation index (CAI) of the original human FIX sequence is 0.72. FIG. 2B shows the relative frequency of codons in the optimized human FIX sequence (SEQ ID NO:1). The human CAI of the resulting optimized sequence is 0.87. The X-axis indicates the relative position of the codons along the length of the human FIX nucleotide sequence. The Y-axis indicates the relative frequency of the codon at each position within the human genome.

FIGS. 3A-B show the frequency of optimal human codons in the optimized human FIX sequence (SEQ ID NO:1). FIG. 3A shows the frequency of optimal codons in the original human FIX sequence (SEQ ID NO:2) before codon optimization. FIG. 3B shows the frequency of optimal codons in the human FIX sequence after codon optimization (SEQ ID NO:1). The X-axis indicates codon frequency in the human genome. The Y-axis indicates the percentage of codons in the human FIX sequence that falls into each category delineated on the X-axis.

FIGS. 4A-B show the G/C content of the optimized human FIX sequence (SEQ ID NO:1). FIG. 4A shows the G/C content of the original human FIX sequence (SEQ ID NO:2) before codon optimization. The G/C content of the original human FIX sequence is 41.17%. FIG. 4B shows the G/C content of the human FIX
sequence after codon optimization (SEQ ID NO:1). The G/C content of the optimized human FIX sequence is 51.37%. The X-axis indicates the relative position of the codons along the length of the human FIX nucleotide sequence. The Y-axis indicates the percent G/C content.

FIG. 5 shows the alignment of the optimized human FIX nucleotide sequence (SEQ ID NO:1) and the original human FIX nucleotide sequence (SEQ ID NO:2). The optimized codons are underlined.

FIG. 6 shows the codon adaptation index (CAI) of wild type human FIX and codon optimized human FIX variants. The X-axis indicates the relative position of the codons along the length of the human FIX nucleotide sequence. The Y-axis indicates the relative frequency of the codon at each position within the human genome. Codon optimized human FIX variants have a relative frequency of about 40% to about 100% throughout the nucleotide sequence (e.g., FIX-R338L-co1 and FIX-R338L-co4). Some codon optimized human FIX variants have a lower relative frequency at the C-terminal half of the coding sequence as compared to the N-terminal half (e.g., FIX-R338L-co2 and FIX-R338L-co3). Some codon optimized human FIX variants have a lower relative frequency at the N-terminal half of the coding sequence as compared to the C-terminal half (e.g., FIX-R338L-c05 and FIX-R338L-co6).

DETAILED DESCRIPTION OF THE INVENTION

Figure 2:
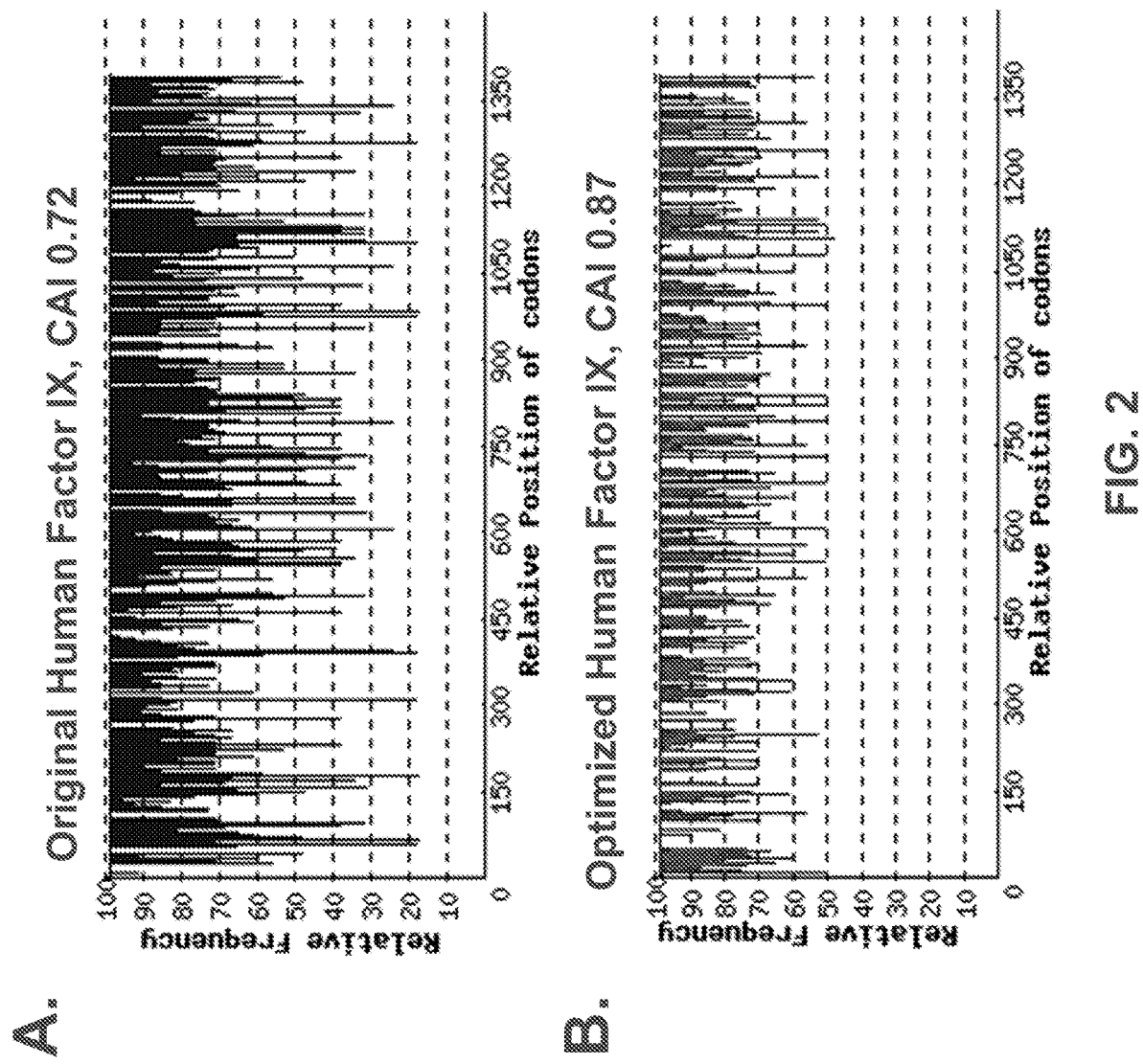
FIGS. 2A-B show the codon usage bias adjustment in the optimized human FIX sequence (SEQ ID NO:1).

Exemplary constructs of the invention are illustrated in the accompanying Figures and sequence listing. In order to provide a clear understanding of the specification and claims, the following definitions are provided below.

I. Definitions

It is to be noted that the term "a" or "an" entity refers to one or more of that entity: for example, "a nucleotide sequence" is understood to represent one or more nucleotide sequences. As such, the terms "a" (or "an"), "one or more," and "at least one" can be used interchangeably herein.

The term "about" is used herein to mean approximately, roughly, around, or in the regions of. When the term "about" is used in conjunction with a numerical range, it modifies that range by extending the boundaries above and below the numerical values set forth. In general, the term "about" is used herein to modify a numerical value above and below the stated value by a variance of 10 percent, up or down (higher or lower).

The term "isolated" for the purposes of the present invention designates a biological material (cell, nucleic acid or protein) that has been removed from its original environment (the environment in which it is naturally present). For example, a polynucleotide present in the natural state in a plant or an animal is not isolated, however the same polynucleotide separated from the adjacent nucleic acids in which it is naturally present, is considered "isolated." An "isolated" polypeptide, polynucleotide, a fragment thereof, a variant thereof, or a derivative thereof refers to a polypeptide or a polynucleotide that is not in its natural milieu. No particular level of purification is required. For example, an isolated polypeptide or polynucleotide can simply be removed from its native or natural environment. Recombinantly produced polypeptides and proteins expressed in host cells are considered isolated for the purpose of the invention, as are native or recombinant polypeptides which have been separated, fractionated, or partially or substantially purified by any suitable technique.

"Nucleic acid," "nucleic acid molecule," "oligonucleotide," and "polynucleotide" are used interchangeably and refer to the phosphate ester polymeric form of ribonucleosides (adenosine, guanosine, uridine or cytidine; "RNA molecules") or deoxyribonucleosides (deoxyadenosine, deoxyguanosine, deoxythymidine, or deoxycytidine; "DNA molecules"), or any phosphoester analogs thereof, such as phosphorothioates and thioesters, in either single stranded form, or a double-stranded helix. Double stranded DNA-DNA, DNA-RNA and RNA-RNA helices are possible. The term nucleic acid molecule, and in particular DNA or RNA molecule, refers only to the primary and secondary structure of the molecule, and does not limit it to any particular tertiary forms. Thus, this term includes double-stranded DNA found, inter alia, in linear or circular DNA molecules (e.g., restriction fragments), plasmids, supercoiled DNA and chromosomes. In discussing the structure of particular double-stranded DNA molecules, sequences can be described herein according to the normal convention of giving only the sequence in the 5' to 3' direction along the non-transcribed strand of DNA (i.e., the strand having a sequence homologous to the mRNA). A "recombinant DNA molecule" is a DNA molecule that has undergone a molecular biological manipulation. DNA includes, but is not limited to, cDNA, genomic DNA, plasmid DNA, synthetic DNA, and semi-synthetic DNA. A "nucleic acid composition" of the invention comprises one or more nucleic acids as described herein.

As used herein, a "coding region" or "coding sequence" is a portion of polynucleotide which consists of codons translatable into amino acids. Although a "stop codon" (TAG, TGA, or TAA) is typically not translated into an amino acid, it can be considered to be part of a coding region, but any flanking sequences, for example promoters, ribosome binding sites, transcriptional terminators, introns, and the like, are not part of a coding region. The boundaries of a coding region are typically determined by a start codon at the 5' terminus, encoding the amino terminus of the resultant polypeptide, and a translation stop codon at the 3' terminus, encoding the carboxyl terminus of the resulting polypeptide. Two or more coding regions can be present in a single polynucleotide construct, e.g., on a single vector, or in separate polynucleotide constructs, e.g., on separate (different) vectors. It follows, then, that a single vector can contain just a single coding region, or comprise two or more coding regions.

Certain proteins secreted by mammalian cells are associated with a secretory signal peptide which is cleaved from the mature protein once export of the growing protein chain across the rough endoplasmic reticulum has been initiated. Those of ordinary skill in the art are aware that signal peptides are generally fused to the N-terminus of the polypeptide, and are cleaved from the complete or "full-length" polypeptide to produce a secreted or "mature" form of the polypeptide. In certain embodiments, a native signal peptide or a functional derivative of that sequence that retains the ability to direct the secretion of the polypeptide is operably associated with it. Alternatively, a heterologous mammalian signal peptide, e.g., a human tissue plasminogen activator (TPA) or mouse 8-glucuronidase signal peptide, or a functional derivative thereof, can be used.

The term "downstream" refers to a nucleotide sequence that is located 3' to a reference nucleotide sequence. In certain embodiments, downstream nucleotide sequences relate to sequences that follow the starting point of transcription. For example, the translation initiation codon of a gene is located downstream of the start site of transcription.

The term "upstream" refers to a nucleotide sequence that is located 5' to a reference nucleotide sequence. In certain embodiments, upstream nucleotide sequences relate to sequences that are located on the 5' side of a coding region or starting point of transcription. For example, most promoters are located upstream of the start site of transcription.

As used herein, the term "regulatory region" refers to nucleotide sequences located upstream (5' non-coding sequences), within, or downstream (3' non-coding sequences) of a coding region, and which influence the transcription, RNA processing, stability, or translation of the associated coding region. Regulatory regions can include promoters, translation leader sequences, introns, polyadenylation recognition sequences, RNA processing sites, effector binding sites and stem-loop structures. If a coding region is intended for expression in a eukaryotic cell, a polyadenylation signal and transcription termination sequence will usually be located 3' to the coding sequence.

A polynucleotide which encodes a gene product, e.g., a polypeptide, can include a promoter and/or other transcription or translation control elements operably associated with one or more coding regions. In an operable association a coding region for a gene product, e.g., a polypeptide, is associated with one or more regulatory regions in such a way as to place expression of the gene product under the influence or control of the regulatory region(s). For example, a coding region and a promoter are "operably associated" if induction of promoter function results in the transcription of mRNA encoding the gene product encoded by the coding region, and if the nature of the linkage between the promoter and the coding region does not interfere with the ability of the promoter to direct the expression of the gene product or interfere with the ability of the DNA template to be transcribed. Other transcription control elements, besides a promoter, for example enhancers, operators, repressors, and transcription termination signals, can also be operably associated with a coding region to direct gene product expression.

"Transcriptional control sequences" refer to DNA regulatory sequences, such as promoters, enhancers, terminators, and the like, that provide for the expression of a coding sequence in a host cell. A variety of transcription control regions are known to those skilled in the art. These include, without limitation, transcription control regions which function in vertebrate cells, such as, but not limited to, promoter and enhancer segments from cytomegaloviruses (the immediate early promoter, in conjunction with intron-A), simian virus 40 (the early promoter), and retroviruses (such as Rous sarcoma virus). Other transcription control regions include those derived from vertebrate genes such as actin, heat shock protein, bovine growth hormone and rabbit 8-globin, as well as other sequences capable of controlling gene expression in eukaryotic cells. Additional suitable transcription control regions include tissue-specific promoters and enhancers as well as lymphokine-inducible promoters (e.g., promoters inducible by interferons or interleukins).

Similarly, a variety of translation control elements are known to those of ordinary skill in the art. These include, but are not limited to ribosome binding sites, translation initiation and termination codons, and elements derived from picornaviruses (particularly an internal ribosome entry site, or IRES, also referred to as a CITE sequence).

The term "expression" as used herein refers to a process by which a polynucleotide produces a gene product, for example, an RNA or a polypeptide. It includes without limitation transcription of the polynucleotide into messenger RNA (mRNA), transfer RNA (tRNA), small hairpin RNA (shRNA), small interfering RNA (siRNA) or any other RNA product, and the translation of an mRNA into a polypeptide. Expression produces a "gene product." As used herein, a gene product can be either a nucleic acid, e.g., a messenger RNA produced by transcription of a gene, or a polypeptide which is translated from a transcript. Gene products described herein further include nucleic acids with post transcriptional modifications, e.g., polyadenylation or splicing, or polypeptides with post translational modifications, e.g., methylation, glycosylation, the addition of lipids, association with other protein subunits, or proteolytic cleavage. The term "yield," as used herein, refers to the amount of a polypeptide produced by the expression of a gene.

A "vector" refers to any vehicle for the cloning of and/or transfer of a nucleic acid into a host cell. A vector can be a replicon to which another nucleic acid segment can be attached so as to bring about the replication of the attached segment. A "replicon" refers to any genetic element (e.g., plasmid, phage, cosmid, chromosome, or virus) that functions as an autonomous unit of replication in vivo, i.e., capable of replication under its own control. The term "vector" includes both viral and nonviral vehicles for introducing the nucleic acid into a cell in vitro, ex vivo or in vivo. A large number of vectors are known and used in the art including, for example, plasmids, modified eukaryotic viruses, or modified bacterial viruses. Insertion of a polynucleotide into a suitable vector can be accomplished by ligating the appropriate polynucleotide fragments into a chosen vector that has complementary cohesive termini.

Vectors can be engineered to encode selectable markers or reporters that provide for the selection or identification of cells that have incorporated the vector. Expression of selectable markers or reporters allows identification and/or selection of host cells that incorporate and express other coding regions contained on the vector. Examples of selectable marker genes known and used in the art include: genes providing resistance to ampicillin, streptomycin, gentamycin, kanamycin, hygromycin, bialaphos herbicide, sulfonamide, and the like; and genes that are used as phenotypic markers, i.e., anthocyanin regulatory genes, isopentanyl transferase gene, and the like. Examples of reporters known and used in the art include: luciferase (Luc), green fluorescent protein (GFP), chloramphenicol acetyltransferase (CAT), -galactosidase (LacZ), -glucuronidase (Gus), and the like. Selectable markers can also be considered to be reporters.

The term "selectable marker" refers to an identifying factor, usually an antibiotic or chemical resistance gene, that is able to be selected for based upon the marker gene's effect, i.e., resistance to an antibiotic, resistance to a herbicide, colorimetric markers, enzymes, fluorescent markers, and the like, wherein the effect is used to track the inheritance of a nucleic acid of interest and/or to identify a cell or organism that has inherited the nucleic acid of interest. Examples of selectable marker genes known and used in the art include: genes providing resistance to ampicillin, streptomycin, gentamycin, kanamycin, hygromycin, bialaphos herbicide, sulfonamide, and the like; and genes that are used as phenotypic markers, i.e., anthocyanin regulatory genes, isopentanyl transferase gene, and the like.

The term "reporter gene" refers to a nucleic acid encoding an identifying factor that is able to be identified based upon the reporter gene's effect, wherein the effect is used to track the inheritance of a nucleic acid of interest, to identify a cell or organism that has inherited the nucleic acid of interest, and/or to measure gene expression induction or transcription. Examples of reporter genes known and used in the art include: luciferase (Luc), green fluorescent protein (GFP), chloramphenicol acetyltransferase (CAT), β-galactosidase (LacZ), β-glucuronidase (Gus), and the like. Selectable marker genes can also be considered reporter genes.

"Promoter" and "promoter sequence" are used interchangeably and refer to a DNA sequence capable of controlling the expression of a coding sequence or functional RNA. In general, a coding sequence is located 3' to a promoter sequence. Promoters can be derived in their entirety from a native gene, or be composed of different elements derived from different promoters found in nature, or even comprise synthetic DNA segments. It is understood by those skilled in the art that different promoters can direct the expression of a gene in different tissues or cell types, or at different stages of development, or in response to different environmental or physiological conditions. Promoters that cause a gene to be expressed in most cell types at most times are commonly referred to as "constitutive promoters." Promoters that cause a gene to be expressed in a specific cell type are commonly referred to as "cell-specific promoters" or "tissue-specific promoters." Promoters that cause a gene to be expressed at a specific stage of development or cell differentiation are commonly referred to as "developmentally-specific promoters" or "cell differentiation-specific promoters." Promoters that are induced and cause a gene to be expressed following exposure or treatment of the cell with an agent, biological molecule, chemical, ligand, light, or the like that induces the promoter are commonly referred to as "inducible promoters" or "regulatable promoters." It is further recognized that since in most cases the exact boundaries of regulatory sequences have not been completely defined, DNA fragments of different lengths can have identical promoter activity.

The promoter sequence is typically bounded at its 3' terminus by the transcription initiation site and extends upstream (5' direction) to include the minimum number of bases or elements necessary to initiate transcription at levels detectable above background. Within the promoter sequence will be found a transcription initiation site (conveniently defined for example, by mapping with nuclease S1), as well as protein binding domains (consensus sequences) responsible for the binding of RNA polymerase.

The terms "restriction endonuclease" and "restriction enzyme" are used interchangeably and refer to an enzyme that binds and cuts within a specific nucleotide sequence within double stranded DNA.

The term "plasmid" refers to an extra-chromosomal element often carrying a gene that is not part of the central metabolism of the cell, and usually in the form of circular double-stranded DNA molecules. Such elements can be autonomously replicating sequences, genome integrating sequences, phage or nucleotide sequences, linear, circular, or supercoiled, of a single- or double-stranded DNA or RNA, derived from any source, in which a number of nucleotide sequences have been joined or recombined into a unique construction which is capable of introducing a promoter fragment and DNA sequence for a selected gene product along with appropriate 3' untranslated sequence into a cell.

Eukaryotic viral vectors that can be used include, but are not limited to, adenovirus vectors, retrovirus vectors, adeno-associated virus vectors, poxvirus, e.g., vaccinia virus vectors, baculovirus vectors, or herpesvirus vectors. Non-viral vectors include plasmids, liposomes, electrically charged lipids (cytofectins), DNA-protein complexes, and biopolymers.

A "cloning vector" refers to a "replicon," which is a unit length of a nucleic acid that replicates sequentially and which comprises an origin of replication, such as a plasmid, phage or cosmid, to which another nucleic acid segment can be attached so as to bring about the replication of the attached segment. Certain cloning vectors are capable of replication in one cell type, e.g., bacteria and expression in another, e.g., eukaryotic cells. Cloning vectors typically comprise one or more sequences that can be used for selection of cells comprising the vector and/or one or more multiple cloning sites for insertion of nucleic acid sequences of interest.

The term "expression vector" refers to a vehicle designed to enable the expression of an inserted nucleic acid sequence following insertion into a host cell. The inserted nucleic acid sequence is placed in operable association with regulatory regions as described above.

Vectors are introduced into host cells by methods well known in the art, e.g., transfection, electroporation, microinjection, transduction, cell fusion, DEAE dextran, calcium phosphate precipitation, lipofection (lysosome fusion), use of a gene gun, or a DNA vector transporter.

"Culture," "to culture" and "culturing," as used herein, means to incubate cells under in vitro conditions that allow for cell growth or division or to maintain cells in a living state. "Cultured cells," as used herein, means cells that are propagated in vitro.

As used herein, the term "polypeptide" is intended to encompass a singular "polypeptide" as well as plural "polypeptides," and refers to a molecule composed of monomers (amino acids) linearly linked by amide bonds (also known as peptide bonds). The term "polypeptide" refers to any chain or chains of two or more amino acids, and does not refer to a specific length of the product. Thus, peptides, dipeptides, tripeptides, oligopeptides, "protein," "amino acid chain," or any other term used to refer to a chain or chains of two or more amino acids, are included within the definition of "polypeptide," and the term "polypeptide" can be used instead of, or interchangeably with any of these terms. The term "polypeptide" is also intended to refer to the products of post-expression modifications of the polypeptide, including without limitation glycosylation, acetylation, phosphorylation, amidation, derivatization by known protecting/blocking groups, proteolytic cleavage, or modification by non-naturally occurring amino acids. A polypeptide can be derived from a natural biological source or produced recombinant technology, but is not necessarily translated from a designated nucleic acid sequence. It can be generated in any manner, including by chemical synthesis.

The term "amino acid" includes alanine (Ala or A); arginine (Arg or R); asparagine (Asn or N); aspartic acid (Asp or D); cysteine (Cys or C); glutamine (Gin or Q); glutamic acid (Glu or E); glycine (Gly or G); histidine (His or H); isoleucine (Ile or I): leucine (Leu or L); lysine (Lys or K); methionine (Met or M); phenylalanine (Phe or F); proline (Pro or P); serine (Ser or S); threonine (Thr or T); tryptophan (Trp or W); tyrosine (Tyr or Y); and valine (Val or V). Non-traditional amino acids are also within the scope of the invention and include norleucine, ornithine, norvaline, homoserine, and other amino acid residue analogues such as those described in Ellman et al. Meth. Enzym. 202:301-336 (1991). To generate such non-naturally occurring amino acid residues, the procedures of Noren et al. Science 244:182 (1989) and Ellman et al., supra, can be used. Briefly, these procedures involve chemically activating a suppressor tRNA with a non-naturally occurring amino acid residue followed by in vitro transcription and translation of the RNA. Introduction of the non-traditional amino acid can also be achieved using peptide chemistries known in the art.

As used herein, the term "polar amino acid" includes amino acids that have net zero charge, but have non-zero partial charges in different portions of their side chains (e.g., M, F, W, S, Y, N, Q, or C). These amino acids can participate in hydrophobic interactions and electrostatic interactions. As used herein, the term "charged amino acid" includes amino acids that can have non-zero net charge on their side chains (e.g., R, K, H, E, or D). These amino acids can participate in hydrophobic interactions and electrostatic interactions.

Also included in the present invention are fragments or variants of polypeptides, polynucleotides, and any combination thereof. The term "fragment" or "variant" when referring to polypeptide binding domains or binding molecules of the present invention include any polypeptides which retain at least some of the properties (e.g., FcRn binding affinity for an FcRn binding domain or Fc variant or coagulation activity for an FIX variant) of the reference polypeptide. Fragments of polypeptides include proteolytic fragments, as well as deletion fragments, in addition to functional fragments discussed elsewhere herein, but do not include the naturally occurring full-length polypeptide (or mature polypeptide). Variants of polypeptide binding domains or binding molecules of the present invention include fragments as described above, and also polypeptides with altered amino acid sequences due to amino acid substitutions, deletions, or insertions. Variants can be naturally or non-naturally occurring. Non-naturally occurring variants can be produced using art-known mutagenesis techniques. Variant polypeptides can comprise conservative or non-conservative amino acid substitutions, deletions or additions.

A "conservative amino acid substitution" is one in which the amino acid residue is replaced with an amino acid residue having a similar side chain. Families of amino acid residues having similar side chains have been defined in the art, including basic side chains (e.g., lysine, arginine, or histidine), acidic side chains (e.g., aspartic acid, or glutamic acid), uncharged polar side chains (e.g., glycine, asparagine, glutamine, serine, threonine, tyrosine, or cysteine), nonpolar side chains (e.g., alanine, valine, leucine, isoleucine, proline, phenylalanine, methionine, or tryptophan), beta-branched side chains (e.g., threonine, valine, or isoleucine) and aromatic side chains (e.g., tyrosine, phenylalanine, tryptophan, or histidine). Thus, if an amino acid in a polypeptide is replaced with another amino acid from the same side chain family, the substitution is considered to be conservative. In another embodiment, a string of amino acids can be conservatively replaced with a structurally similar string that differs in order and/or composition of side chain family members.

The term "percent identity" as known in the art, is a relationship between two or more polypeptide sequences or two or more polynucleotide sequences, as determined by comparing the sequences. It may be specified that percent identity is determined by comparing the length of (full length of) the two or more sequences. In the art, "identity" also means the degree of sequence relatedness between polypeptide or polynucleotide sequences, as the case can be, as determined by the match between strings of such sequences. "Identity" can be readily calculated by known methods, including but not limited to those described in: *Computational Molecular Biology* (Lesk, A. M., ed.) Oxford University Press, New York (1988); *Biocomputing: Informatics and Genome Projects* (Smith, D. W., ed.) Academic Press, New York (1993); *Computer Analysis of Sequence Data, Part I* (Griffin, A. M., and Griffin, H. G., eds.) Humana Press, New Jersey (1994); *Sequence Analysis in Molecular*

Biology (von Heinje, G., ed.) Academic Press (1987); and Sequence Analysis Primer (Gribskov, M. and Devereux, J., eds.) Stockton Press, New York (1991). Preferred methods to determine identity are designed to give the best match between the sequences tested. Methods to determine identity are codified in publicly available computer programs. Sequence alignments and percent identity calculations can be performed using sequence analysis software such as the Megalign program of the LASERGENE bioinformatics computing suite (DNASTAR Inc., Madison, Wis.), the GCG suite of programs (Wisconsin Package Version 9.0, Genetics Computer Group (GCG), Madison, Wis.), BLASTP, BLASTN, BLASTX (Altschul et al., *J. Mol. Biol.* 215:403 (1990)), and DNASTAR (DNASTAR, Inc. 1228 S. Park St. Madison, Wis. 53715 USA). Within the context of this application it will be understood that where sequence analysis software is used for analysis, that the results of the analysis will be based on the "default values" of the program referenced, unless otherwise specified. As used herein "default values" will mean any set of values or parameters which originally load with the software when first initialized. For the purposes of determining percent identity between an optimized FIX sequence of the invention and a reference sequence, only nucleotides in the reference sequence corresponding to nucleotides in the optimized FIX sequence of the invention are used to calculate percent identity.

The term "N-terminal portion" of FIX polypeptide includes any N terminal sequence of the FIX polypeptide comprising at least about 100 amino acids, 150 amino acids, 200 amino acids, or 250 amino acids at the N terminal region. For example, N-terminal portion can include amino acids 1 to 150-300 corresponding to SEQ ID NO: 3. The term "C-terminal portion" of FIX polypeptide can include any C terminal sequence of FIX polypeptide comprising at least about 100 amino acids, 150 amino acids, 200 amino acids, or 250 amino acids at the C terminal region. The N terminal region and the C terminal region together have a FIX polypeptide activity. In one embodiment, the N terminal region and the C terminal region together can form a full length FIX polypeptide.

As used herein, "amino acids 1 to 150-300 corresponding to SEQ ID NO: 3" means a range of amino acid sequences that can be selected from: amino acids 1 to 150, amino acids 1 to 151, amino acids 1 to 152, amino acids 1 to 153, amino acids 1 to 154, amino acids 1 to 155, amino acids 1 to 156, amino acids 1 to 157 . . . amino acids 1 to 298, amino acids 1 to 299, or amino acids 1 to 300 corresponding to SEQ ID NO: 3. Similarly, "amino acids 151-301 to 461 corresponding to SEQ ID NO: 3" means a range of amino acid sequences that can be selected from: amino acids 151 to 461, amino acids 152 to 461, amino acids 153 to 146, amino acids 154 to 461, amino acids 155 to 461, amino acids 156 to 461, amino acids 157 to 461, amino acids 158 to 461 . . . amino acids 299 to 461, amino acids 300 to 461, or amino acids 301 to 461 corresponding to SEQ ID NO: 3.

As used herein, "nucleotides corresponding to nucleotides in the optimized FIX sequence of the invention" are identified by alignment of the optimized FIX sequence of the invention to maximize the identity to the reference FIX sequence. The number used to identify an equivalent amino acid in a reference FIX sequence is based on the number used to identify the corresponding amino acid in the optimized FIX sequence of the invention.

A "fusion" or "chimeric" protein comprises a first amino acid sequence linked to a second amino acid sequence with which it is not naturally linked in nature. The amino acid sequences which normally exist in separate proteins can be brought together in the fusion polypeptide, or the amino acid sequences which normally exist in the same protein can be placed in a new arrangement in the fusion polypeptide, e.g., fusion of a FIX domain of the invention with an Ig Fc domain. A fusion protein is created, for example, by chemical synthesis, or by creating and translating a polynucleotide in which the peptide regions are encoded in the desired relationship. A chimeric protein can further comprises a second amino acid sequence associated with the first amino acid sequence by a covalent, non-peptide bond or a non-covalent bond.

As used herein, the term "half-life" refers to a biological half-life of a particular polypeptide in vivo. Half-life can be represented by the time required for half the quantity administered to a subject to be cleared from the circulation and/or other tissues in the animal. When a clearance curve of a given polypeptide is constructed as a function of time, the curve is usually biphasic with a rapid α-phase and longer β-phase. The α-phase typically represents an equilibration of the administered Fc polypeptide between the intra- and extra-vascular space and is, in part, determined by the size of the polypeptide. The β-phase typically represents the catabolism of the polypeptide in the intravascular space. In some embodiments, FIX and chimeric proteins comprising FIX are monophasic, and thus do not have an alpha phase, but just the single beta phase. Therefore, in certain embodiments, the term half-life as used herein refers to the half-life of the polypeptide in the β-phase.

The term "linked" as used herein refers to a first amino acid sequence or nucleotide sequence covalently or non-covalently joined to a second amino acid sequence or nucleotide sequence, respectively. The first amino acid or nucleotide sequence can be directly joined or juxtaposed to the second amino acid or nucleotide sequence or alternatively an intervening sequence can covalently join the first sequence to the second sequence. The term "linked" means not only a fusion of a first amino acid sequence to a second amino acid sequence at the C-terminus or the N-terminus, but also includes insertion of the whole first amino acid sequence (or the second amino acid sequence) into any two amino acids in the second amino acid sequence (or the first amino acid sequence, respectively). In one embodiment, the first amino acid sequence can be linked to a second amino acid sequence by a peptide bond or a linker. The first nucleotide sequence can be linked to a second nucleotide sequence by a phosphodiester bond or a linker. The linker can be a peptide or a polypeptide (for polypeptide chains) or a nucleotide or a nucleotide chain (for nucleotide chains) or any chemical moiety (for both polypeptide and polynucleotide chains). The term "linked" is also indicated by a hyphen (-).

As used herein the term "associated with" refers to a covalent or non-covalent bond formed between a first amino acid chain and a second amino acid chain. In one embodiment, the term "associated with" means a covalent, non-peptide bond or a non-covalent bond. This association can be indicated by a colon, i.e., (:). In another embodiment, it means a covalent bond except a peptide bond. For example, the amino acid cysteine comprises a thiol group that can form a disulfide bond or bridge with a thiol group on a second cysteine residue. In most naturally occurring IgG molecules, the CH1 and CL regions are associated by a disulfide bond and the two heavy chains are associated by two disulfide bonds at positions corresponding to 239 and 242 using the Kabat numbering system (position 226 or 229, EU numbering system). Examples of covalent bonds include, but are not limited to, a peptide bond, a metal bond, a hydrogen bond, a disulfide bond, a sigma bond, a pi bond, a delta bond, a glycosidic bond, an agnostic bond, a bent bond, a dipolar bond, a Pi backbond, a double bond, a triple bond, a quadruple bond, a quintuple bond, a sextuple bond, conjugation, hyperconjugation, aromaticity, hapticity, or antibonding. Non-limiting examples of non-covalent bond include an ionic bond (e.g., cation-pi bond or salt bond), a metal bond, an hydrogen bond (e.g., dihydrogen bond, dihydrogen complex, low-barrier hydrogen bond, or symmetric hydrogen bond), van der Walls force, London dispersion force, a mechanical bond, a halogen bond, aurophilicity, intercalation, stacking, entropic force, or chemical polarity.

The term "monomer-dimer hybrid" used herein refers to a chimeric protein comprising a first polypeptide chain and a second polypeptide chain, which are associated with each other by a disulfide bond, wherein the first chain comprises a clotting factor, e.g., Factor IX, and a first Fc region and the second chain comprises, consists essentially of, or consists of a second Fc region without the clotting factor. The monomer-dimer hybrid construct thus is a hybrid comprising a monomer aspect having only one clotting factor and a dimer aspect having two Fc regions.

Hemostasis, as used herein, means the stopping or slowing of bleeding or hemorrhage; or the stopping or slowing of blood flow through a blood vessel or body part.

Hemostatic disorder, as used herein, means a genetically inherited or acquired condition characterized by a tendency to hemorrhage, either spontaneously or as a result of trauma, due to an impaired ability or inability to form a fibrin clot. Examples of such disorders include the hemophilias. The three main forms are hemophilia A (factor VIII deficiency), hemophilia B (factor IX deficiency or "Christmas disease") and hemophilia C (factor XI deficiency, mild bleeding tendency). Other hemostatic disorders include, e.g., von Willebrand disease, Factor XI deficiency (PTA deficiency), Factor XII deficiency, deficiencies or structural abnormalities in fibrinogen, prothrombin, Factor V, Factor VII, Factor X or factor XIII, Bernard-Soulier syndrome, which is a defect or deficiency in GPIb. GPIb, the receptor for vWF, can be defective and lead to lack of primary clot formation (primary hemostasis) and increased bleeding tendency), and thrombasthenia of Glanzman and Naegeli (Glanzmann thrombasthenia). In liver failure (acute and chronic forms), there is insufficient production of coagulation factors by the liver; this can increase bleeding risk.

The isolated nucleic acid molecules or polypeptides of the invention can be used prophylactically. As used herein the term "prophylactic treatment" refers to the administration of a molecule prior to a bleeding episode. In one embodiment, the subject in need of a general hemostatic agent is undergoing, or is about to undergo, surgery. The chimeric protein of the invention can be administered prior to or after surgery as a prophylactic. The chimeric protein of the invention can be administered during or after surgery to control an acute bleeding episode. The surgery can include, but is not limited to, liver transplantation, liver resection, dental procedures, or stem cell transplantation.

The isolated nucleic acid molecules and polypeptides of the invention are also used for on-demand treatment. The term "on-demand treatment" refers to the administration of an isolated nucleic acid molecule or polypeptide in response to symptoms of a bleeding episode or before an activity that can cause bleeding. In one aspect, the on-demand treatment can be given to a subject when bleeding starts, such as after an injury, or when bleeding is expected, such as before surgery. In another aspect, the on-demand treatment can be given prior to activities that increase the risk of bleeding, such as contact sports.

As used herein the term "acute bleeding" refers to a bleeding episode regardless of the underlying cause. For example, a subject can have trauma, uremia, a hereditary bleeding disorder (e.g., factor VII deficiency) a platelet disorder, or resistance owing to the development of antibodies to clotting factors.

Treat, treatment, treating, as used herein refers to, e.g., the reduction in severity of a disease or condition; the reduction in the duration of a disease course; the amelioration of one or more symptoms associated with a disease or condition; the provision of beneficial effects to a subject with a disease or condition, without necessarily curing the disease or condition, or the prophylaxis of one or more symptoms associated with a disease or condition. In one embodiment, the term "treating" or "treatment" means maintaining an FIX trough level at least about 1 IU/dL, 2 IU/dL, 3 IU/dL, 4 IU/dL, 5 IU/dL, 6 IU/dL, 7 IU/dL, 8 IU/dL, 9 IU/dL, 10 IU/dL, 11 IU/dL, 12 IU/dL, 13 IU/dL, 14 IU/dL, 15 IU/dL, 16 IU/dL, 17 IU/dL, 18 IU/dL, 19 IU/dL, or 20 IU/dL in a subject by administering an isolated nucleic acid molecule or polypeptide of the invention. In another embodiment, treating or treatment means maintaining a FIX trough level between about 1 and about 20 IU/dL, about 2 and about 20 IU/dL, about 3 and about 20 IU/dL, about 4 and about 20 IU/dL, about 5 and about 20 IU/dL, about 6 and about 20 IU/dL, about 7 and about 20 IU/dL, about 8 and about 20 IU/dL, about 9 and about 20 IU/dL, or about 10 and about 20 IU/dL. Treatment or treating of a disease or condition can also include maintaining FIX activity in a subject at a level comparable to at least about 1%, 2%, 3%, 4%, 5%, 6%, 7%, 8%, 9%, 10%, 11%, 12%, 13%, 14%, 15%, 16%, 17%, 18%, 19%, or 20% of the FIX activity in a non-hemophiliac subject. The minimum trough level required for treatment can be measured by one or more known methods and can be adjusted (increased or decreased) for each person.

"Administering," as used herein, means to give a pharmaceutically acceptable Factor IX polypeptide of the invention to a subject via a pharmaceutically acceptable route. Routes of administration can be intravenous, e.g., intravenous injection and intravenous infusion. Additional routes of administration include, e.g., subcutaneous, intramuscular, oral, nasal, and pulmonary administration. Chimeric polypeptides and hybrid proteins can be administered as part of a pharmaceutical composition comprising at least one excipient.

As used herein, the phrase "subject in need thereof" includes subjects, such as mammalian subjects, that would benefit from administration of a nucleic acid molecule or a polypeptide of the invention, e.g., to improve hemostasis. In one embodiment, the subjects include, but are not limited to, individuals with hemophilia. In another embodiment, the subjects include, but are not limited to, the individuals who have developed an FIX inhibitor and thus are in need of a bypass therapy. The subject can be an adult or a minor (e.g., under 12 years old).

As used herein, the term "clotting factor," refers to molecules, or analogs thereof, naturally occurring or recombinantly produced which prevent or decrease the duration of a bleeding episode in a subject. In other words, it means molecules having pro-clotting activity, i.e., are responsible for the conversion of fibrinogen into a mesh of insoluble fibrin causing the blood to coagulate or clot. An "activatable clotting factor" is a clotting factor in an inactive form (e.g., in its zymogen form) that is capable of being converted to an active form.

Clotting activity, as used herein, means the ability to participate in a cascade of biochemical reactions that culminates in the formation of a fibrin clot and/or reduces the severity, duration or frequency of hemorrhage or bleeding episode.

As used herein the terms "heterologous" or "exogenous" refer to such molecules that are not normally found in a given context, e.g., in a cell or in a polypeptide. For example, an exogenous or heterologous molecule can be introduced into a cell and are only present after manipulation of the cell, e.g., by transfection or other forms of genetic engineering or a heterologous amino acid sequence can be present in a protein in which it is not naturally found.

As used herein, the term "heterologous nucleotide sequence" refers to a nucleotide sequence that does not naturally occur with a given polynucleotide sequence. In one embodiment, the heterologous nucleotide sequence encodes a polypeptide capable of extending the half-life of FIX. In another embodiment, the heterologous nucleotide sequence encodes a polypeptide that increases the hydrodynamic radius of FIX. In other embodiments, the heterologous nucleotide sequence encodes a polypeptide that improves one or more pharmacokinetic properties of FIX without significantly affecting its biological activity or function (e.g., its procoagulant activity). In some embodiments, FIX is linked or connected to the polypeptide encoded by the heterologous nucleotide sequence by a linker. Non-limiting examples of polypeptide moieties encoded by heterologous nucleotide sequences include an immunoglobulin constant region or a portion thereof, albumin or a fragment thereof, an albumin-binding moiety, a transferrin, the PAS polypeptides of U.S. Pat Application No. 20100292130, a HAP sequence, transferrin or a fragment thereof, the C-terminal peptide (CTP) of the β subunit of human chorionic gonadotropin, albumin-binding small molecule, an XTEN sequence, FcRn binding moieties (e.g., complete Fc regions or portions thereof which bind to FcRn), single chain Fc regions (ScFc regions, e.g., as described in US 2008/0260738, WO 2008/012543, or WO 2008/1439545), polyglycine linkers, polyserine linkers, peptides and short polypeptides of 6-40 amino acids of two types of amino acids selected from glycine (G), alanine (A), serine (S), threonine (T), glutamate (E) and proline (P) with varying degrees of secondary structure from less than 50% to greater than 50%, amongst others, or two or more combinations thereof. In some embodiments, the polypeptide encoded by the heterologous nucleotide sequence is linked to a non-polypeptide moiety. Non-limiting examples of the non-polypeptide moieties include polyethylene glycol (PEG), albumin-binding small molecules, polysialic acid, hydroxyethyl starch (HES), a derivative thereof, or any combinations thereof.

As used herein, the term "Fc region" is defined as the portion of a polypeptide which corresponds to the Fc region of native Ig, i.e., as formed by the dimeric association of the respective Fc domains of its two heavy chains. A native Fc region forms a homodimer with another Fc region. In contrast, the term "genetically-fused Fc region" or "single-chain Fc region" (scFc region), as used herein, refers to a synthetic dimeric Fc region comprised of Fc domains genetically linked within a single polypeptide chain (i.e., encoded in a single contiguous genetic sequence).

In one embodiment, the "Fc region" refers to the portion of a single Ig heavy chain beginning in the hinge region just upstream of the papain cleavage site (i.e., residue 216 in IgG, taking the first residue of heavy chain constant region to be 114) and ending at the C-terminus of the antibody. Accordingly, a complete Fc domain comprises at least a hinge domain, a CH2 domain, and a CH3 domain.

The Fc region of an Ig constant region, depending on the Ig isotype can include the CH2, CH3, and CH4 domains, as well as the hinge region. Chimeric proteins comprising an Fc region of an Ig bestow several desirable properties on a chimeric protein including increased stability, increased serum half-life (see Capon et al., 1989, Nature 337:525) as well as binding to Fc receptors such as the neonatal Fc receptor (FcRn) (U.S. Pat. Nos. 6,086,875, 6,485,726, 6,030,613; WO 03/077834; US2003-0235536A1), which are incorporated herein by reference in their entireties.

A "reference nucleotide sequence," when used herein as a comparison to a nucleotide sequence of the invention, is a polynucleotide sequence essentially identical to the nucleotide sequence of the invention except that the portions corresponding to FIX sequence are not optimized. For example, the reference nucleotide sequence for a nucleic acid molecule consisting of the codon optimized FIX of SEQ ID NO:1 and a heterologous nucleotide sequence that encodes a single chain Fc region linked to SEQ ID NO:1 at its 3' end is a nucleic acid molecule consisting of the original (or "parent") FIX of SEQ ID NO:2 and the identical heterologous nucleotide sequence that encodes a single chain Fc region linked to SEQ ID NO:2 at its 3' end.

A "codon adaptation index," as used herein, refers to a measure of codon usage bias. A codon adaptation index (CAI) measures the deviation of a given protein coding gene sequence with respect to a reference set of genes (Sharp P M and Li W H, Nucleic Acids Res. 15(3):1281-95 (1987)). CAI is calculated by determining the geometric mean of the weight associated to each codon over the length of the gene sequence (measured in codons):

$$CAI = \exp\left(1/L \sum_{l=1}^{L} \ln(w_i(l))\right). \quad \text{(I)}$$

For each amino acid, the weight of each of its codons, in CAI, is computed as the ratio between the observed frequency of the codon (fi) and the frequency of the synonymous codon (fj) for that amino acid:

Formula 2

$$w_i = \frac{f_i}{\max(f_j)} ij \in [\text{synonymous codons for amino acid}] \quad \text{(II)}$$

As used herein, the term "optimized," with regard to nucleotide sequences, refers to a polynucleotide sequence that encodes a polypeptide, wherein the polynucleotide sequence has been mutated to enhance a property of that polynucleotide sequence. In some embodiments, the optimization is done to increase transcription levels, increase translation levels, increase steady-state mRNA levels, increase or decrease the binding of regulatory proteins such as general transcription factors, increase or decrease splicing, or increase the yield of the polypeptide produced by the polynucleotide sequence. Examples of changes that can be made to a polynucleotide sequence to optimize it include codon optimization, G/C content optimization, removal of repeat sequences, removal of AT rich elements, removal of cryptic splice sites, removal of cis-acting elements that repress transcription or translation, adding or removing poly-T or poly-A sequences, adding sequences around the transcription start site that enhance transcription, such as Kozak consensus sequences, removal of sequences that could form stem loop structures, removal of destabilizing sequences, and two or more combinations thereof.

The present invention is directed to optimized Factor IX sequences, vectors and host cells comprising optimized Factor IX sequences, polypeptides encoded by optimized Factor IX sequences, and methods of producing such polypeptides. The present invention is also directed to methods of treating bleeding disorders such as hemophilia comprising administering to the subject an optimized Factor IX nucleic acid sequence or the polypeptide encoded thereby. The present invention meets an important need in the art by providing optimized Factor IX sequences that demonstrate increased expression in host cells, improved yield of Factor IX protein in methods to produce recombinant Factor IX, and potentially result in greater therapeutic efficacy when used in gene therapy methods.

In some embodiments, the present invention provides an isolated nucleic acid molecule comprising a nucleotide sequence that encodes a polypeptide with Factor IX (FIX) activity, wherein the nucleotide sequence is at least 85% identical to SEQ ID NO: 1. In other embodiments, the nucleotide sequence is at least 86%, at least 87%, at least 88%, at least 89%, at least 90%, at least 91%, at least 92%, at least 93%, at least 94%, at least 95%, at least 96%, at least 97%, at least 98%, or at least 99% identical to SEQ ID NO:1 and encodes a polypeptide with FIX activity. In still other embodiments, the nucleotide sequence comprises SEQ ID NO: 1. In some embodiments, the present invention provides an isolated nucleic acid molecule comprising a nucleotide sequence that encodes a polypeptide with Factor IX (FIX) activity, wherein the nucleotide sequence is at least 80% identical to SEQ ID NO: 54. In other embodiments, the present invention provides an isolated nucleic acid molecule comprising a nucleotide sequence that encodes a polypeptide with Factor IX (FIX) activity, wherein the nucleotide sequence is at least 80% identical to SEQ ID NO: 55. In yet other embodiments, the present invention provides an isolated nucleic acid molecule comprising a nucleotide sequence that encodes a polypeptide with Factor IX (FIX) activity, wherein the nucleotide sequence is at least 80% identical to SEQ ID NO: 56. In still other embodiments, the present invention provides an isolated nucleic acid molecule comprising a nucleotide sequence that encodes a polypeptide with Factor IX (FIX) activity, wherein the nucleotide sequence is at least 80% identical to SEQ ID NO: 57. In certain embodiments, the present invention provides an isolated nucleic acid molecule comprising a nucleotide sequence that encodes a polypeptide with Factor IX (FIX) activity, wherein the nucleotide sequence is at least 80% identical to SEQ ID NO: 58. In other embodiments, the nucleotide sequence is at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to SEQ ID NO:54, 55, 56, 57, or 58.

In certain embodiments, the nucleotide molecule that is at least 80% identical to SEQ ID NO: 54, 55, 56, 57, or 58 comprises a codon optimized nucleic acid sequence encoding a C-terminal portion of the FIX polypeptide ("C-terminal portion nucleotides") and a codon optimized nucleic acid sequence encoding an N-terminal portion of the FIX polypeptide ("N-terminal portion nucleotides"), wherein (a) a relative frequency of codon usage of the C-terminal portion nucleotides is between about 90% to about 100%, and (b) a relative frequency of codon usage of the N-terminal portion nucleotides is between about 40% to about 85%, and wherein the FIX nucleotide molecule exhibits enhanced expression of the FIX polypeptide from a cell compared to a wild type FIX nucleotide sequence.

In some other aspects, the invention is directed to a nucleotide sequence encoding a FIX polypeptide ("FIX nucleotide sequence"), the sequence comprising C-terminal portion nucleotides and N-terminal portion nucleotides, wherein (a) a relative frequency of codon usage of the C-terminal portion nucleotides is at least about 80%, at least about 85%, at least about 90% (e.g., between about 90% to about 100%), and (b) a relative frequency of codon usage of the N-terminal portion nucleotides is between about 40% to about 85%, and wherein the FIX nucleotide sequence exhibits an enhanced expression of the FIX polypeptide from a cell compared to the FIX nucleotide sequence without codon optimization. In certain embodiments, the relative frequency of codon usage of the C-terminal portion nucleotides is between about 95% to about 100%. In other embodiments, the relative frequency of codon usage of the N-terminal portion nucleotides is between about 50% to about 80%. In yet other embodiments, the relative frequency of codon usage of the N-terminal portion nucleotides is between about 60% to about 75%. In certain embodiments, the C-terminal portion nucleotides encode amino acids 1 to 150-300 corresponding to SEQ ID NO: 3 and the N terminal portion nucledotides encode amino acids 151-301 to 461 corresponding to SEQ ID NO: 3.

The invention also includes a method of making a recombinant Factor IX nucleotide molecule comprising codon optimizing C terminal portion nucleotides and N terminal portion nucleotides, wherein a relative frequency of codon usage of the C-terminal portion nucleotides is between about 90% to about 100% and a relative frequency of codon usage of the N-terminal portion nucleotides is between about 40% to about 85%, wherein the codon optimized C-terminal portion nucleotides and the codon optimized N-terminal portion nucleotides encode a FIX polypeptide with enhanced expression in a cell compared to a nucleotide sequence without the codon optimization. In some embodiments, the relative frequency of codon usage of the C-terminal portion nucleotides is between about 95% to about 100%. In other embodiments, the relative frequency of codon usage of the N-terminal portion nucleotides is between about 50% to about 80%. In certain embodiments, the relative frequency of codon usage of the N-terminal portion nucleotides is between about 60% to about 75%. In other embodiments, the C-terminal portion nucleotides encode amino acids 1 to 150-300 corresponding to SEQ ID NO: 3 and the N terminal portion nucledotides encode amino acids 151-301 to 461 corresponding to SEQ ID NO: 3.

SEQ ID NO:1 is an optimized version of SEQ ID NO: 2, the starting or "parental" FIX nucleotide sequence. SEQ ID NO: 2 encodes a wild type human FIX, which contains Arginine at residue 338 corresponding to mature FIX (i.e., residue 384 corresponding to full length FIX with the signal peptide and propeptide). In one embodiment, the nucleic acid molecule encodes a human FIX variant, which contains an amino acid substitution at residue 338 corresponding to mature FIX from Arginine (R) to Leucine (L) (i.e., residue 384 corresponding to full length FIX with the signal peptide and propeptide). In another embodiment, the nucleic acid molecule encodes a human FIX, which contains an amino acid substitution at residue 338 corresponding to mature FIX from Arginine to any amino acid other than Arginine (e.g., Aliphatic amino acids (Glycine, Alanine, Valine, Leucine, and Isoleucine), Hydroxyl or Sulfur/Selenium-containing amino acids (Serine, Cysteine, Selenocysteine, Threonine, and Methionine), Cyclicamino acids (Proline), Aromatic amino acids (Phenylalanine, Tyrosine, and Tryptophan), Basic amino acids (Histidine, Lysine, and Arginine), or Acidic amino acids (Aspartate, Glutamate, Asparagine, and Glutamine)). In some embodiments, the nucleic acid molecule encodes a human FIX, which contains a conservative amino acid substitution at residue 338 correspondinng to mature FIX (residue 384 corresponding to full-length FIX). In other embodiments, the nucleic acid molecule encodes a human FIX, which contains an amino acid substitution at residue 338 corresponding to mature FIX from Arginine to Alanine. While SEQ ID NO:1 is derived from a wild-type full-length FIX (SEQ ID NO: 2), it is to be understood that the present invention is also directed to optimized versions of nucleic acids encoding other versions of FIX that retain FIX activity. For example, other versions of FIX include full-length FIX minus Met at the N-terminus, full-length FIX minus the signal sequence, mature FIX (minus the signal sequence and propeptide), mature FIX with an additional Met at the N-terminus, or fragments of FIX that retain FIX activity. FIX can be made by recombinant means ("recombinant Factor IX" or "rFIX"), i.e., it is not naturally occurring or derived from plasma. Other examples of FIX sequences are also disclosed in US Patent Publication No. 2011/244550, which was published Oct. 6, 2011, or International Application Publication No. WO2010/029178, which was published Mar. 18, 2010, both of which are incorporated herein by reference in their entireties.

A great many functional FIX variants are known. International publication number WO 02/040544 A3, which is herein incorporated by reference in its entirety, discloses mutants that exhibit increased resistance to inhibition by heparin at page 4, lines 9-30 and page 15, lines 6-31. U.S. Pat. No. 6,531,298, published Mar. 11, 2003 and incorporated herein by reference in its entirety, discloses a FIX mutant having an amino acid substitution at residue 338 corresponding to mature FIX from Arginine to Alanine. International publication number WO 03/020764 A2, which is herein incorporated by reference in its entirety, discloses FIX mutants with reduced T cell immunogenicity in Tables 2 and 3 (on pages 14-24), and at page 12, lines 1-27. International publication number WO 2007/149406 A2, which is herein incorporated by reference in its entirety, discloses functional mutant FIX molecules that exhibit increased protein stability, increased in vivo and in vitro half-life, and increased resistance to proteases at page 4, line 1 to page 19, line 11. WO 2007/149406 A2 also discloses chimeric and other variant FIX molecules at page 19, line 12 to page 20, line 9. International publication number WO 08/118507 A2, which is herein incorporated by reference in its entirety, discloses FIX mutants that exhibit increased clotting activity at page 5, line 14 to page 6, line 5. International publication number WO 09/051717 A2, which is herein incorporated by reference in its entirety, discloses FIX mutants having an increased number of N-linked and/or O-linked glycosylation sites, which results in an increased half-life and/or recovery at page 9, line 11 to page 20, line 2. International publication number WO 09/137254 A2, which is herein incorporated by reference in its entirety, also discloses Factor IX mutants with increased numbers of glycosylation sites at page 2, paragraph [006] to page 5, paragraph [011] and page 16, paragraph [044] to page 24, paragraph [057]. International publication number WO 09/130198 A2, which is herein incorporated by reference in its entirety, discloses functional mutant FIX molecules that have an increased number of glycosylation sites, which result in an increased half-life, at page 4, line 26 to page 12, line 6. International publication number WO 09/140015 A2, which is herein incorporated by reference in its entirety, discloses functional FIX mutants that an increased number of Cys residues, which can be used for polymer (e.g., PEG) conjugation, at page 11, paragraph [0043] to page 13, paragraph [0053]. The FIX polypeptides described in International Application No. PCT/US2011/043569 filed Jul. 11, 2011 and published as WO 2012/006624 on Jan. 12, 2012 are also incorporated herein by reference in its entirety.

In addition, hundreds of non-functional mutations in FIX have been identified in hemophilia subjects, many of which are disclosed in Table 5, at pages 11-14 of International publication number WO 09/137254 A2, which is herein incorporated by reference in its entirety. Such non-functional mutations are not included in the invention, but provide additional guidance for which mutations are more or less likely to result in a functional FIX polypeptide.

"A polypeptide with FIX activity" as used herein means a functional FIX polypeptide in its normal role in coagulation, unless otherwise specified. The term a polypeptide with FIX activity includes a functional fragment, variant, analog, or derivative thereof that retains the function of full-length wild-type Factor IX in the coagulation pathway. "A polypeptide with FIX activity" is used interchangeably with FIX protein, FIX polypeptide, or FIX. Examples of FIX functions include, but are not limited to, an ability to activate coagulation, an ability to act as a cofactor for factor VIII, or an ability to form a tenase complex with factor VIII in the presence of $Ca^{2+}$ and phospholipids, which then converts Factor X to the activated form Xa. The FIX polypeptide can contain one or more mutation or substitutions. The FIX protein can be the human, porcine, canine, rat, or murine FIX protein. Factor IX coagulant activity is expressed as International Unit(s) (IU). One IU of Factor IX activity corresponds approximately to the quantity of Factor IX in one milliliter of normal human plasma. Several assays are available for measuring Factor IX activity, including the one stage clotting assay (activated partial thromboplastin time; aPTT), thrombin generation time (TGA) and rotational thromboelastometry (ROTEM®).

Codon Optimization

In one embodiment, the present invention provides an isolated nucleic acid molecule comprising a nucleotide sequence that encodes a polypeptide with FIX activity, wherein the nucleic acid sequence has been codon optimized. In another embodiment, the starting nucleic acid sequence that encodes a polypeptide with FIX activity and that is subject to codon optimization is SEQ ID NO:2. In some embodiments, the sequence that encodes a polypeptide with FIX activity is codon optimized for human expression. In other embodiments, the sequence that encodes a polypeptide with FIX activity is codon optimized for murine expression. SEQ ID NO:1 is a codon optimized version of SEQ ID NO:2, optimized for human expression.

The term "codon-optimized" as it refers to genes or coding regions of nucleic acid molecules for transformation of various hosts, refers to the alteration of codons in the gene or coding regions of the nucleic acid molecules to reflect the typical codon usage of the host organism without altering the polypeptide encoded by the DNA. Such optimization includes replacing at least one, or more than one, or a significant number, of codons with one or more codons that are more frequently used in the genes of that organism.

Deviations in the nucleotide sequence that comprises the codons encoding the amino acids of any polypeptide chain allow for variations in the sequence coding for the gene. Since each codon consists of three nucleotides, and the nucleotides comprising DNA are restricted to four specific bases, there are 64 possible combinations of nucleotides, 61 of which encode amino acids (the remaining three codons encode signals ending translation). The "genetic code" which shows which codons encode which amino acids is reproduced herein as Table 1. As a result, many amino acids are designated by more than one codon. For example, the amino acids alanine and proline are coded for by four triplets, serine and arginine by six, whereas tryptophan and methionine are coded by just one triplet. This degeneracy allows for DNA base composition to vary over a wide range without altering the amino acid sequence of the proteins encoded by the DNA.

TABLE 1

The Standard Genetic Code

|   | T | C | A | G |
|---|---|---|---|---|
| T | TTT Phe (F) | TCT Ser (S) | TAT Tyr (Y) | TGT Cys (C) |
|   | TTC Phe (F) | TCC Ser (S) | TAC Tyr (Y) | TGC |
|   | TTA Leu (L) | TCA Ser (S) | TAA Stop | TGA Stop |
|   | TTG Leu (L) | TCG Ser (S) | TAG Stop | TGG Trp (W) |
| C | CTT Leu (L) | CCT Pro (P) | CAT His (H) | CGT Arg (R) |
|   | CTC Leu (L) | CCC Pro (P) | CAC His (H) | CGC Arg (R) |
|   | CTA Leu (L) | CCA Pro (P) | CAA Gln (Q) | CGA Arg (R) |
|   | CTG Leu (L) | CCG Pro (P) | CAG Gln (Q) | CGG Arg (R) |
| A | ATT Ile (I) | ACT Thr (T) | AAT Asn (N) | AGT Ser (S) |
|   | ATC Ile (I) | ACC Thr (T) | AAC Asn (N) | AGC Ser (S) |
|   | ATA Ile (I) | ACA Thr (T) | AAA Lys (K) | AGA Arg (R) |
|   | ATG Met (M) | ACG Thr (T) | AAG Lys (K) | AGG Arg (R) |
| G | GTT Val (V) | GCT Ala (A) | GAT Asp (D) | GGT Gly (G) |
|   | GTC Val (V) | GCC Ala (A) | GAC Asp (D) | GGC Gly (G) |
|   | GTA Val (V) | GCA Ala (A) | GAA Glu (E) | GGA Gly (G) |
|   | GTG Val (V) | GCG Ala (A) | GAG Glu (E) | GGG Gly (G) |

Many organisms display a bias for use of particular codons to code for insertion of a particular amino acid in a growing peptide chain. Codon preference, or codon bias, differences in codon usage between organisms, is afforded by degeneracy of the genetic code, and is well documented among many organisms. Codon bias often correlates with the efficiency of translation of messenger RNA (mRNA), which is in turn believed to be dependent on, inter alia, the properties of the codons being translated and the availability of particular transfer RNA (tRNA) molecules. The predominance of selected tRNAs in a cell is generally a reflection of the codons used most frequently in peptide synthesis. Accordingly, genes can be tailored for optimal gene expression in a given organism based on codon optimization.

Given the large number of gene sequences available for a wide variety of animal, plant and microbial species, the relative frequencies of codon usage have been calculated. Codon usage tables are available, for example, at the "Codon Usage Database" available at www.kazusa.or.jp/codon/ (visited Jun. 18, 2012). See Nakamura, Y., et al. Nucl. Acids Res. 28:292 (2000).

Randomly assigning codons at an optimized frequency to encode a given polypeptide sequence can be done manually by calculating codon frequencies for each amino acid, and then assigning the codons to the polypeptide sequence randomly. Additionally, various algorithms and computer software programs can be used to calculate an optimal sequence.

In one embodiment, the present invention provides an isolated nucleic acid molecule comprising a nucleotide sequence that encodes a polypeptide with FIX activity, wherein the nucleotide sequence is at least 79%, at least 80%, at least 81%, at least 82%, at least 83%, at least 84%, at least 85% identical to SEQ ID NO:1, and wherein the human codon adaptation index is increased relative to SEQ ID NO:2. For example, the nucleotide sequence that encodes a polypeptide with FIX activity and that is at least 85% identical to SEQ ID NO: 1 can have a human codon adaptation index that is at least about 0.73, at least about 0.74, at least about 0.75, at least about 0.76, at least about 0.77, at least about 0.78, at least about 0.79, at least about 0.80, at least about 0.81, at least about 0.82, at least about 0.83, at least about 0.84, at least about 0.85, at least about 0.86, at least about 0.87, at least about 0.88, at least about 0.89, or at least about 0.90.

In other embodiments, the present invention provides an isolated nucleic acid molecule comprising a nucleotide sequence that encodes a polypeptide with Factor IX activity, wherein the nucleotide sequence is at least 85% identical to SEQ ID NO:1 and has one or more of the following characteristics: (1) the nucleotide sequence contains a higher percentage of G/C nucleotides compared to SEQ ID NO:2, (2) the nucleotide sequence does not contain the splice site GGTGAT or GGTAAG, (3) the nucleotide sequence contains fewer destabilizing elements, (4) the nucleotide sequence does not contain a poly-T sequence, (5) the nucleotide sequence does not contain a poly-A sequence, (6) the nucleotide sequence has a codon adaptation index that is increased relative to SEQ ID NO:2, (7) the nucleotide sequence contains less antiviral motifs, or a combination of two or more such characteristics. In a particular embodiment, the nucleotide sequence contains all of the characteristics (1) to (7).

G/C Content Optimization

In some embodiments, the present invention provides an isolated nucleic acid molecule comprising a nucleotide sequence that encodes a polypeptide with FIX activity, wherein the nucleotide sequence is at least 85% identical to SEQ ID NO:1, and wherein the nucleotide sequence contains a higher percentage of G/C nucleotides compared to the percentage of G/C nucleotides in SEQ ID NO:2. In other embodiments, the nucleotide sequence that encodes a polypeptide with FIX activity and that is at least 85% identical to SEQ ID NO:1 has a G/C content that is at least about 42%, at least about 43%, at least about 44%, at least about 45%, at least about 46%, at least about 47%, at least about 48%, at least about 49%, at least about 50%, at least about 51%, at least about 52%, at least about 53%, at least about 54%, or at least about 55%.

"G/C content" (or guanine-cytosine content), or "percentage of G/C nucleotides," refers to the percentage of nitrogenous bases in a DNA molecule that are either guanine or cytosine. G/C content can be calculated using the following formula:

$$\frac{G+C}{A+T+G+C} \times 100 \qquad (III)$$

Human genes are highly heterogeneous in their G/C content, with some genes having a G/C content as low as 20%, and other genes having a G/C content as high as 95%. In general, G/C rich genes are more highly expressed. In fact, it has been demonstrated that increasing the G/C content of a gene can lead to increased expression of the gene, due mostly to an increase in transcription and higher steady state mRNA levels. See Kudla et al., PLoS Biol., 4(6): e180 (2006).

Destabilizing Sequences

In some embodiments, the present invention provides an isolated nucleic acid molecule comprising a nucleotide sequence that encodes a polypeptide with FIX activity, wherein the nucleotide sequence is at least 85% identical to SEQ ID NO:1 or 80% identical to SEQ ID NO: 54, 55, 56, 56, or 58, and wherein the nucleotide sequence contains fewer destabilizing elements relative to SEQ ID NO:2. In other embodiments, the nucleotide sequence that encodes a polypeptide with FIX activity and that is at least 85% identical to SEQ ID NO:1 or 80% identical to SEQ ID NO: 54, 55, 56, 56, or 58 does not contain a destabilizing element.

There is one destabilizing element ATTTA (SEQ ID NO:) in the parental FIX sequence (SEQ ID NO:2. In one embodiment, sequence of this site was mutated to destroy the destabilizing element in optimized FIX SEQ ID NO: 1. The location of each of these elements, and the sequence of the corresponding nucleotides in the optimized sequences are shown in Table.

Other Cis Acting Negative Regulatory Elements

In certain embodiments, the present invention provides an isolated nucleic acid molecule comprising a nucleotide sequence that encodes a polypeptide with FIX activity, wherein the nucleotide sequence is at least 79%, at least 80%, at least 85%, at least 90%, at least 95%, at least 96%, at least 97%, at least 98%, at least 99%, or 100% identical to SEQ ID NO:1 or SEQ ID NO: 54, 55, 56, 56, or 58, wherein the nucleotide sequence does not contain one or more cis-acting negative regulatory elements, for example, a splice site GGTAAG (SEQ ID NO:4) or GGTGAT (SEQ ID NO:5), a poly-T sequence (SEQ ID NO:7), a poly-A sequence (SEQ ID Nos:8-10), an AU rich element (ARE) sequence (SEQ ID Nos:14 and 15), or any combinations thereof.

In other embodiments, an optimized FIX sequence of the invention does not comprise one or more of antiviral motifs (SEQ ID NO:11), stem-loop structures, and repeat sequences.

Heterologous Nucleotide Sequences

In some embodiments, the isolated nucleic acid molecules of the invention further comprise a heterologous nucleotide sequence. In some embodiments, the isolated nucleic acid molecules of the invention further comprise at least one heterologous nucleotide sequence. The heterologous nucleotide sequence can be linked with the optimized FIX nucleotide sequences of the invention at the 5' end, at the 3' end, or inserted into the middle of the optimized FIX nucleotide sequence. Thus, in some embodiments, the heterologous amino acid sequence encoded by the heterologous nucleotide sequence is linked to the N-terminus or the C-terminus of the FIX amino acid sequence encoded by the nucleotide sequence or inserted between two amino acids in the FIX amino acid sequence. In other embodiments, the isolated nucleic acid molecules of the invention further comprise two, three, four, five, six, seven, or eight heterologous nucleotide sequences. In some embodiments, all the heterologous nucleotide sequences are identical. In some embodiments, at least one heterologous nucleotide sequence is different from the other heterologous nucleotide sequences.

In some embodiments, the invention can comprise two, three, four, five, six, or more than seven heterologous nucleotide sequences in tandem.

In some embodiments, the heterologous nucleotide sequence encodes an amino acid sequence. In some embodiments, the amino acid sequence encoded by the heterologous nucleotide sequence is a heterologous moiety that can increase the half-life (a "half-life extender") of a FIX molecule.

In some embodiments, the heterologous moiety is a peptide or a polypeptide with either unstructured or structured characteristics that are associated with the prolongation of in vivo half-life when incorporated in a protein of the invention. Non-limiting examples include albumin, albumin fragments, Fc fragments of immunoglobulins, the C-terminal peptide (CTP) of the β subunit of human chorionic gonadotropin, a HAP sequence, an XTEN sequence, a transferrin or a fragment thereof, a PAS polypeptide, polyglycine linkers, polyserine linkers, albumin-binding moieties, or any fragments, derivatives, variants, or combinations of these polypeptides. In some aspects, a heterologous moiety includes von Willebrand factor or a fragment thereof. In other related aspects a heterologous moiety can include an attachment site (e.g., a cysteine amino acid) for a non-polypeptide moiety such as polyethylene glycol (PEG), hydroxyethyl starch (HES), polysialic acid, or any derivatives, variants, or combinations of these elements. In some aspects, a heterologous moiety comprises a cysteine amino acid that functions as an attachment site for a non-polypeptide moiety such as polyethylene glycol (PEG), hydroxyethyl starch (HES), polysialic acid, or any derivatives, variants, or combinations of these elements.

In one specific embodiment, a first heterologous nucleotide sequence encodes a first heterologous moiety that is a half-life extending molecule which is known in the art, and a second heterologous nucleotide sequence encodes a second heterologous moiety that can also be a half-life extending molecule which is known in the art. In certain embodiments, the first heterologous moiety (e.g., a first Fc moiety) and the second heterologous moiety (e.g., a second Fc moiety) are associated with each other to form a dimer. In one embodiment, the second heterologous moiety is a second Fc moiety, wherein the second Fc moiety is linked to or associated with the first heterologous moiety, e.g., the first Fc moiety. For example, the second heterologous moiety (e.g., the second Fc moiety) can be linked to the first heterologous moiety (e.g., the first Fc moiety) by a linker or associated with the first heterologous moiety by a covalent or non-covalent bond.

In some embodiments, the heterologous moiety is a polypeptide comprising, consisting essentially of, or consisting of at least about 10, at least about 100, at least about 200, at least about 300, at least about 400, at least about 500, at least about 600, at least about 700, at least about 800, at least about 900, at least about 1000, at least about 1100, at least about 1200, at least about 1300, at least about 1400, at least about 1500, at least about 1600, at least about 1700, at least about 1800, at least about 1900, at least about 2000, at least about 2500, at least about 3000, or at least about 4000 amino acids. In other embodiments, the heterologous moiety is a polypeptide comprising, consisting essentially of, or consisting of about 100 to about 200 amino acids, about 200 to about 300 amino acids, about 300 to about 400 amino acids, about 400 to about 500 amino acids, about 500 to about 600 amino acids, about 600 to about 700 amino acids, about 700 to about 800 amino acids, about 800 to about 900 amino acids, or about 900 to about 1000 amino acids.

In certain embodiments, a heterologous moiety improves one or more pharmacokinetic properties of the FIX protein without significantly affecting its biological activity or function.

In certain embodiments, a heterologous moiety increases the in vivo and/or in vitro half-life of the FIX protein of the invention. In other embodiments, a heterologous moiety facilitates visualization or localization of the FIX protein of the invention or a fragment thereof (e.g., a fragment comprising a heterologous moiety after proteolytic cleavage of the FIX protein). Visualization and/or location of the FIX protein of the invention or a fragment thereof can be in vivo, in vitro, ex vivo, or combinations thereof.

In other embodiments, a heterologous moiety increases stability of the FIX protein of the invention or a fragment thereof (e.g., a fragment comprising a heterologous moiety after proteolytic cleavage of the FIX protein). As used herein, the term "stability" refers to an art-recognized measure of the maintenance of one or more physical properties of the FIX protein in response to an environmental condition (e.g., an elevated or lowered temperature). In certain aspects, the physical property can be the maintenance of the covalent structure of the FIX protein (e.g., the absence of proteolytic cleavage, unwanted oxidation or deamidation). In other aspects, the physical property can also be the presence of the FIX protein in a properly folded state (e.g., the absence of soluble or insoluble aggregates or precipitates). In one aspect, the stability of the FIX protein is measured by assaying a biophysical property of the FIX protein, for example thermal stability, pH unfolding profile, stable removal of glycosylation, solubility, biochemical function (e.g., ability to bind to a protein, receptor or ligand), etc., and/or combinations thereof. In another aspect, biochemical function is demonstrated by the binding affinity of the interaction. In one aspect, a measure of protein stability is thermal stability, i.e., resistance to thermal challenge. Stability can be measured using methods known in the art, such as, HPLC (high performance liquid chromatography), SEC (size exclusion chromatography), DLS (dynamic light scattering), etc. Methods to measure thermal stability include, but are not limited to differential scanning calorimetry (DSC), differential scanning fluorimetry (DSF), circular dichroism (CD), and thermal challenge assay.

In certain aspects, a FIX protein of the invention comprises at least one half-life extender, i.e., a heterologous moiety which increases the in vivo half-life of the FIX protein with respect to the in vivo half-life of the corresponding FIX protein lacking such heterologous moiety. In vivo half-life of a FIX protein can be determined by any methods known to those of skill in the art, e.g., activity assays (chromogenic assay or one stage clotting aPTT assay), ELISA, ROTEM™, etc.

In some embodiments, the presence of one or more half-life extenders results in the half-life of the FIX protein to be increased compared to the half-life of the corresponding protein lacking such one or more half-life extenders. The half-life of the FIX protein comprising a half-life extender is at least about 1.5 times, at least about 2 times, at least about 2.5 times, at least about 3 times, at least about 4 times, at least about 5 times, at least about 6 times, at least about 7 times, at least about 8 times, at least about 9 times, at least about 10 times, at least about 11 times, or at least about 12 times longer than the in vivo half-life of the corresponding FIX protein lacking such half-life extender.

In one embodiment, the half-life of the FIX protein comprising a half-life extender is about 1.5-fold to about 20-fold, about 1.5 fold to about 15 fold, or about 1.5 fold to about 10 fold longer than the in vivo half-life of the corresponding protein lacking such half-life extender. In another embodiment, the half-life of FIX protein comprising a half-life extender is extended about 2-fold to about 10-fold, about 2-fold to about 9-fold, about 2-fold to about 8-fold, about 2-fold to about 7-fold, about 2-fold to about 6-fold, about 2-fold to about 5-fold, about 2-fold to about 4-fold, about 2-fold to about 3-fold, about 2.5-fold to about 10-fold, about 2.5-fold to about 9-fold, about 2.5-fold to about 8-fold, about 2.5-fold to about 7-fold, about 2.5-fold to about 6-fold, about 2.5-fold to about 5-fold, about 2.5-fold to about 4-fold, about 2.5-fold to about 3-fold, about 3-fold to about 10-fold, about 3-fold to about 9-fold, about 3-fold to about 8-fold, about 3-fold to about 7-fold, about 3-fold to about 6-fold, about 3-fold to about 5-fold, about 3-fold to about 4-fold, about 4-fold to about 6 fold, about 5-fold to about 7-fold, or about 6-fold to about 8 fold as compared to the in vivo half-life of the corresponding protein lacking such half-life extender.

In other embodiments, the half-life of the FIX protein comprising a half-life extender is at least about 17 hours, at least about 18 hours, at least about 19 hours, at least about 20 hours, at least about 21 hours, at least about 22 hours, at least about 23 hours, at least about 24 hours, at least about 25 hours, at least about 26 hours, at least about 27 hours, at least about 28 hours, at least about 29 hours, at least about 30 hours, at least about 31 hours, at least about 32 hours, at least about 33 hours, at least about 34 hours, at least about 35 hours, at least about 36 hours, at least about 48 hours, at least about 60 hours, at least about 72 hours, at least about 84 hours, at least about 96 hours, or at least about 108 hours.

In still other embodiments, the half-life of the FIX protein comprising a half-life extender is about 15 hours to about two weeks, about 16 hours to about one week, about 17 hours to about one week, about 18 hours to about one week, about 19 hours to about one week, about 20 hours to about one week, about 21 hours to about one week, about 22 hours to about one week, about 23 hours to about one week, about 24 hours to about one week, about 36 hours to about one week, about 48 hours to about one week, about 60 hours to about one week, about 24 hours to about six days, about 24 hours to about five days, about 24 hours to about four days, about 24 hours to about three days, or about 24 hours to about two days.

In some embodiments, the average half-life per subject of the FIX protein comprising a half-life extender is about 15 hours, about 16 hours, about 17 hours, about 18 hours, about 19 hours, about 20 hours, about 21 hours, about 22 hours, about 23 hours, about 24 hours (1 day), about 25 hours, about 26 hours, about 27 hours, about 28 hours, about 29 hours, about 30 hours, about 31 hours, about 32 hours, about 33 hours, about 34 hours, about 35 hours, about 36 hours, about 40 hours, about 44 hours, about 48 hours (2 days), about 54 hours, about 60 hours, about 72 hours (3 days), about 84 hours, about 96 hours (4 days), about 108 hours, about 120 hours (5 days), about six days, about seven days (one week), about eight days, about nine days, about 10 days, about 11 days, about 12 days, about 13 days, or about 14 days.

1. An Immunoglobulin Constant Region or a Portion Thereof

In another aspect, a heterologous moiety comprises one or more immunoglobulin constant regions or portions thereof (e.g., an Fc region). In one embodiment, an isolated nucleic acid molecule of the invention further comprises a heterologous nucleic acid sequence that encodes an immunoglobulin constant region or a portion thereof. In some embodiments, the immunoglobulin constant region or portion thereof is an Fc region.

An immunoglobulin constant region is comprised of domains denoted CH (constant heavy) domains (CH1, CH2, etc.). Depending on the isotype, (i.e. IgG, IgM, IgA IgD, or IgE), the constant region can be comprised of three or four CH domains. Some isotypes (e.g. IgG) constant regions also contain a hinge region. See Janeway et al. 2001, *Immunobiology*, Garland Publishing, N.Y., N.Y.

An immunoglobulin constant region or a portion thereof for producing the FIX protein of the present invention can be obtained from a number of different sources. In one embodiment, an immunoglobulin constant region or a portion thereof is derived from a human immunoglobulin. It is understood, however, that the immunoglobulin constant region or a portion thereof can be derived from an immunoglobulin of another mammalian species, including for example, a rodent (e.g. a mouse, rat, rabbit, guinea pig) or non-human primate (e.g. chimpanzee, macaque) species. Moreover, the immunoglobulin constant region or a portion thereof can be derived from any immunoglobulin class, including IgM, IgG, IgD, IgA and IgE, and any immunoglobulin isotype, including IgG1, IgG2, IgG3 and IgG4. In one embodiment, the human isotype IgG1 is used.

A variety of the immunoglobulin constant region gene sequences (e.g. human constant region gene sequences) are available in the form of publicly accessible deposits. Constant region domains sequence can be selected having a particular effector function (or lacking a particular effector function) or with a particular modification to reduce immunogenicity. Many sequences of antibodies and antibody-encoding genes have been published and suitable Ig constant region sequences (e.g. hinge, CH2, and/or CH3 sequences, or portions thereof) can be derived from these sequences using art recognized techniques. The genetic material obtained using any of the foregoing methods can then be altered or synthesized to obtain polypeptides of the present invention. It will further be appreciated that the scope of this invention encompasses alleles, variants and mutations of constant region DNA sequences.

The sequences of the immunoglobulin constant region or a portion thereof can be cloned, e.g., using the polymerase chain reaction and primers which are selected to amplify the domain of interest. To clone a sequence of the immunoglobulin constant region or a portion thereof from an antibody, mRNA can be isolated from hybridoma, spleen, or lymph cells, reverse transcribed into DNA, and antibody genes amplified by PCR. PCR amplification methods are described in detail in U.S. Pat. Nos. 4,683,195; 4,683,202; 4,800,159; 4,965,188; and in, e.g., "PCR Protocols: A Guide to Methods and Applications" Innis et al. eds., Academic Press, San Diego, Calif. (1990); Ho et al. 1989. Gene 77:51; Horton et al. 1993. *Methods Enzymol.* 217:270). PCR can be initiated by consensus constant region primers or by more specific primers based on the published heavy and light chain DNA and amino acid sequences. PCR also can be used to isolate DNA clones encoding the antibody light and heavy chains. In this case the libraries can be screened by consensus primers or larger homologous probes, such as mouse constant region probes. Numerous primer sets suitable for amplification of antibody genes are known in the art (e.g., 5' primers based on the N-terminal sequence of purified antibodies (Benhar and Pastan. 1994. *Protein Engineering* 7:1509); rapid amplification of cDNA ends (Ruberti, F. et al. 1994. *J. Immunol. Methods* 173:33); antibody leader sequences (Larrick et al. 1989 *Biochem. Biophys. Res. Commun.* 160:1250). The cloning of antibody sequences is further described in Newman et al., U.S. Pat. No. 5,658,570, filed Jan. 25, 1995, which is incorporated by reference herein.

An immunoglobulin constant region used herein can include all domains and the hinge region or portions thereof. In one embodiment, the immunoglobulin constant region or a portion thereof comprises CH2 domain, CH3 domain, and a hinge region, i.e., an Fc region or an FcRn binding partner.

As used herein, the term "Fc region" is defined as the portion of a polypeptide which corresponds to the Fc region of native Ig, i.e., as formed by the dimeric association of the respective Fc domains of its two heavy chains. A native Fc region forms a homodimer with another Fc region. In contrast, the term "genetically-fused Fc region" or "single-chain Fc region" (scFc region), as used herein, refers to a synthetic dimeric Fc region comprised of Fc domains genetically linked within a single polypeptide chain (i.e., encoded in a single contiguous genetic sequence). See International Publication No. WO 2012/006635, incorporated herein by reference in its entirety.

In one embodiment, the "Fc region" refers to the portion of a single Ig heavy chain beginning in the hinge region just upstream of the papain cleavage site (i.e. residue 216 in IgG, taking the first residue of heavy chain constant region to be 114) and ending at the C-terminus of the antibody. Accordingly, a complete Fc region comprises at least a hinge domain, a CH2 domain, and a CH3 domain.

An immunoglobulin constant region or a portion thereof can be an FcRn binding partner. FcRn is active in adult epithelial tissues and expressed in the lumen of the intestines, pulmonary airways, nasal surfaces, vaginal surfaces, colon and rectal surfaces (U.S. Pat. No. 6,485,726). An FcRn binding partner is a portion of an immunoglobulin that binds to FcRn.

The FcRn receptor has been isolated from several mammalian species including humans. The sequences of the human FcRn, monkey FcRn, rat FcRn, and mouse FcRn are known (Story et al. 1994, J. Exp. Med. 180:2377). The FcRn receptor binds IgG (but not other immunoglobulin classes such as IgA, IgM, IgD, and IgE) at relatively low pH, actively transports the IgG transcellularly in a luminal to serosal direction, and then releases the IgG at relatively higher pH found in the interstitial fluids. It is expressed in adult epithelial tissue (U.S. Pat. Nos. 6,485,726, 6,030,613, 6,086,875; WO 03/077834; US2003-0235536A1) including lung and intestinal epithelium (Israel et al. 1997, Immunology 92:69) renal proximal tubular epithelium (Kobayashi et al. 2002, Am. J. Physiol. Renal Physiol. 282:F358) as well as nasal epithelium, vaginal surfaces, and biliary tree surfaces.

FcRn binding partners useful in the present invention encompass molecules that can be specifically bound by the FcRn receptor including whole IgG, the Fe fragment of IgG, and other fragments that include the complete binding region of the FcRn receptor. The region of the Fc portion of IgG that binds to the FcRn receptor has been described based on X-ray crystallography (Burmeister et al. 1994, Nature 372:379). The major contact area of the Fc with the FcRn is near the junction of the CH2 and CH3 domains. Fc-FcRn contacts are all within a single Ig heavy chain. The FcRn binding partners include whole IgG, the Fc fragment of IgG, and other fragments of IgG that include the complete binding region of FcRn. The major contact sites include amino acid residues 248, 250-257, 272, 285, 288, 290-291, 308-311, and 314 of the CH2 domain and amino acid residues 385-387, 428, and 433-436 of the CH3 domain.

References made to amino acid numbering of immunoglobulins or immunoglobulin fragments, or regions, are all based on Kabat et al. 1991, Sequences of Proteins of Immunological Interest, U.S. Department of Public Health, Bethesda, Md.

Fc regions or FcRn binding partners bound to FcRn can be effectively shuttled across epithelial barriers by FcRn, thus providing a non-invasive means to systemically administer a desired therapeutic molecule. Additionally, fusion proteins comprising an Fc region or an FcRn binding partner are endocytosed by cells expressing the FcRn. But instead of being marked for degradation, these fusion proteins are recycled out into circulation again, thus increasing the in vivo half-life of these proteins. In certain embodiments, the portions of immunoglobulin constant regions are an Fc region or an FcRn binding partner that typically associates, via disulfide bonds and other non-specific interactions, with another Fc region or another FcRn binding partner to form dimers and higher order multimers.

Two FcRn receptors can bind a single Fc molecule. Crystallographic data suggest that each FcRn molecule binds a single polypeptide of the Fc homodimer. In one embodiment, linking the FcRn binding partner, e.g., an Fc fragment of an IgG, to a biologically active molecule provides a means of delivering the biologically active molecule orally, buccally, sublingually, rectally, vaginally, as an aerosol administered nasally or via a pulmonary route, or via an ocular route. In another embodiment, the FIX protein can be administered invasively, e.g., subcutaneously, intravenously.

An FcRn binding partner region is a molecule or portion thereof that can be specifically bound by the FcRn receptor with consequent active transport by the FcRn receptor of the Fc region. Specifically bound refers to two molecules forming a complex that is relatively stable under physiologic conditions. Specific binding is characterized by a high affinity and a low to moderate capacity as distinguished from nonspecific binding which usually has a low affinity with a moderate to high capacity. Typically, binding is considered specific when the affinity constant $K_A$ is higher than $10^6$ $M^{-1}$, or higher than $10^8$ $M^{-1}$. If necessary, non-specific binding can be reduced without substantially affecting specific binding by varying the binding conditions. The appropriate binding conditions such as concentration of the molecules, ionic strength of the solution, temperature, time allowed for binding, concentration of a blocking agent (e.g., serum albumin, milk casein), etc., can be optimized by a skilled artisan using routine techniques.

In certain embodiments, a FIX protein of the invention comprises one or more truncated Fc regions that are nonetheless sufficient to confer Fc receptor (FcR) binding properties to the Fc region. For example, the portion of an Fc region that binds to FcRn (i.e., the FcRn binding portion) comprises from about amino acids 282-438 of IgG1, EU numbering (with the primary contact sites being amino acids 248, 250-257, 272, 285, 288, 290-291, 308-311, and 314 of the CH2 domain and amino acid residues 385-387, 428, and 433-436 of the CH3 domain. Thus, an Fc region of the invention can comprise or consist of an FcRn binding portion. FcRn binding portions can be derived from heavy chains of any isotype, including IgG1, IgG2, IgG3 and IgG4. In one embodiment, an FcRn binding portion from an antibody of the human isotype IgG1 is used. In another embodiment, an FcRn binding portion from an antibody of the human isotype IgG4 is used.

The Fc region can be obtained from a number of different sources. In one embodiment, an Fc region of the polypeptide is derived from a human immunoglobulin. It is understood, however, that an Fc moiety can be derived from an immunoglobulin of another mammalian species, including for example, a rodent (e.g. a mouse, rat, rabbit, guinea pig) or non-human primate (e.g. chimpanzee, macaque) species. Moreover, the polypeptide of the Fc domains or portions thereof can be derived from any immunoglobulin class, including IgM, IgG, IgD, IgA and IgE, and any immunoglobulin isotype, including IgG1, IgG2, IgG3 and IgG4. In another embodiment, the human isotype IgG1 is used.

In certain embodiments, the Fc variant confers a change in at least one effector function imparted by an Fc moiety comprising said wild-type Fc domain (e.g., an improvement or reduction in the ability of the Fc region to bind to Fc receptors (e.g. FcγRI, FcγRII, or FcγRIII) or complement proteins (e.g. C1q), or to trigger antibody-dependent cytotoxicity (ADCC), phagocytosis, or complement-dependent cytotoxicity (CDCC)). In other embodiments, the Fc variant provides an engineered cysteine residue.

The Fc region of the invention can employ art-recognized Fc variants which are known to impart a change (e.g., an enhancement or reduction) in effector function and/or FcR or FcRn binding. Specifically, an Fc region of the invention can include, for example, a change (e.g., a substitution) at one or more of the amino acid positions disclosed in International PCT Publications WO88/07089A1, WO96/14339A1, WO98/05787A1, WO98/23289A1, WO99/51642A1, WO099/58572A1, WO00/09560A2, WO00/32767A1, WO00/42072A2, WO02/44215A2, WO02/060919A2, WO03/074569A2, WO04/016750A2, WO04/029207A2, WO04/035752A2, WO04/063351 A2, WO04/074455A2, WO04/099249A2, WO05/040217A2, WO04/044859, WO05/070963A1, WO05/077981A2, WO05/092925A2, WO05/123780A2, WO06/019447A1, WO06/047350A2, and WO06/085967A2; US Patent Publication Nos. US2007/0231329, US2007/0231329, US2007/0237765, US2007/0237766, US2007/0237767, US2007/0243188, US20070248603, US20070286859, US20080057056; or U.S. Pat. Nos. 5,648,260; 5,739,277; 5,834,250; 5,869,046; 6,096,871; 6,121,022; 6,194,551; 6,242,195; 6,277,375; 6,528,624; 6,538,124; 6,737,056; 6,821,505; 6,998,253; 7,083,784; 7,404,956, and 7,317,091, each of which is incorporated by reference herein. In one embodiment, the specific change (e.g., the specific substitution of one or more amino acids disclosed in the art) can be made at one or more of the disclosed amino acid positions. In another embodiment, a different change at one or more of the disclosed amino acid positions (e.g., the different substitution of one or more amino acid position disclosed in the art) can be made.

The Fc region or FcRn binding partner of IgG can be modified according to well recognized procedures such as site directed mutagenesis and the like to yield modified IgG or Fc fragments or portions thereof that will be bound by FcRn. Such modifications include modifications remote from the FcRn contact sites as well as modifications within the contact sites that preserve or even enhance binding to the FcRn. For example, the following single amino acid residues in human IgG1 Fc (Fc γ1) can be substituted without significant loss of Fc binding affinity for FcRn: P238A, S239A, K246A, K248A, D249A, M252A, T256A, E258A, T260A, D265A, S267A, H268A, E269A, D270A, E272A, L274A, N276A, Y278A, D280A, V282A, E283A, H285A, N286A, T289A, K290A, R292A, E293A, E294A, Q295A, Y296F, N297A, S298A, Y300F, R301A, V303A, V305A, T307A, L309A, Q311A, D312A, N315A, K317A, E318A, K320A, K322A, S324A, K326A, A327Q, P329A, A330Q, P331A, E333A, K334A, T335A, S337A, K338A, K340A, Q342A, R344A, E345A, Q347A, R355A, E356A, M358A, T359A, K360A, N361A, Q362A, Y373A, S375A, D376A, A378Q, E380A, E382A, S383A, N384A, Q386A, E388A, N389A, N390A, Y391F, K392A, L398A, S400A, D401A, D413A, K414A, R416A, Q418A, Q419A, N421A, V422A, S424A, E430A, N434A, T437A, Q438A, K439A, S440A, S444A, and K447A, where for example P238A represents wild type proline substituted by alanine at position number 238. As an example, a specific embodiment incorporates the N297A mutation, removing a highly conserved N-glycosylation site. In addition to alanine other amino acids can be substituted for the wild type amino acids at the positions specified above. Mutations can be introduced singly into Fc giving rise to more than one hundred Fc regions distinct from the native Fc. Additionally, combinations of two, three, or more of these individual mutations can be introduced together, giving rise to hundreds more Fc regions.

Certain of the above mutations can confer new functionality upon the Fc region or FcRn binding partner. For example, one embodiment incorporates N297A, removing a highly conserved N-glycosylation site. The effect of this mutation is to reduce immunogenicity, thereby enhancing circulating half-life of the Fc region, and to render the Fc region incapable of binding to FcγRI, FcγRIIA, FcγRIIB, and FcγRIIIA, without compromising affinity for FcRn (Routledge et al. 1995, Transplantation 60:847; Friend et al. 1999, Transplantation 68:1632; Shields et al. 1995, J. Biol. Chem. 276:6591). As a further example of new functionality arising from mutations described above affinity for FcRn can be increased beyond that of wild type in some instances. This increased affinity can reflect an increased "on" rate, a decreased "off" rate or both an increased "on" rate and a decreased "off" rate. Examples of mutations believed to impart an increased affinity for FcRn include, but not limited to, T256A, T307A, E380A, and N434A (Shields et al. 2001, J. Biol. Chem. 276:6591).

Additionally, at least three human Fc gamma receptors appear to recognize a binding site on IgG within the lower hinge region, generally amino acids 234-237. Therefore, another example of new functionality and potential decreased immunogenicity can arise from mutations of this region, as for example by replacing amino acids 233-236 of human IgG1 "ELLG" (SEQ ID NO:29) to the corresponding sequence from IgG2 "PVA" (with one amino acid deletion). It has been shown that FcγRI, FcγRII, and FcγRIII, which mediate various effector functions will not bind to IgG1 when such mutations have been introduced. Ward and Ghetie 1995, Therapeutic Immunology 2:77 and Armour et al. 1999, Eur. J. Immunol. 29:2613.

In another embodiment, the immunoglobulin constant region or a portion thereof comprises an amino acid sequence in the hinge region or a portion thereof that forms one or more disulfide bonds with a second immunoglobulin constant region or a portion thereof. The second immunoglobulin constant region or a portion thereof an be linked to a second polypeptide, bringing the FIX protein and the second polypeptide together. In some embodiments, the second polypeptide is an enhancer moiety. As used herein, the term "enhancer moiety" refers to a molecule, fragment thereof or a component of a polypeptide which is capable of enhancing the procoagulant activity of FIX. The enhancer moiety can be a cofactor, such as soluble tissue factor (sTF), or a procoagulant peptide. Thus, upon activation of FIX, the enhancer moiety is available to enhance FIX activity.

In certain embodiments, a FIX protein of the invention comprises an amino acid substitution to an immunoglobulin constant region or a portion thereof (e.g., Fc variants), which alters the antigen-independent effector functions of the Ig constant region, in particular the circulating half-life of the protein.

2. scFc Regions

In another aspect, a heterologous moiety comprises a scFc (single chain Fc) region. In one embodiment, an isolated nucleic acid molecule of the invention further comprises a heterologous nucleic acid sequence that encodes a scFc region. The scFc region comprises at least two immunoglobulin constant regions or portions thereof (e.g., Fc moieties or domains (e.g., 2, 3, 4, 5, 6, or more Fc moieties or domains)) within the same linear polypeptide chain that are capable of folding (e.g., intramolecularly or intermolecularly folding) to form one functional scFc region which is linked by an Fc peptide linker. For example, in one embodiment, a polypeptide of the invention is capable of binding, via its scFc region, to at least one Fc receptor (e.g. an FcRn, an FcγR receptor (e.g., FcγRIII), or a complement protein (e.g. Clq)) in order to improve half-life or trigger an immune effector function (e.g., antibody-dependent cytotoxicity (ADCC), phagocytosis, or complement-dependent cytotoxicity (CDCC) and/or to improve manufacturability).

3. CTP

In another aspect, a heterologous moiety comprises one C-terminal peptide (CTP) of the β subunit of human chorionic gonadotropin or fragment, variant, or derivative thereof. One or more CTP peptides inserted into a recombinant protein is known to increase the in vivo half-life of that protein. See, e.g., U.S. Pat. No. 5,712,122, incorporated by reference herein in its entirety.

Exemplary CTP peptides include DPRFQDSSSSKAPPPSLPSPSRLPGPSDTPIL (SEQ ID NO:17) or SSSSKAPPPSLPSPSRLPGPSDTPILPQ. (SEQ ID NO:18). See, e.g., U.S. Patent Application Publication No. US 2009/0087411 A1, incorporated by reference.

4. XTEN Sequence

In some embodiments, a heterologous moiety comprises one or more XTEN sequences, fragments, variants, or derivatives thereof. As used here "XTEN sequence" refers to extended length polypeptides with non-naturally occurring, substantially non-repetitive sequences that are composed mainly of small hydrophilic amino acids, with the sequence having a low degree or no secondary or tertiary structure under physiologic conditions. As a heterologous moiety, XTENs can serve as a half-life extension moiety. In addition, XTEN can provide desirable properties including but are not limited to enhanced pharmacokinetic parameters and solubility characteristics.

The incorporation of a heterologous moiety comprising an XTEN sequence into a protein of the invention can confer to the protein one or more of the following advantageous properties: conformational flexibility, enhanced aqueous solubility, high degree of protease resistance, low immunogenicity, low binding to mammalian receptors, or increased hydrodynamic (or Stokes) radii.

In certain aspects, an XTEN sequence can increase pharmacokinetic properties such as longer in vivo half-life or increased area under the curve (AUC), so that a protein of the invention stays in vivo and has procoagulant activity for an increased period of time compared to a protein with the same but without the XTEN heterologous moiety.

Examples of XTEN sequences that can be used as heterologous moieties in chimeric proteins of the invention are disclosed, e.g., in U.S. Patent Publication Nos. 2010/0239554 A1, 2010/0323956 A1, 2011/0046060 A1, 2011/0046061 A1, 2011/0077199 A1, or 2011/0172146 A1, or International Patent Publication Nos. WO 2010091122 A1, WO 2010144502 A2, WO 2010144508 A1, WO 2011028228 A1, WO 2011028229 A1, WO 2011028344 A2, US2012/0178691 A1, WO2013/122617 A2, each of which is incorporated by reference herein in its entirety.

Exemplary XTEN sequences that can be used as heterologous moieties in chimeric protein of the invention include XTEN AE42-4 (SEQ ID NO:30, encoded by SEQ ID NO:31), XTEN 144-2A (SEQ ID NO:32, encoded by SEQ ID NO:33), XTEN A144-3B (SEQ ID NO:34, encoded by SEQ ID NO:35), XTEN AE144-4A (SEQ ID NO:36, encoded by SEQ ID NO:37), XTEN AE144-5A (SEQ ID NO:38, encoded by SEQ ID NO:39), XTEN AE144-6B (SEQ ID NO:40, encoded by SEQ ID NO:41), XTEN AG144-1 (SEQ ID NO:42, encoded by SEQ ID NO:43), XTEN AG144-A (SEQ ID NO:44, encoded by SEQ ID NO:45), XTEN AG144-B (SEQ ID NO:46, encoded by SEQ ID NO:47), XTEN AG144-C(SEQ ID NO:48, encoded by SEQ ID NO:49), and XTEN AG144-F (SEQ ID NO:50, encoded by SEQ ID NO:51).

5. Albumin or Fragment, Derivative, or Variant Thereof

In some embodiments, a heterologous moiety comprises albumin or a functional fragment thereof. Human serum albumin (HSA, or HA), a protein of 609 amino acids in its full-length form, is responsible for a significant proportion of the osmotic pressure of serum and also functions as a carrier of endogenous and exogenous ligands. The term "albumin" as used herein includes full-length albumin or a functional fragment, variant, derivative, or analog thereof. Examples of albumin or the fragments or variants thereof are disclosed in US Pat. Publ. Nos. 2008/0194481A1, 2008/0004206 A1, 2008/0161243 A1, 2008/0261877 A1, or 2008/0153751 A1 or PCT Appl. Publ. Nos. 2008/033413 A2, 2009/058322 A1, or 2007/021494 A2, which are incorporated herein by reference in their entireties.

In one embodiment, the FIX protein of the invention comprises albumin, a fragment, or a variant thereof which is further linked to a second heterologous moiety selected from the group consisting of an immunoglobulin constant region or portion thereof (e.g., an Fc region), a PAS sequence, HES, and PEG.

6. Albumin-Binding Moiety

In certain embodiments, the heterologous moiety is an albumin-binding moiety, which comprises an albumin-binding peptide, a bacterial albumin-binding domain, an albumin-binding antibody fragment, or any combinations thereof.

For example, the albumin-binding protein can be a bacterial albumin-binding protein, an antibody or an antibody fragment including domain antibodies (see U.S. Pat. No. 6,696,245). An albumin-binding protein, for example, can be a bacterial albumin-binding domain, such as the one of streptococcal protein G (Konig, T. and Skerra, A. (1998) *J. Immunol. Methods* 218, 73-83). Other examples of albumin-binding peptides that can be used as conjugation partner are, for instance, those having a Cys-Xaa$_1$-Xaa$_2$-Xaa$_3$-Xaa$_4$-Cys consensus sequence, wherein Xaa$_1$ is Asp, Asn, Ser, Thr, or Trp; Xaa$_2$ is Asn, Gin, H is, Ile, Leu, or Lys; Xaa$_3$ is Ala, Asp, Phe, Trp, or Tyr; and Xaa$_4$ is Asp, Gly, Leu, Phe, Ser, or Thr as described in US patent application 2003/0069395 or Dennis et al. (Dennis et al. (2002) *J. Biol. Chem.* 277, 35035-35043).

Domain 3 from streptococcal protein G, as disclosed by Kraulis et al., FEBS Lett. 378:190-194 (1996) and Linhult et al., Protein Sci. 11:206-213 (2002) is an example of a bacterial albumin-binding domain. Examples of albumin-binding peptides include a series of peptides having the core sequence DICLPRWGCLW (SEQ ID NO:19). See, e.g., Dennis et al., J. Biol. Chem. 2002, 277: 35035-35043 (2002). Examples of albumin-binding antibody fragments are disclosed in Muller and Kontermann, Curr. Opin. Mol. Ther. 9:319-326 (2007); Roovers et al., Cancer Immunol. Immunother. 56:303-317 (2007), and Holt et al., Prot. Eng. Design Sci., 21:283-288 (2008), which are incorporated herein by reference in their entireties. An example of such albumin-binding moiety is 2-(3-maleimidopropanamido)-6-(4-(4-iodophenyl)butanamido) hexanoate ("Albu" tag) as disclosed by Trussel et al., Bioconjugate Chem. 20:2286-2292 (2009).

Fatty acids, in particular long chain fatty acids (LCFA) and long chain fatty acid-like albumin-binding compounds can be used to extend the in vivo half-life of FIX proteins of the invention. An example of a LCFA-like albumin-binding compound is 16-(1-(3-(9-(((2,5-dioxopyrrolidin-1-yloxy) carbonyloxy)-methyl)-7-sulfo-9H-fluoren-2-ylamino)-3-oxopropyl)-2,5-dioxopyrrolidin-3-ylthio) hexadecanoic acid (see, e.g., WO 2010/140148).

7. PAS Sequence

In other embodiments, the heterologous moiety is a PAS sequence. A PAS sequence, as used herein, means an amino acid sequence comprising mainly alanine and serine residues or comprising mainly alanine, serine, and proline residues, the amino acid sequence forming random coil conformation under physiological conditions. Accordingly, the PAS sequence is a building block, an amino acid polymer, or a sequence cassette comprising, consisting essentially of, or consisting of alanine, serine, and proline which can be used as a part of the heterologous moiety in the chimeric protein. Yet, the skilled person is aware that an amino acid polymer also can form random coil conformation when residues other than alanine, serine, and proline are added as a minor constituent in the PAS sequence. The term "minor constituent" as used herein means that amino acids other than alanine, serine, and proline can be added in the PAS sequence to a certain degree, e.g., up to about 12%, i.e., about 12 of 100 amino acids of the PAS sequence, up to about 10%, i.e. about 10 of 100 amino acids of the PAS sequence, up to about 9%, i.e., about 9 of 100 amino acids, up to about 8%, i.e., about 8 of 100 amino acids, about 6%, i.e., about 6 of 100 amino acids, about 5%, i.e., about 5 of 100 amino acids, about 4%, i.e., about 4 of 100 amino acids, about 3%, i.e., about 3 of 100 amino acids, about 2%, i.e., about 2 of 100 amino acids, about 1%, i.e., about 1 of 100 of the amino acids. The amino acids different from alanine, serine and proline can be selected from the group consisting of Arg, Asn, Asp, Cys, Gin, Glu, Gly, His, Ile, Leu, Lys, Met, Phe, Thr, Trp, Tyr, and Val.

Under physiological conditions, the PAS sequence stretch forms a random coil conformation and thereby can mediate an increased in vivo and/or in vitro stability to the FIX protein. Since the random coil domain does not adopt a stable structure or function by itself, the biological activity mediated by the FIX protein is essentially preserved. In other embodiments, the PAS sequences that form random coil domain are biologically inert, especially with respect to proteolysis in blood plasma, immunogenicity, isoelectric point/electrostatic behaviour, binding to cell surface receptors or internalisation, but are still biodegradable, which provides clear advantages over synthetic polymers such as PEG.

Non-limiting examples of the PAS sequences forming random coil conformation comprise an amino acid sequence selected from the group consisting of ASPAAPA-PASPAAPAPSAPA (SEQ ID NO: 20), AAPASPAPAAP- SAPAPAAPS (SEQ ID NO: 21), APSSPSP-SAPSSPSPASPSS (SEQ ID NO: 22), APSSPSPSAPSSPSPASPS (SEQ ID NO: 23), SSP-SAPSPSSPASPSPSSPA (SEQ ID NO: 24), AASPAAPSAP-PAAASPAAPSAPPA (SEQ ID NO: 25) and ASAAAPAAASAAASAPSAAA (SEQ ID NO: 26) or any combinations thereof. Additional examples of PAS sequences are known from, e.g., US Pat. Publ. No. 2010/0292130 A1 and PCT Appl. Publ. No. WO 2008/155134 A1.

8. HAP Sequence

In certain embodiments, the heterologous moiety is a glycine-rich homo-amino-acid polymer (HAP). The HAP sequence can comprise a repetitive sequence of glycine, which has at least 50 amino acids, at least 100 amino acids, 120 amino acids, 140 amino acids, 160 amino acids, 180 amino acids, 200 amino acids, 250 amino acids, 300 amino acids, 350 amino acids, 400 amino acids, 450 amino acids, or 500 amino acids in length. In one embodiment, the HAP sequence is capable of extending half-life of a moiety fused to or linked to the HAP sequence. Non-limiting examples of the HAP sequence includes, but are not limited to (Gly)$_n$, (Gly$_4$Ser)$_n$, or S(Gly$_4$Ser)$_n$, wherein n is 1, 2, 3, 4, 5, 6, 7, 8, 9, 10, 11, 12, 13, 14, 15, 16, 17, 18, 19, or 20. In one embodiment, n is 20, 21, 22, 23, 24, 25, 26, 26, 28, 29, 30, 31, 32, 33, 34, 35, 36, 37, 38, 39, or 40. In another embodiment, n is 50, 60, 70, 80, 90, 100, 110, 120, 130, 140, 150, 160, 170, 180, 190, or 200.

9. Transferrin or Fragment Thereof

In certain embodiments, the heterologous moiety is transferrin or a fragment thereof. Any transferrin can be used to make the FIX proteins of the invention. As an example, wild-type human TF (TF) is a 679 amino acid protein, of approximately 75 KDa (not accounting for glycosylation), with two main domains, N (about 330 amino acids) and C (about 340 amino acids), which appear to originate from a gene duplication. See GenBank accession numbers NM001063, XM002793, M12530, XM039845, XM 039847 and S95936 (www.ncbi.nlm.nih.gov/), all of which are herein incorporated by reference in their entirety. Transferrin comprises two domains, N domain and C domain. N domain comprises two subdomains, N1 domain and N2 domain, and C domain comprises two subdomains, C1 domain and C2 domain.

In one embodiment, the transferrin heterologous moiety includes a transferrin splice variant. In one example, a transferrin splice variant can be a splice variant of human transferrin, e.g., Genbank Accession AAA61140. In another embodiment, the transferrin portion of the chimeric protein includes one or more domains of the transferrin sequence, e.g., N domain, C domain, N1 domain, N2 domain, C1 domain, C2 domain or any combinations thereof.

10. Clearance Receptors

In certain embodiments, the heterologous moiety is a clearance receptor, fragment, variant, or derivative thereof. LRP1 is a 600 kDa integral membrane protein that is implicated in the receptor-mediate clearance of a variety of proteins, such as Factor X. See, e.g., Narita et al., Blood 91:555-560 (1998).

11. Linker Moieties

In certain embodiments, the heterologous moiety is a peptide linker.

As used herein, the terms "peptide linkers" or "linker moieties" refer to a peptide or polypeptide sequence (e.g., a synthetic peptide or polypeptide sequence) which connects two domains in a linear amino acid sequence of a polypeptide chain.

In some embodiments, heterologous nucleotide sequences encoding peptide linkers can be inserted between the optimized FIX polynucleotide sequences of the invention and a heterologous nucleotide sequence encoding, for example, one of the heterologous moieties described above, such as albumin. Peptide linkers can provide flexibility to the chimeric polypeptide molecule. Linkers are not typically cleaved, however such cleavage can be desirable. In one embodiment, these linkers are not removed during processing.

A type of linker which can be present in a chimeric protein of the invention is a protease cleavable linker which comprises a cleavage site (i.e., a protease cleavage site substrate, e.g., a factor XIa, Xa, or thrombin cleavage site) and which can include additional linkers on either the N-terminal of C-terminal or both sides of the cleavage site. These cleavable linkers when incorporated into a construct of the invention result in a chimeric molecule having a heterologous cleavage site.

In one embodiment, a FIX polypeptide of the instant invention comprises two or more Fc domains or moieties linked via a cscFc linker to form an Fc region comprised in a single polypeptide chain. The cscFc linker is flanked by at least one intracellular processing site, i.e., a site cleaved by an intracellular enzyme. Cleavage of the polypeptide at the at least one intracellular processing site results in a polypeptide which comprises at least two polypeptide chains.

Other peptide linkers can optionally be used in a construct of the invention, e.g., to connect an FIX protein to an Fc region. Some exemplary linkers that can be used in connection with the invention include, e.g., polypeptides comprising GlySer amino acids described in more detail below.

In one embodiment, the peptide linker is synthetic, i.e., non-naturally occurring. In one embodiment, a peptide linker includes peptides (or polypeptides) (which can or can not be naturally occurring) which comprise an amino acid sequence that links or genetically fuses a first linear sequence of amino acids to a second linear sequence of amino acids to which it is not naturally linked or genetically fused in nature. For example, in one embodiment the peptide linker can comprise non-naturally occurring polypeptides which are modified forms of naturally occurring polypeptides (e.g., comprising a mutation such as an addition, substitution or deletion). In another embodiment, the peptide linker can comprise non-naturally occurring amino acids. In another embodiment, the peptide linker can comprise naturally occurring amino acids occurring in a linear sequence that does not occur in nature. In still another embodiment, the peptide linker can comprise a naturally occurring polypeptide sequence.

For example, in certain embodiments, a peptide linker can be used to fuse identical Fc moieties, thereby forming a homodimeric scFc region. In other embodiments, a peptide linker can be used to fuse different Fc moieties (e.g. a wild-type Fc moiety and an Fc moiety variant), thereby forming a heterodimeric scFc region.

In another embodiment, a peptide linker comprises or consists of a gly-ser linker. In one embodiment, a scFc or cscFc linker comprises at least a portion of an immunoglobulin hinge and a gly-ser linker. As used herein, the term "gly-ser linker" refers to a peptide that consists of glycine and serine residues. In certain embodiments, said gly-ser linker can be inserted between two other sequences of the peptide linker. In other embodiments, a gly-ser linker is attached at one or both ends of another sequence of the peptide linker. In yet other embodiments, two or more gly-ser linker are incorporated in series in a peptide linker.

In one embodiment, a peptide linker of the invention comprises at least a portion of an upper hinge region (e.g., derived from an IgG1, IgG2, IgG3, or IgG4 molecule), at least a portion of a middle hinge region (e.g., derived from an IgG1, IgG2, IgG3, or IgG4 molecule) and a series of gly/ser amino acid residues.

Peptide linkers of the invention are at least one amino acid in length and can be of varying lengths. In one embodiment, a peptide linker of the invention is from about 1 to about 50 amino acids in length. As used in this context, the term "about" indicates +/−two amino acid residues. Since linker length must be a positive integer, the length of from about 1 to about 50 amino acids in length, means a length of from 1-3 to 48-52 amino acids in length. In another embodiment, a peptide linker of the invention is from about 10 to about 20 amino acids in length. In another embodiment, a peptide linker of the invention is from about 15 to about 50 amino acids in length. In another embodiment, a peptide linker of the invention is from about 20 to about 45 amino acids in length. In another embodiment, a peptide linker of the invention is from about 15 to about 35 or about 20 to about 30 amino acids in length. In another embodiment, a peptide linker of the invention is from about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 40, 50, 60, 70, 80, 90, 100, 500, 1000, or 2000 amino acids in length. In one embodiment, a peptide linker of the invention is 20 or 30 amino acids in length.

In some embodiments, the peptide linker can comprise at least two, at least three, at least four, at least five, at least 10, at least 20, at least 30, at least 40, at least 50, at least 60, at least 70, at least 80, at least 90, or at least 100 amino acids. In other embodiments, the peptide linker can comprise at least 200, at least 300, at least 400, at least 500, at least 600, at least 700, at least 800, at least 900, or at least 1,000 amino acids. In some embodiments, the peptide linker can comprise at least about 10, 20, 30, 40, 50, 60, 70, 80, 90, 100, 150, 200, 300, 400, 500, 600, 700, 800, 900, 1000, 1100, 1200, 1300, 1400, 1500, 1600, 1700, 1800, 1900, or 2000 amino acids. The peptide linker can comprise 1-5 amino acids, 1-10 amino acids, 1-20 amino acids, 10-50 amino acids, 50-100 amino acids, 100-200 amino acids, 200-300 amino acids, 300-400 amino acids, 400-500 amino acids, 500-600 amino acids, 600-700 amino acids, 700-800 amino acids, 800-900 amino acids, or 900-1000 amino acids.

Peptide linkers can be introduced into polypeptide sequences using techniques known in the art. Modifications can be confirmed by DNA sequence analysis. Plasmid DNA can be used to transform host cells for stable production of the polypeptides produced.

Monomer-Dimer Hybrids

In some embodiments, the isolated nucleic acid molecules of the invention which further comprise a heterologous nucleotide sequence encode a monomer-dimer hybrid molecule comprising FIX.

The term "monomer-dimer hybrid" used herein refers to a chimeric protein comprising a first polypeptide chain and a second polypeptide chain, which are associated with each other by a disulfide bond, wherein the first chain comprises Factor IX and a first Fc region and the second chain comprises, consists essentially of, or consists of a second Fc region without the FIX. The monomer-dimer hybrid construct thus is a hybrid comprising a monomer aspect having only one clotting factor and a dimer aspect having two Fc regions.

Transcription Control Sequences

In some embodiments, the isolated nucleic acid molecules of the invention are operatively linked to at least one transcription control sequences. A transcription control sequences as used herein is any regulatory nucleotide sequence, such as a promoter sequence or promoter-enhancer combination, which facilitates the efficient transcription and translation of the coding nucleic acid to which it is operably linked. The gene expression control sequence can, for example, be a mammalian or viral promoter, such as a constitutive or inducible promoter. Constitutive mammalian promoters include, but are not limited to, the promoters for the following genes: hypoxanthine phosphoribosyl transferase (HPRT), adenosine deaminase, pyruvate kinase, beta-actin promoter, and other constitutive promoters. Exemplary viral promoters which function constitutively in eukaryotic cells include, for example, promoters from the cytomegalovirus (CMV), simian virus (e.g., SV40), papilloma virus, adenovirus, human immunodeficiency virus (HIV), Rous sarcoma virus, cytomegalovirus, the long terminal repeats (LTR) of Moloney leukemia virus, and other retroviruses, and the thymidine kinase promoter of herpes simplex virus. Other constitutive promoters are known to those of ordinary skill in the art. The promoters useful as gene expression sequences of the invention also include inducible promoters. Inducible promoters are expressed in the presence of an inducing agent. For example, the metallothionein promoter is induced to promote transcription and translation in the presence of certain metal ions. Other inducible promoters are known to those of ordinary skill in the art.

In general, the transcription control sequences shall include, as necessary, 5' non-transcribing and 5' non-translating sequences involved with the initiation of transcription and translation, respectively, such as a TATA box, capping sequence, CAAT sequence, and the like. Especially, such 5' non-transcribing sequences will include a promoter region which includes a promoter sequence for transcriptional control of the operably joined coding nucleic acid. The gene expression sequences optionally include enhancer sequences or upstream activator sequences as desired.

Vectors

The invention also provides vectors comprising the isolated nucleic acid molecules of the invention. Suitable vectors include expression vectors, viral vectors, and plasmid vectors.

As used herein, an expression vector refers to any nucleic acid construct which contains the necessary elements for the transcription and translation of an inserted coding sequence, or in the case of an RNA viral vector, the necessary elements for replication and translation, when introduced into an appropriate host cell. Expression vectors can include plasmids, phagemids, viruses, and derivatives thereof.

Expression vectors of the invention will include optimized polynucleotides encoding the FIX protein described herein. In one embodiment, the optimized coding sequences for the FIX protein is operably linked to an expression control sequence. As used herein, two nucleic acid sequences are operably linked when they are covalently linked in such a way as to permit each component nucleic acid sequence to retain its functionality. A coding sequence and a gene expression control sequence are said to be operably linked when they are covalently linked in such a way as to place the expression or transcription and/or translation of the coding sequence under the influence or control of the gene expression control sequence. Two DNA sequences are said to be operably linked if induction of a promoter in the 5' gene expression sequence results in the transcription of the coding sequence and if the nature of the linkage between the two DNA sequences does not (1) result in the introduction of a frame-shift mutation, (2) interfere with the ability of the promoter region to direct the transcription of the coding sequence, or (3) interfere with the ability of the corresponding RNA transcript to be translated into a protein. Thus, a gene expression sequence would be operably linked to a coding nucleic acid sequence if the gene expression sequence were capable of effecting transcription of that coding nucleic acid sequence such that the resulting transcript is translated into the desired protein or polypeptide.

Viral vectors include, but are not limited to, nucleic acid sequences from the following viruses: retrovirus, such as Moloney murine leukemia virus, Harvey murine sarcoma virus, murine mammary tumor virus, and Rous sarcoma virus; adenovirus, adeno-associated virus; SV40-type viruses; polyomaviruses; Epstein-Barr viruses; papilloma viruses; herpes virus; vaccinia virus; polio virus; and RNA virus such as a retrovirus. One can readily employ other vectors well-known in the art. Certain viral vectors are based on non-cytopathic eukaryotic viruses in which non-essential genes have been replaced with the gene of interest. Non-cytopathic viruses include retroviruses, the life cycle of which involves reverse transcription of genomic viral RNA into DNA with subsequent proviral integration into host cellular DNA. Retroviruses have been approved for human gene therapy trials. Most useful are those retroviruses that are replication-deficient (i.e., capable of directing synthesis of the desired proteins, but incapable of manufacturing an infectious particle). Such genetically altered retroviral expression vectors have general utility for the high efficiency transduction of genes in vivo. Standard protocols for producing replication-deficient retroviruses (including the steps of incorporation of exogenous genetic material into a plasmid, transfection of a packaging cell line with plasmid, production of recombinant retroviruses by the packaging cell line, collection of viral particles from tissue culture media, and infection of the target cells with viral particles) are provided in Kriegler, M., Gene Transfer and Expression, A Laboratory Manual, W.H. Freeman Co., New York (1990) and Murry, E. J., Methods in Molecular Biology, Vol. 7, Humana Press, Inc., Cliffton, N.J. (1991).

In one embodiment, the virus is an adeno-associated virus, a double-stranded DNA virus. The adeno-associated virus can be engineered to be replication-deficient and is capable of infecting a wide range of cell types and species. It further has advantages such as heat and lipid solvent stability; high transduction frequencies in cells of diverse lineages, including hematopoietic cells; and lack of superinfection inhibition thus allowing multiple series of transductions. Reportedly, the adeno-associated virus can integrate into human cellular DNA in a site-specific manner, thereby minimizing the possibility of insertional mutagenesis and variability of inserted gene expression characteristic of retroviral infection. In addition, wild-type adeno-associated virus infections have been followed in tissue culture for greater than 100 passages in the absence of selective pressure, implying that the adeno-associated virus genomic integration is a relatively stable event. The adeno-associated virus can also function in an extrachromosomal fashion.

In another embodiment, the viral vector is an adeno-associated virus (AAV) that has been manipulated to carry a polynucleotide encoding a FIX protein as disclosed herein. General methods for obtaining recombinant AAVs (rAAVs) have been disclosed. See, for example, U.S. Pat. No. 8,734, 809, 2013/0195801 as well as the references cited therein. In some embodiments, a rAAV vector comprises one or more AAV inverted terminal repeats (ITRs) and a transgene of interest (e.g., an optimized FIX polynucleotide sequence). In certain embodiments, the methods of making rAAV involve culturing a desired host cell which contains a nucleic acid sequence encoding an AAV capsid protein or fragment thereof; a functional rep gene; a rAAV vector composed of, AAV inverted terminal repeats (ITRs) and a transgene of interest; and sufficient helper functions to permit packaging of the recombinant AAV vector into the AAV capsid proteins. Materials and methods for performing these and related procedures have been disclosed, for example, in U.S. Pat. No. 8,734,809, 2013/0195801, PCT/US1997/015692, PCT/US2002/033692, PCT/US2002/033630, WO2007/148971, WO00/20561, WO03/042361, and WO2007/04670.

One or more of different AAV vector sequences derived from nearly any serotype can be used in accord with the present invention. Choice of a particular AAV vector sequence will be guided by known parameters such as tropism of interest, required vector yields, etc. Generally, the AAV serotypes have genomic sequences of significant homology at the amino acid and the nucleic acid levels, provide a related set of genetic functions, produce virions which are related, and replicate and assemble similarly. For the genomic sequence of the various AAV serotypes and an overview of the genomic similarities see e.g. GenBank Accession number U89790; GenBank Accession number J01901; GenBank Accession number AF043303; GenBank Accession number AF085716; Chlorini et al. (1997, J. Vir. 71: 6823-33); Srivastava et al. (1983, J. Vir. 45:555-64); Chlorini et al. (1999, J. Vir. 73:1309-1319); Rutledge et al. (1998, J. Vir. 72:309-319); and Wu et al. (2000, J. Vir. 74: 8635-47). AAV serotypes 1, 2, 3, 4 and 5 are an illustrative source of AAV nucleotide sequences for use in the context of the present invention. AAV6, AAV7, AAV8 or AAV9 or newly developed AAV-like particles obtained by e.g. capsid shuffling techniques and AAV capsid libraries, or from newly designed, developed or evolved ITR's are also suitable for certain invention applications. See Dalkara, D et al. (2013), Sci Transl. Med. 5(189): 189ra76; Kotterman, M A Nat. Rev. Genet. (2014) 15(7):455.

In certain embodiments however, AAV vectors with significant tropism to the liver and related tissues will be of interest for expressing the FIX proteins disclosed herein. Non-limiting examples include AAV serotypes 1, 2, 6 and 8. See e.g., Torres-Torranteras et al. (2014) 22: 901 and references cited therein.

In other embodiments, the vector is derived from lentivirus. In certain embodiments, the vector is a vector of a recombinant lentivirus capable of infecting non-dividing cells.

The lentiviral genome and the proviral DNA typically have the three genes found in retroviruses: gag, pol and env, which are flanked by two long terminal repeat (LTR) sequences. The gag gene encodes the internal structural (matrix, capsid and nucleocapsid) proteins; the pol gene encodes the RNA-directed DNA polymerase (reverse transcriptase), a protease and an integrase; and the env gene encodes viral envelope glycoproteins. The 5' and 3' LTR's serve to promote transcription and polyadenylation of the virion RNA's. The LTR contains all other cis-acting sequences necessary for viral replication. Lentiviruses have additional genes including vif, vpr, tat, rev, vpu, nef and vpx (in HIV-1, HIV-2 and/or SIV).

Adjacent to the 5' LTR are sequences necessary for reverse transcription of the genome (the tRNA primer binding site) and for efficient encapsidation of viral RNA into particles (the Psi site). If the sequences necessary for encapsidation (or packaging of retroviral RNA into infectious virions) are missing from the viral genome, the cis defect prevents encapsidation of genomic RNA.

However, the resulting mutant remains capable of directing the synthesis of all virion proteins. The invention provides a method of producing a recombinant lentivirus capable of infecting a non-dividing cell comprising transfecting a suitable host cell with two or more vectors carrying the packaging functions, namely gag, pol and env, as well as rev and tat. As will be disclosed hereinbelow, vectors lacking a functional tat gene are desirable for certain applications. Thus, for example, a first vector can provide a nucleic acid encoding a viral gag and a viral pol and another vector can provide a nucleic acid encoding a viral env to produce a packaging cell. Introducing a vector providing a heterologous gene, herein identified as a transfer vector, into that packaging cell yields a producer cell which releases infectious viral particles carrying the foreign gene of interest.

According to the above-indicated configuration of vectors and foreign genes, the second vector can provide a nucleic acid encoding a viral envelope (env) gene. The env gene can be derived from nearly any suitable virus, including retroviruses. In some embodiments, the env protein is an amphotropic envelope protein which allows transduction of cells of human and other species.

Examples of retroviral-derived env genes include, but are not limited to: Moloney murine leukemia virus (MoMuLV or MMLV), Harvey murine sarcoma virus (HaMuSV or HSV), murine mammary tumor virus (MuMTV or MMTV), gibbon ape leukemia virus (GaLV or GALV), human immunodeficiency virus (HIV) and Rous sarcoma virus (RSV). Other env genes such as Vesicular stomatitis virus (VSV) protein G (VSV G), that of hepatitis viruses and of influenza also can be used.

The vector providing the viral env nucleic acid sequence is associated operably with regulatory sequences described elsewhere herein.

In certain embodiments, the vector includes a lentiviral vector in which the HIV virulence genes env, vif, vpr, vpu and nef were deleted without compromising the ability of the vector to transduce non-dividing cells.

In some embodiments, the vector includes a lentiviral vector which comprises a deletion of the U3 region of the 3' LTR. The deletion of the U3 region can be the complete deletion or a partial deletion.

In some embodiments, the lentiviral vector of the invention comprising the FIX nucleotide sequence described herein can be transfected in a cell with (a) a first nucleotide sequence comprising a gag, a pol, or gag and pol genes and (b) a second nucleotide sequence comprising a heterologous env gene; wherein the lentiviral vector lacks a functional tat gene. In other embodiments, the cell is further transfected with a fourth nucleotide sequence comprising a rev gene. In certain embodiments, the lentiviral vector lacks functional genes selected from vif, vpr, vpu, vpx and nef, or a combination thereof.

In certain embodiments, a lentiviral vector comprises one or more nucleotide sequences encoding a gag protein, a Rev-response element, a central polypurine track (cPPT), or any combination thereof.

Examples of the lentiviral vectors are disclosed in WO9931251, WO9712622, WO9817815, WO9817816, and WO9818934, which are incorporated herein by reference in their entireties.

Other vectors include plasmid vectors. Plasmid vectors have been extensively described in the art and are well-known to those of skill in the art. See, e.g., Sambrook et al., Molecular Cloning: A Laboratory Manual, Second Edition, Cold Spring Harbor Laboratory Press, 1989. In the last few years, plasmid vectors have been found to be particularly advantageous for delivering genes to cells in vivo because of their inability to replicate within and integrate into a host genome. These plasmids, however, having a promoter compatible with the host cell, can express a peptide from a gene operably encoded within the plasmid. Some commonly used plasmids available from commercial suppliers include pBR322, pUC 18, pUC 19, various pcDNA plasmids, pRC/CMV, various pCMV plasmids, pSV40, and pBlueScript. Additional examples of specific plasmids include pcDNA3.1, catalog number V79020; pcDNA3.1/hygro, catalog number V87020; pcDNA4/myc-His, catalog number V86320; and pBudCE4.1, catalog number V53220, all from Invitrogen (Carlsbad, Calif.). Other plasmids are well-known to those of ordinary skill in the art. Additionally, plasmids can be custom designed using standard molecular biology techniques to remove and/or add specific fragments of DNA.

Expression Control Element

In some embodiments, the vector of the invention further comprises at least one expression control sequences. A expression control sequences as used herein is any regulatory nucleotide sequence, such as a promoter sequence or promoter-enhancer combination, which facilitates the efficient transcription and translation of the coding nucleic acid to which it is operably linked. The gene expression control sequence can, for example, be a mammalian or viral promoter, such as a constitutive or inducible promoter. Constitutive mammalian promoters include, but are not limited to, the promoters for the following genes: hypoxanthine phosphoribosyl transferase (HPRT), adenosine deaminase, pyruvate kinase, beta-actin promoter, and other constitutive promoters. Exemplary viral promoters which function constitutively in eukaryotic cells include, for example, promoters from the cytomegalovirus (CMV), simian virus (e.g., SV40), papilloma virus, adenovirus, human immunodeficiency virus (HIV), Rous sarcoma virus, cytomegalovirus, the long terminal repeats (LTR) of Moloney leukemia virus, and other retroviruses, and the thymidine kinase promoter of herpes simplex virus. Other constitutive promoters are known to those of ordinary skill in the art. The promoters useful as gene expression sequences of the invention also include inducible promoters. Inducible promoters are expressed in the presence of an inducing agent. For example, the metallothionein promoter is induced to promote transcription and translation in the presence of certain metal ions. Other inducible promoters are known to those of ordinary skill in the art.

In one embodiment, the invention includes expression of a transgene under the control of a tissue specific promoter and/or enhancer. In another embodiment, the promoter or other expression control sequence selectively enhances expression of the transgene in liver cells. Examples of liver specific promoters include, but are not limited to, a mouse thyretin promoter (mTTR), an endogenous human factor iX promoter (F9), human alpha-1-antitrypsin promoter (hAAT), human albumin minimal promoter, and mouse albumin promoter. In a particular embodiment, the promoter comprises a mTTR promoter. The mTTR promoter is described in R. H. Costa et al., 1986, Mol. Cell. Biol. 6:4697.

Expression levels can be further enhanced to achieve therapeutic efficacy using one or more enhancers. One or more enhancers can be provided either alone or together with one or more promoter elements. Typically, the expression control sequence comprises a plurality of enhancer elements and a tissue specific promoter. In one embodiment, an enhancer comprises one or more copies of the α-1-microglobulin/bikunin enhancer (Rouet et al., 1992, J. Biol. Chem. 267:20765-20773; Rouet et al., 1995, Nucleic Acids Res. 23:395-404; Rouet et al., 1998, Biochem. J. 334:577-584; Ill et al., 1997, Blood Coagulation Fibrinolysis 8:S23-S30). In another embodiment, an enhancer is derived from liver specific transcription factor binding sites, such as EBP, DBP, HNF1, HNF3, HNF4, HNF6, with Enhl, comprising HNF1, (sense)-HNF3, (sense)-HNF4, (antisense)-HNF1, (antisense)-HNF6, (sense)-EBP, (antisense)-HNF4 (antisense).

In a particular example, a promoter useful for the invention comprises an ET promoter, which is also known as GenBank No. AY661265. See also Vigna et al., (2005) Molecular Therapy. Vol 11(5): 763 Examples of other suitable vectors and gene regulatory elements are described in WO 02/092134, EP1395293, or U.S. Pat. Nos. 6,808,905, 7,745,179, or 7,179,903, which are incorporated by reference herein in their entireties.

In general, the expression control sequences shall include, as necessary, 5' non-transcribing and 5' non-translating sequences involved with the initiation of transcription and translation, respectively, such as a TATA box, capping sequence, CAAT sequence, and the like. Especially, such 5' non-transcribing sequences will include a promoter region which includes a promoter sequence for transcriptional control of the operably joined coding nucleic acid. The gene expression sequences optionally include enhancer sequences or upstream activator sequences as desired.

Tissue Specific Expression

In certain embodiments, it will be useful to include within the vector one or more miRNA target sequences which, for example, are operably linked to the optimized FIX transgene. Thus, the invention also provides at least one miRNA sequence target operably linked to the optimized FIX nucleotide sequence or otherwise inserted within a vector. More than one copy of an miRNA target sequence included in the vector can increase the effectiveness of the system. Also included are different miRNA target sequences. For example, vectors which express more than one transgene may have the transgene under control of more than one miRNA target sequence, which can be the same or different. The miRNA target sequences can be in tandem, but other arrangements are also included. The transgene expression cassette, containing miRNA target sequences, can also be inserted within the vector in antisense orientation. Antisense orientation can be useful in the production of viral particles to avoid expression of gene products which can otherwise be toxic to the producer cells. In other embodiments, the vector comprises 1, 2, 3, 4, 5, 6, 7 or 8 copies of the same or different miRNA target sequence. However in certain other embodiments, the vector will not include any miRNA target sequence. Choice of whether or not to include an miRNA target sequence (and how many) will be guided by known parameters such as the intended tissue target, the level of expression required, etc.

In one embodiment, the target sequence is an miR-223 target which has been reported to block expression most effectively in myeloid committed progenitors and at least partially in the more primitive HSPC. miR-223 target can block expression in differentiated myeloid cells including granulocytes, monocytes, macrophages, myeloid dendritic cells. miR-223 target can also be suitable for gene therapy applications relying on robust transgene expression in the lymphoid or erythroid lineage. miR-223 target may block expression also very effectively in human HSC.

In another embodiment, the target sequence is an miR142 target (tccataaagt aggaaacact aca (SEQ ID NO: 52)). In one embodiment, the vector comprises 4 copies of miR-142 target sequences. In certain embodiments, the complementary sequence of hematopoietic-specific microRNAs, such as miR-142 (142T), is incorporated into the 3' untranslated region of a vector, e.g., lentiviral vectors (LV), making the transgene-encoding transcript susceptible to miRNA-mediated down-regulation. By this method, transgene expression can be prevented in hematopoietic-lineage antigen presenting cells (APC), while being maintained in non-hematopoietic cells (Brown et al., Nat Med 2006). This strategy can imposes a stringent post-transcriptional control on transgene expression and thus enables stable delivery and long-term expression of transgenes. In some embodiments, miR-142 regulation prevents immune-mediated clearance of transduced cells and/or induce antigen-specific Regulatory T cells (T regs) and mediate robust immunological tolerance to the transgene-encoded antigen.

In some embodiments, the target sequence is an miR181 target. Chen C-Z and Lodish H, Seminars in Immunology (2005) 17(2):155-165 discloses miR-181, a miRNA specifically expressed in B cells within mouse bone marrow (Chen and Lodish, 2005). It also discloses that some human miRNAs are linked to leukemias.

The target sequence can be fully or partially complementary to the miRNA. The term "fully complementary" means that the target sequence has a nucleic acid sequence which is 100% complementary to the sequence of the miRNA which recognizes it. The term "partially complementary" means that the target sequence is only in part complementary to the sequence of the miRNA which recognizes it, whereby the partially complementary sequence is still recognized by the miRNA. In other words, a partially complementary target sequence in the context of the present invention is effective in recognizing the corresponding miRNA and effecting prevention or reduction of transgene expression in cells expressing that miRNA. Examples of the miRNA target sequences are described at WO2007/000668, WO02004/094642, WO2010/055413, or WO2010/125471, which are incorporated herein by reference in their entireties.

Host Cells

The invention also provides host cells comprising the isolated nucleic acid molecules of the invention. As used herein, the term "transformation" shall be used in a broad sense to refer to the introduction of DNA into a recipient host cell that changes the genotype and consequently results in a change in the recipient cell.

"Host cells" refers to cells that have been transformed with vectors constructed using recombinant DNA techniques and encoding at least one heterologous gene. The host cells of the present invention are preferably of mammalian origin; most preferably of human or mouse origin. Those skilled in the art are credited with ability to preferentially determine particular host cell lines which are best suited for their purpose. Exemplary host cell lines include, but are not limited to, CHO, DG44 and DUXB11 (Chinese Hamster Ovary lines, DHFR minus), HELA (human cervical carcinoma), CVI (monkey kidney line), COS (a derivative of CVI with SV40 T antigen), R1610 (Chinese hamster fibroblast) BALBC/3T3 (mouse fibroblast), HAK (hamster kidney line), SP2/O (mouse myeloma), P3.times.63-Ag3.653 (mouse myeloma), BFA-lclBPT (bovine endothelial cells), RAJI (human lymphocyte), PER.C6*, NS0, CAP, BHK21, and HEK 293 (human kidney). Host cell lines are typically available from commercial services, the American Tissue Culture Collection, or from published literature.

Introduction of the isolated nucleic acid molecules of the invention into the host cell can be accomplished by various techniques well known to those of skill in the art. These include, but are not limited to, transfection (including electrophoresis and electroporation), protoplast fusion, calcium phosphate precipitation, cell fusion with enveloped DNA, microinjection, and infection with intact virus. See, Ridgway, A. A. G. "*Mammalian Expression Vectors*" Chapter 24.2, pp. 470-472 Vectors, Rodriguez and Denhardt, Eds. (Butterworths, Boston, Mass. 1988). Most preferably, plasmid introduction into the host is via electroporation. The transformed cells are grown under conditions appropriate to the production of the light chains and heavy chains, and assayed for heavy and/or light chain protein synthesis. Exemplary assay techniques include enzyme-linked immunosorbent assay (ELISA), radioimmunoassay (RIA), or flourescence-activated cell sorter analysis (FACS), immunohistochemistry and the like.

Host cells comprising the isolated nucleic acid molecules of the invention are grown in an appropriate growth medium. As used herein, the term "appropriate growth medium" means a medium containing nutrients required for the growth of cells. Nutrients required for cell growth can include a carbon source, a nitrogen source, essential amino acids, vitamins, minerals, and growth factors. Optionally, the media can contain one or more selection factors. Optionally the media can contain bovine calf serum or fetal calf serum (FCS). In one embodiment, the media contains substantially no IgG. The growth medium will generally select for cells containing the DNA construct by, for example, drug selection or deficiency in an essential nutrient which is complemented by the selectable marker on the DNA construct or co-transfected with the DNA construct. Cultured mammalian cells are generally grown in commercially available serum-containing or serum-free media (e.g., MEM, DMEM, DMEM/F12). In one embodiment, the medium is CDoptiCHO (Invitrogen, Carlsbad, Calif.). In another embodiment, the medium is CD17 (Invitrogen, Carlsbad, Calif.). Selection of a medium appropriate for the particular cell line used is within the level of those ordinary skilled in the art.

Preparation of Polypeptides

The invention also provides a polypeptide encoded by the isolated nucleic acid molecules of the invention. In other embodiments, the polypeptide of the invention is encoded by a vector comprising the isolated nucleic molecules of the invention. In yet other embodiments, the polypeptide of the invention is produced by a host cell comprising the isolated nucleic molecules of the invention.

In other embodiments, the invention also provides a method of producing a polypeptide with FIX activity, comprising culturing a host cell of the invention under conditions whereby a polypeptide with FIX activity is produced, and recovering the polypeptide with FIX activity. In some embodiments, the expression of the polypeptide with FIX activity is increased relative to a host cell cultured under the same conditions but containing a reference nucleotide sequence comprising SEQ ID NO:2, the parental FIX gene sequence.

In other embodiments, the invention provides a method of increasing the expression of a polyepetide with FIX activity comprising culturing a host cell of the invention under conditions whereby a polypeptide with FIX activity is expressed by the nucleic acid molecule, wherein the expression of the polypeptide with FIX activity is increased relative to a host cell cultured under the same conditions comprising a reference nucleic acid molecule comprising SEQ ID NO:2.

In other embodiments, the invention provides a method of improving yield of a polypeptide with FIX activity comprising culturing a host cell under conditions whereby a polypeptide with FIX activity is produced by the nucleic acid molecule, wherein the yield of polypeptide with FIX activity is increased relative to a host cell cultured under the same conditions comprising a reference nucleic acid sequence comprising SEQ ID NO: 2.

A variety of methods are available for recombinantly producing an FIX protein from the optimized nucleic acid molecule of the invention. A polynucleotide of the desired sequence can be produced by de novo solid-phase DNA synthesis or by PCR mutagenesis of an earlier prepared polynucleotide. Oligonucleotide-mediated mutagenesis is one method for preparing a substitution, insertion, deletion, or alteration (e.g., altered codon) in a nucleotide sequence. For example, the starting DNA is altered by hybridizing an oligonucleotide encoding the desired mutation to a single-stranded DNA template. After hybridization, a DNA polymerase is used to synthesize an entire second complementary strand of the template that incorporates the oligonucleotide primer. In one embodiment, genetic engineering, e.g., primer-based PCR mutagenesis, is sufficient to incorporate an alteration, as defined herein, for producing a polynucleotide of the invention.

For recombinant protein production, an optimized polynucleotide sequence of the invention encoding the FIX protein is inserted into an appropriate expression vehicle, i.e., a vector which contains the necessary elements for the transcription and translation of the inserted coding sequence, or in the case of an RNA viral vector, the necessary elements for replication and translation.

The polynucleotide sequence of the invention is inserted into the vector in proper reading frame. The expression vector is then transfected into a suitable target cell which will express the polypeptide. Transfection techniques known in the art include, but are not limited to, calcium phosphate precipitation (Wigler et al. 1978, *Cell* 14: 725) and electroporation (Neumann et al. 1982, *EMBO, J.* 1: 841). A variety of host-expression vector systems can be utilized to express the FIX proteins described herein in eukaryotic cells. In one embodiment, the eukaryotic cell is an animal cell, including mammalian cells (e.g. HEK293 cells, PER.C6®, CHO, BHK, Cos, HeLa cells). A polynucleotide sequence of the invention can also code for a signal sequence that will permit the FIX protein to be secreted. One skilled in the art will understand that while the FIX protein is translated the signal sequence is cleaved by the cell to form the mature protein. Various signal sequences are known in the art, e.g., native factor VII signal sequence, native factor IX signal sequence, and the mouse IgK light chain signal sequence. Alternatively, where a signal sequence is not included the FIX protein can be recovered by lysing the cells.

The FIX protein of the invention can be synthesized in a transgenic animal, such as a rodent, goat, sheep, pig, or cow. The term "transgenic animals" refers to non-human animals that have incorporated a foreign gene into their genome. Because this gene is present in germline tissues, it is passed from parent to offspring. Exogenous genes are introduced into single-celled embryos (Brinster et al. 1985, Proc. Natl. Acad.Sci. USA 82:4438). Methods of producing transgenic animals are known in the art including transgenics that produce immunoglobulin molecules (Wagner et al. 1981, Proc. Natl. Acad. Sci. USA 78: 6376; McKnight et al. 1983, Cell 34: 335; Brinster et al. 1983, Nature 306: 332; Ritchie et al. 1984, Nature 312: 517; Baldassarre et al. 2003, Theriogenology 59: 831; Robl et al. 2003, Theriogenology 59: 107; Malassagne et al. 2003, Xenotransplantation 10 (3): 267).

The expression vectors can encode for tags that permit for easy purification or identification of the recombinantly produced protein. Examples include, but are not limited to, vector pUR278 (Ruther et al. 1983, EMBO J. 2: 1791) in which the FIX protein described herein coding sequence can be ligated into the vector in frame with the lac Z coding region so that a hybrid protein is produced; pGEX vectors can be used to express proteins with a glutathione S-transferase (GST) tag. These proteins are usually soluble and can easily be purified from cells by adsorption to glutathione-agarose beads followed by elution in the presence of free glutathione. The vectors include cleavage sites (e.g., Pre-Cission Protease (Pharmacia, Peapack, N.J.)) for easy removal of the tag after purification.

For the purposes of this invention, numerous expression vector systems can be employed. These expression vectors are typically replicable in the host organisms either as episomes or as an integral part of the host chromosomal DNA. Expression vectors can include expression control sequences including, but not limited to, promoters (e.g., naturally-associated or heterologous promoters), enhancers, signal sequences, splice signals, enhancer elements, and transcription termination sequences. Preferably, the expression control sequences are eukaryotic promoter systems in vectors capable of transforming or transfecting eukaryotic host cells. Expression vectors can also utilize DNA elements which are derived from animal viruses such as bovine papilloma virus, polyoma virus, adenovirus, vaccinia virus, baculovirus, retroviruses (RSV, MMTV or MOMLV), cytomegalovirus (CMV), or SV40 virus. Others involve the use of polycistronic systems with internal ribosome binding sites.

Commonly, expression vectors contain selection markers (e.g., ampicillin-resistance, hygromycin-resistance, tetracycline resistance or neomycin resistance) to permit detection of those cells transformed with the desired DNA sequences (see, e.g., Itakura et al., U.S. Pat. No. 4,704,362). Cells which have integrated the DNA into their chromosomes can be selected by introducing one or more markers which allow selection of transfected host cells. The marker can provide for prototrophy to an auxotrophic host, biocide resistance (e.g., antibiotics) or resistance to heavy metals such as copper. The selectable marker gene can either be directly linked to the DNA sequences to be expressed, or introduced into the same cell by cotransformation.

An example of a vector useful for expressing an optimized FIX sequence is NEOSPLA (U.S. Pat. No. 6,159,730). This vector contains the cytomegalovirus promoter/enhancer, the mouse beta globin major promoter, the SV40 origin of replication, the bovine growth hormone polyadenylation sequence, neomycin phosphotransferase exon 1 and exon 2, the dihydrofolate reductase gene and leader sequence. This vector has been found to result in very high level expression of antibodies upon incorporation of variable and constant region genes, transfection in cells, followed by selection in G418 containing medium and methotrexate amplification. Vector systems are also taught in U.S. Pat. Nos. 5,736,137 and 5,658,570, each of which is incorporated by reference in its entirety herein. This system provides for high expression levels, e.g., >30 pg/cell/day. Other exemplary vector systems are disclosed e.g., in U.S. Pat. No. 6,413,777.

In other embodiments the polypeptides of the instant invention can be expressed using polycistronic constructs. In these expression systems, multiple gene products of interest such as multiple polypeptides of multimer binding protein can be produced from a single polycistronic construct. These systems advantageously use an internal ribosome entry site (IRES) to provide relatively high levels of polypeptides in eukaryotic host cells. Compatible IRES sequences are disclosed in U.S. Pat. No. 6,193,980 which is also incorporated herein.

More generally, once the vector or DNA sequence encoding a polypeptide has been prepared, the expression vector can be introduced into an appropriate host cell. That is, the host cells can be transformed. Introduction of the plasmid into the host cell can be accomplished by various techniques well known to those of skill in the art, as discussed above. The transformed cells are grown under conditions appropriate to the production of the FIX polypeptide, and assayed for FIX polypeptide synthesis. Exemplary assay techniques include enzyme-linked immunosorbent assay (ELISA), radioimmunoassay (RIA), or flourescence-activated cell sorter analysis (FACS), immunohistochemistry and the like.

In descriptions of processes for isolation of polypeptides from recombinant hosts, the terms "cell" and "cell culture" are used interchangeably to denote the source of polypeptide unless it is clearly specified otherwise. In other words, recovery of polypeptide from the "cells" can mean either from spun down whole cells, or from the cell culture containing both the medium and the suspended cells.

The host cell line used for protein expression is preferably of mammalian origin; most preferably of human or mouse origin, as the isolated nucleic acids of the invention have been optimized for expression in human cells. Exemplary host cell lines have been described above. In one embodiment of the method to produce a polypeptide with FIX activity, the host cell is a HEK293 cell. In another embodiment of the method to produce a polypeptide with FIX activity, the host cell is a CHO cell.

Genes encoding the polypeptides of the invention can also be expressed in non-mammalian cells such as bacteria or yeast or plant cells. In this regard it will be appreciated that various unicellular non-mammalian microorganisms such as bacteria can also be transformed; i.e., those capable of being grown in cultures or fermentation. Bacteria, which are susceptible to transformation, include members of the enterobacteriaceae, such as strains of *Escherichia coli* or *Salmonella*; Bacillaceae, such as *Bacillus subtilis*; *Pneumococcus*; *Streptococcus*, and *Haemophilus influenzae*. It will further be appreciated that, when expressed in bacteria, the polypeptides typically become part of inclusion bodies. The polypeptides must be isolated, purified and then assembled into functional molecules.

Alternatively, optimized nucleotide sequences of the invention can be incorporated in transgenes for introduction into the genome of a transgenic animal and subsequent expression in the milk of the transgenic animal (see, e.g., Deboer et al., U.S. Pat. No. 5,741,957, Rosen, U.S. Pat. No. 5,304,489, and Meade et al., U.S. Pat. No. 5,849,992). Suitable transgenes include coding sequences for polypeptides in operable linkage with a promoter and enhancer from a mammary gland specific gene, such as casein or beta lactoglobulin.

In vitro production allows scale-up to give large amounts of the desired polypeptides. Techniques for mammalian cell cultivation under tissue culture conditions are known in the art and include homogeneous suspension culture, e.g. in an airlift reactor or in a continuous stirrer reactor, or immobilized or entrapped cell culture, e.g. in hollow fibers, microcapsules, on agarose microbeads or ceramic cartridges. If necessary and/or desired, the solutions of polypeptides can be purified by the customary chromatography methods, for example gel filtration, ion-exchange chromatography, chromatography over DEAE-cellulose or (immuno-)affinity chromatography, e.g., after preferential biosynthesis of a synthetic hinge region polypeptide or prior to or subsequent to the HIC chromatography step described herein. An affinity tag sequence (e.g. a His(6) tag) can optionally be attached or included within the polypeptide sequence to facilitate downstream purification.

Once expressed, the FIX protein can be purified according to standard procedures of the art, including ammonium sulfate precipitation, affinity column chromatography, HPLC purification, gel electrophoresis and the like (see generally Scopes, Protein Purification (Springer-Verlag, N.Y., (1982)). Substantially pure proteins of at least about 90 to 95% homogeneity are preferred, and 98 to 99% or more homogeneity most preferred, for pharmaceutical uses.

Pharmaceutical Composition

Compositions containing the FIX protein of the present invention or the isolated nucleic acids of the present invention can contain a suitable pharmaceutically acceptable carrier. For example, they can contain excipients and/or auxiliaries that facilitate processing of the active compounds into preparations designed for delivery to the site of action.

The pharmaceutical composition can be formulated for parenteral administration (i.e. intravenous, subcutaneous, or intramuscular) by bolus injection. Formulations for injection can be presented in unit dosage form, e.g., in ampoules or in multidose containers with an added preservative. The compositions can take such forms as suspensions, solutions, or emulsions in oily or aqueous vehicles, and contain formulatory agents such as suspending, stabilizing and/or dispersing agents. Alternatively, the active ingredient can be in powder form for constitution with a suitable vehicle, e.g., pyrogen free water.

Suitable formulations for parenteral administration also include aqueous solutions of the active compounds in water-soluble form, for example, water-soluble salts. In addition, suspensions of the active compounds as appropriate oily injection suspensions can be administered. Suitable lipophilic solvents or vehicles include fatty oils, for example, sesame oil, or synthetic fatty acid esters, for example, ethyl oleate or triglycerides. Aqueous injection suspensions can contain substances, which increase the viscosity of the suspension, including, for example, sodium carboxymethyl cellulose, sorbitol and dextran. Optionally, the suspension can also contain stabilizers. Liposomes also can be used to encapsulate the molecules of the invention for delivery into cells or interstitial spaces. Exemplary pharmaceutically acceptable carriers are physiologically compatible solvents, dispersion media, coatings, antibacterial and antifungal agents, isotonic and absorption delaying agents, water, saline, phosphate buffered saline, dextrose, glycerol, ethanol and the like. In some embodiments, the composition comprises isotonic agents, for example, sugars, polyalcohols such as mannitol, sorbitol, or sodium chloride. In other embodiments, the compositions comprise pharmaceutically acceptable substances such as wetting agents or minor amounts of auxiliary substances such as wetting or emulsifying agents, preservatives or buffers, which enhance the shelf life or effectiveness of the active ingredients.

Compositions of the invention can be in a variety of forms, including, for example, liquid (e.g., injectable and infusible solutions), dispersions, suspensions, semi-solid and solid dosage forms. The preferred form depends on the mode of administration and therapeutic application.

The composition can be formulated as a solution, micro emulsion, dispersion, liposome, or other ordered structure suitable to high drug concentration. Sterile injectable solutions can be prepared by incorporating the active ingredient in the required amount in an appropriate solvent with one or a combination of ingredients enumerated above, as required, followed by filtered sterilization. Generally, dispersions are prepared by incorporating the active ingredient into a sterile vehicle that contains a basic dispersion medium and the required other ingredients from those enumerated above. In the case of sterile powders for the preparation of sterile injectable solutions, the preferred methods of preparation are vacuum drying and freeze-drying that yields a powder of the active ingredient plus any additional desired ingredient from a previously sterile-filtered solution. The proper fluidity of a solution can be maintained, for example, by the use of a coating such as lecithin, by the maintenance of the required particle size in the case of dispersion and by the use of surfactants. Prolonged absorption of injectable compositions can be brought about by including in the composition an agent that delays absorption, for example, monostearate salts and gelatin.

The active ingredient can be formulated with a controlled-release formulation or device. Examples of such formulations and devices include implants, transdermal patches, and microencapsulated delivery systems. Biodegradable, biocompatible polymers can be used, for example, ethylene vinyl acetate, polyanhydrides, polyglycolic acid, collagen, polyorthoesters, and polylactic acid. Methods for the preparation of such formulations and devices are known in the art. See, e.g., Sustained and Controlled Release Drug Delivery Systems, J. R. Robinson, ed., Marcel Dekker, Inc., New York, 1978.

Injectable depot formulations can be made by forming microencapsulated matrices of the drug in biodegradable polymers such as polylactide-polyglycolide. Depending on the ratio of drug to polymer, and the nature of the polymer employed, the rate of drug release can be controlled. Other exemplary biodegradable polymers are polyorthoesters and polyanhydrides. Depot injectable formulations also can be prepared by entrapping the drug in liposomes or microemulsions.

Supplementary active compounds can be incorporated into the compositions. In one embodiment, the chimeric protein of the invention is formulated with another clotting factor, or a variant, fragment, analogue, or derivative thereof. For example, the clotting factor includes, but is not limited to, factor V, factor VII, factor VIII, factor X, factor XI, factor XII, factor XIII, prothrombin, fibrinogen, von Willebrand factor or recombinant soluble tissue factor (rsTF) or activated forms of any of the preceding. The clotting factor of hemostatic agent can also include anti-fibrinolytic drugs, e.g., epsilon-amino-caproic acid, tranexamic acid.

Dosage regimens can be adjusted to provide the optimum desired response. For example, a single bolus can be administered, several divided doses can be administered over time, or the dose can be proportionally reduced or increased as indicated by the exigencies of the therapeutic situation. It is advantageous to formulate parenteral compositions in dosage unit form for ease of administration and uniformity of dosage. See, e.g., Remington's Pharmaceutical Sciences (Mack Pub. Co., Easton, Pa. 1980).

In addition to the active compound, the liquid dosage form can contain inert ingredients such as water, ethyl alcohol, ethyl carbonate, ethyl acetate, benzyl alcohol, benzyl benzoate, propylene glycol, 1,3-butylene glycol, dimethylformamide, oils, glycerol, tetrahydrofurfuryl alcohol, polyethylene glycols, and fatty acid esters of sorbitan.

Non-limiting examples of suitable pharmaceutical carriers are also described in Remington's Pharmaceutical Sciences by E. W. Martin. Some examples of excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol, and the like. The composition can also contain pH buffering reagents, and wetting or emulsifying agents.

For oral administration, the pharmaceutical composition can take the form of tablets or capsules prepared by conventional means. The composition can also be prepared as a liquid for example a syrup or a suspension. The liquid can include suspending agents (e.g., sorbitol syrup, cellulose derivatives or hydrogenated edible fats), emulsifying agents (lecithin or acacia), non-aqueous vehicles (e.g., almond oil, oily esters, ethyl alcohol, or fractionated vegetable oils), and preservatives (e.g., methyl or propyl-p-hydroxybenzoates or sorbic acid). The preparations can also include flavoring, coloring and sweetening agents. Alternatively, the composition can be presented as a dry product for constitution with water or another suitable vehicle.

For buccal administration, the composition can take the form of tablets or lozenges according to conventional protocols.

For administration by inhalation, the compounds for use according to the present invention are conveniently delivered in the form of a nebulized aerosol with or without excipients or in the form of an aerosol spray from a pressurized pack or nebulizer, with optionally a propellant, e.g., dichlorodifluoromethane, trichlorofluoromethane, dichlorotetrafluoromethane, carbon dioxide or other suitable gas. In the case of a pressurized aerosol the dosage unit can be determined by providing a valve to deliver a metered amount. Capsules and cartridges of, e.g., gelatin for use in an inhaler or insufflator can be formulated containing a powder mix of the compound and a suitable powder base such as lactose or starch.

The pharmaceutical composition can also be formulated for rectal administration as a suppository or retention enema, e.g., containing conventional suppository bases such as cocoa butter or other glycerides.

In one embodiment, a pharmaceutical composition comprises a FIX protein, the optimized polynucleotide encoding the FIX protein, the vector comprising the polynucleotide, or the host cell comprising the vector, and a pharmaceutically acceptable carrier. In some embodiments, the composition is administered by a route selected from the group consisting of topical administration, intraocular administration, parenteral administration, intrathecal administration, subdural administration and oral administration. The parenteral administration can be intravenous or subcutaneous administration.

In other embodiments, the composition is used to treat a bleeding disease or condition in a subject in need thereof. The bleeding disease or condition is selected from the group consisting of a bleeding coagulation disorder, hemarthrosis, muscle bleed, oral bleed, hemorrhage, hemorrhage into muscles, oral hemorrhage, trauma, trauma capitis, gastrointestinal bleeding, intracranial hemorrhage, intra-abdominal hemorrhage, intrathoracic hemorrhage, bone fracture, central nervous system bleeding, bleeding in the retropharyngeal space, bleeding in the retroperitoneal space, bleeding in the illiopsoas sheath and any combinations thereof. In still other embodiments, the subject is scheduled to undergo a surgery. In yet other embodiments, the treatment is prophylactic or on-demand.

Methods of Treatment

The invention provides a method of treating a bleeding disorder comprising administering to a subject in need thereof a nucleic acid molecule, vector, or polypeptide of the invention. In some embodiments, the bleeding disorder is characterized by a deficiency in Factor IX. In some embodiments, the bleeding disorder is hemophilia. In some embodiments, the bleeding disorder is hemophilia B. In some embodiments of the method of treating a bleeding disorder, plasma Factor IX activity at 24 hours post administration is increased relative to a subject administered a reference nucleic acid molecule comprising SEQ ID NO: 2, a vector comprising the reference nucleic acid molecule, or a polypeptide encoded by the reference nucleic acid molecule.

The invention also relates to a method of treating, ameliorating, or preventing a hemostatic disorder in a subject comprising administering a therapeutically effective amount of an FIX protein of the invention or an isolated nucleic acid molecule of the invention. The treatment, amelioration, and prevention by the FIX protein or isolated nucleic acid molecule can be a bypass therapy. The subject receiving bypass therapy can have already developed an inhibitor to a clotting factor, e.g., Factor IX, or is subject to developing a clotting factor inhibitor.

The nucleic acid molecules, vectors, or FIX polypeptides of the invention treat or prevent a hemostatic disorder by promoting the formation of a fibrin clot. The FIX protein of the invention can activate a member of a coagulation cascade. The clotting factor can be a participant in the extrinsic pathway, the intrinsic pathway or both.

The nucleic acid molecules, vectors, or FIX polypeptides of the invention can be used to treat hemostatic disorders known to be treatable with FIX. The hemostatic disorders that can be treated using methods of the invention include, but are not limited to, hemophilia A, hemophilia B, von Willebrand's disease, Factor XI deficiency (PTA deficiency), Factor XII deficiency, as well as deficiencies or structural abnormalities in fibrinogen, prothrombin, Factor V, Factor VII, Factor X, or Factor XIII, hemarthrosis, muscle bleed, oral bleed, hemorrhage, hemorrhage into muscles, oral hemorrhage, trauma, trauma capitis, gastrointestinal bleeding, intracranial hemorrhage, intra-abdominal hemorrhage, intrathoracic hemorrhage, bone fracture, central nervous system bleeding, bleeding in the retropharyngeal space, bleeding in the retroperitoneal space, and bleeding in the illiopsoas sheath. Compositions for administration to a subject include nucleic acid molecules which comprise an optimized nucleotide sequence of the invention encoding a FIX clotting factor (for gene therapy applications) as well as FIX polypeptide molecules.

In some embodiments, the hemostatic disorder is an inherited disorder. In one embodiment, the subject has hemophilia B. In other embodiments, the hemostatic disorder is the result of a deficiency in Factor IX. In other embodiments, the hemostatic disorder can be the result of a defective FIX clotting factor.

In another embodiment, the hemostatic disorder can be an acquired disorder. The acquired disorder can result from an underlying secondary disease or condition. The unrelated condition can be, as an example, but not as a limitation, cancer, an autoimmune disease, or pregnancy. The acquired disorder can result from old age or from medication to treat an underlying secondary disorder (e.g. cancer chemotherapy).

The invention also relates to methods of treating a subject that does not have a hemostatic disorder or a secondary disease or condition resulting in acquisition of a hemostatic disorder. The invention thus relates to a method of treating a subject in need of a general hemostatic agent comprising administering a therapeutically effective amount of the FIX polypeptide of the invention or an isolated nucleic acid molecule of the invention. For example, in one embodiment, the subject in need of a general hemostatic agent is undergoing, or is about to undergo, surgery. The FIX polypeptide of the invention or an isolated nucleic acid molecule of the invention can be administered prior to or after surgery as a prophylactic. The FIX polypeptide of the invention or an isolated nucleic acid molecule of the invention can be administered during or after surgery to control an acute bleeding episode. The surgery can include, but is not limited to, liver transplantation, liver resection, or stem cell transplantation.

In another embodiment, the FIX polypeptide of the invention or an isolated nucleic acid molecule of the invention can be used to treat a subject having an acute bleeding episode who does not have a hemostatic disorder. The acute bleeding episode can result from severe trauma, e.g., surgery, an automobile accident, wound, laceration gun shot, or any other traumatic event resulting in uncontrolled bleeding.

The FIX protein or the isolated nucleic acid molecules of the invention can be used to prophylactically treat a subject with a hemostatic disorder. The FIX protein or the isolated nucleic acid molecules of the invention can be used to treat an acute bleeding episode in a subject with a hemostatic disorder.

In some embodiments, a FIX protein composition or an isolated nucleic acid molecules of the invention is administered in combination with at least one other agent that promotes hemostasis. Said other agent that promotes hemostasis in a therapeutic with demonstrated clotting activity. As an example, but not as a limitation, the hemostatic agent can include Factor V, Factor VII, Factor VIII, Factor X, Factor XI, Factor XII, Factor XIII, prothrombin, or fibrinogen or activated forms of any of the preceding. The clotting factor or hemostatic agent can also include anti-fibrinolytic drugs, e.g., epsilon-amino-caproic acid, tranexamic acid.

In one embodiment of the invention, the composition (e.g., the FIX polypeptide or the optimized nucleic acid molecule encoding the FIX polypeptide) is one in which the FIX is present in activatable form when administered to a subject. Such an activatable molecule can be activated in vivo at the site of clotting after administration to a subject.

The FIX polypeptide or the optimized nucleic acid molecule encoding the FIX polypeptide can be administered intravenously, subcutaneously, intramuscularly, or via any mucosal surface, e.g., orally, sublingually, buccally, sublingually, nasally, rectally, vaginally or via pulmonary route. The FIX protein can be implanted within or linked to a biopolymer solid support that allows for the slow release of the chimeric protein to the desired site.

For oral administration, the pharmaceutical composition can take the form of tablets or capsules prepared by conventional means. The composition can also be prepared as a liquid for example a syrup or a suspension. The liquid can include suspending agents (e.g., sorbitol syrup, cellulose derivatives or hydrogenated edible fats), emulsifying agents (lecithin or acacia), non-aqueous vehicles (e.g., almond oil, oily esters, ethyl alcohol, or fractionated vegetable oils), and preservatives (e.g., methyl or propyl-p-hydroxybenzoates or sorbic acid). The preparations can also include flavoring, coloring and sweetening agents. Alternatively, the composition can be presented as a dry product for constitution with water or another suitable vehicle.

For buccal and sublingual administration the composition can take the form of tablets, lozenges or fast dissolving films according to conventional protocols.

For administration by inhalation, the polypeptide having FIX activity for use according to the present invention are conveniently delivered in the form of an aerosol spray from a pressurized pack or nebulizer (e.g. in PBS), with a suitable propellant, e.g., dichlorodifluoromethane, trichlorofluoromethane, dichlorotetrafluoromethane, carbon dioxide or other suitable gas. In the case of a pressurized aerosol the dosage unit can be determined by providing a valve to deliver a metered amount. Capsules and cartridges of, e.g., gelatin for use in an inhaler or insufflator can be formulated containing a powder mix of the compound and a suitable powder base such as lactose or starch.

In one embodiment, the route of administration of the FIX polypeptide or the optimized nucleic acid molecule encoding the FIX polypeptide is parenteral. The term parenteral as used herein includes intravenous, intraarterial, intraperitoneal, intramuscular, subcutaneous, rectal or vaginal administration. The intravenous form of parenteral administration is preferred. In some embodiments, the route of administration of the FIX polypeptide or the optimized nucleic acid molecule encoding the FIX polypeptide is subcutaneous. While all these forms of administration are clearly contemplated as being within the scope of the invention, a form for administration would be a solution for injection, in particular for intravenous or intraarterial injection or drip. Usually, a suitable pharmaceutical composition for injection can comprise a buffer (e.g. acetate, phosphate or citrate buffer), a surfactant (e.g. polysorbate), optionally a stabilizer agent (e.g. human albumin), etc. However, in other methods compatible with the teachings herein, the FIX polypeptides or the optimized nucleic acid molecules encoding the FIX polypeptides can be delivered directly to the site of the adverse cellular population thereby increasing the exposure of the diseased tissue to the therapeutic agent.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. In the subject invention, pharmaceutically acceptable carriers include, but are not limited to, 0.01-0.1M and preferably 0.05M phosphate buffer or 0.8% saline. Other common parenteral vehicles include sodium phosphate solutions, Ringer's dextrose, dextrose and sodium chloride, lactated Ringer's, or fixed oils. Intravenous vehicles include fluid and nutrient replenishers, electrolyte replenishers, such as those based on Ringer's dextrose, and the like. Preservatives and other additives can also be present such as for example, antimicrobials, antioxidants, chelating agents, and inert gases and the like.

More particularly, pharmaceutical compositions suitable for injectable use include sterile aqueous solutions (where water soluble) or dispersions and sterile powders for the extemporaneous preparation of sterile injectable solutions or dispersions. In such cases, the composition must be sterile and should be fluid to the extent that easy syringability exists. It should be stable under the conditions of manufacture and storage and will preferably be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants.

Prevention of the action of microorganisms can be achieved by various antibacterial and antifungal agents, for example, parabens, chlorobutanol, phenol, ascorbic acid, thimerosal and the like. In many cases, it will be preferable to include isotonic agents, for example, sugars, polyalcohols, such as mannitol, sorbitol, or sodium chloride in the composition. Prolonged absorption of the injectable compositions can be brought about by including in the composition an agent which delays absorption, for example, aluminum monostearate and gelatin.

In any case, sterile injectable solutions can be prepared by incorporating an active compound (e.g., a polypeptide by itself or in combination with other active agents) in the required amount in an appropriate solvent with one or a combination of ingredients enumerated herein, as required, followed by filtered sterilization. Generally, dispersions are prepared by incorporating the active compound into a sterile vehicle, which contains a basic dispersion medium and the required other ingredients from those enumerated above. In the case of sterile powders for the preparation of sterile injectable solutions, the preferred methods of preparation are vacuum drying and freeze-drying, which yields a powder of an active ingredient plus any additional desired ingredient from a previously sterile-filtered solution thereof. The preparations for injections are processed, filled into containers such as ampoules, bags, bottles, syringes or vials, and sealed under aseptic conditions according to methods known in the art. Further, the preparations can be packaged and sold in the form of a kit. Such articles of manufacture will preferably have labels or package inserts indicating that the associated compositions are useful for treating a subject suffering from, or predisposed to clotting disorders.

The pharmaceutical composition can also be formulated for rectal administration as a suppository or retention enema, e.g., containing conventional suppository bases such as cocoa butter or other glycerides.

Effective doses of the compositions of the present invention, for the treatment of conditions vary depending upon many different factors, including means of administration, target site, physiological state of the patient, whether the patient is human or an animal, other medications administered, and whether treatment is prophylactic or therapeutic. Usually, the patient is a human but non-human mammals including transgenic mammals can also be treated. Treatment dosages can be titrated using routine methods known to those of skill in the art to optimize safety and efficacy.

Dosages can range from 1000 µg/kg to 0.1 ng/kg body weight. In one embodiment, the dosing range is 1 µg/kg to 100 µg/kg. The FIX polypeptide or the optimized nucleic acid molecule encoding the FIX polypeptide can be administered continuously or at specific timed intervals. In vitro assays can be employed to determine optimal dose ranges and/or schedules for administration. In vitro assays that measure clotting factor activity are known in the art. Additionally, effective doses can be extrapolated from dose-response curves obtained from animal models, e.g., a hemophiliac dog (Mount et al. 2002, Blood 99 (8): 2670).

Doses intermediate in the above ranges are also intended to be within the scope of the invention. Subjects can be administered such doses daily, on alternative days, weekly or according to any other schedule determined by empirical analysis. An exemplary treatment entails administration in multiple dosages over a prolonged period, for example, of at least six months. In some methods, two or more polypeptides can be administered simultaneously, in which case the dosage of each polypeptide administered falls within the ranges indicated.

FIX polypeptides or the optimized nucleic acid molecules encoding the FIX polypeptides of the invention can be administered on multiple occasions. Intervals between single dosages can be daily, weekly, monthly or yearly. Intervals can also be irregular as indicated by measuring blood levels of modified polypeptide or antigen in the patient. Alternatively, polypeptides can be administered as a sustained release formulation, in which case less frequent administration is required. Dosage and frequency vary depending on the half-life of the polypeptide or polynucleotide in the patient.

The dosage and frequency of administration can vary depending on whether the treatment is prophylactic or therapeutic. In prophylactic applications, compositions containing the FIX polypeptide or the optimized nucleic acid molecule encoding the FIX polypeptide or a cocktail thereof are administered to a patient not already in the disease state to enhance the patient's resistance or minimize effects of disease. Such an amount is defined to be a "prophylactic effective dose." A relatively low dosage is administered at relatively infrequent intervals over a long period of time. Some patients continue to receive treatment for the rest of their lives.

FIX polypeptides or the optimized nucleic acid molecules encoding the FIX polypeptides of the invention can optionally be administered in combination with other agents that are effective in treating the disorder or condition in need of treatment (e.g., prophylactic or therapeutic).

As used herein, the administration of FIX polypeptides or the optimized nucleic acid molecules encoding the FIX polypeptides of the invention in conjunction or combination with an adjunct therapy means the sequential, simultaneous, coextensive, concurrent, concomitant or contemporaneous administration or application of the therapy and the disclosed polypeptides. Those skilled in the art will appreciate that the administration or application of the various components of the combined therapeutic regimen can be timed to enhance the overall effectiveness of the treatment. A skilled artisan (e.g. a physician) would be readily able to discern effective combined therapeutic regimens without undue experimentation based on the selected adjunct therapy and the teachings of the instant specification.

It will further be appreciated that the FIX polypeptide or the optimized nucleic acid molecule encoding the FIX polypeptide of the instant invention can be used in conjunction or combination with an agent or agents (e.g. to provide a combined therapeutic regimen). Exemplary agents with which a polypeptide or polynucleotide of the invention can be combined include agents that represent the current standard of care for a particular disorder being treated. Such agents can be chemical or biologic in nature. The term "biologic" or "biologic agent" refers to any pharmaceutically active agent made from living organisms and/or their products which is intended for use as a therapeutic.

The amount of agent to be used in combination with the polynucleotides or polypeptides of the instant invention can vary by subject or can be administered according to what is known in the art. See for example, Bruce A Chabner et al., *Antineoplastic Agents*, in GOODMAN & GILMAN'S THE PHARMACOLOGICAL BASIS OF THERAPEUTICS 1233-1287 (Joel G. Hardman et al., eds., 9$^{th}$ ed. 1996). In another embodiment, an amount of such an agent consistent with the standard of care is administered.

As previously discussed, the polynucleotides and polypeptides of the present invention, can be administered in a pharmaceutically effective amount for the in vivo treatment of clotting disorders. In this regard, it will be appreciated that the polypeptides or polynucleotides of the invention can be formulated to facilitate administration and promote stability of the active agent. Preferably, pharmaceutical compositions in accordance with the present invention comprise a pharmaceutically acceptable, non-toxic, sterile carrier such as physiological saline, non-toxic buffers, preservatives and the like. Of course, the pharmaceutical compositions of the present invention can be administered in single or multiple doses to provide for a pharmaceutically effective amount of the polypeptide.

A number of tests are available to assess the function of the coagulation system: activated partial thromboplastin time (aPTT) test, chromogenic assay, ROTEM® assay, prothrombin time (PT) test (also used to determine INR), fibrinogen testing (often by the Clauss method), platelet count, platelet function testing (often by PFA-100), TCT, bleeding time, mixing test (whether an abnormality corrects if the patient's plasma is mixed with normal plasma), coagulation factor assays, antiphosholipid antibodies, D-dimer, genetic tests (e.g., factor V Leiden, prothrombin mutation G20210A), dilute Russell's viper venom time (dRVVT), miscellaneous platelet function tests, thromboelastography (TEG or Sonoclot), thromboelastometry (TEM®, e.g, ROTEM®, or euglobulin lysis time (ELT).

The aPTT test is a performance indicator measuring the efficacy of both the "intrinsic" (also referred to the contact activation pathway) and the common coagulation pathways. This test is commonly used to measure clotting activity of commercially available recombinant clotting factors, e.g., FVIII or FIX. It is used in conjunction with prothrombin time (PT), which measures the extrinsic pathway.

ROTEM® analysis provides information on the whole kinetics of haemostasis: clotting time, clot formation, clot stability and lysis. The different parameters in thromboelastometry are dependent on the activity of the plasmatic coagulation system, platelet function, fibrinolysis, or many factors which influence these interactions. This assay can provide a complete view of secondary haemostasis.

Gene Therapy

The invention provides a method of increasing expression of a polypeptide with Factor IX activity in a subject comprising administering the isolated nucleic acid molecule of the invention to a subject in need thereof, wherein the expression of the polypeptide is increased relative to a reference nucleic acid molecule comprising SEQ ID NO: 2. The invention also provides a method of increasing expression of a polypeptide with Factor IX activity in a subject comprising administering a vector of the invention to a subject in need thereof, wherein the expression of the polypeptide is increased relative to a vector comprising a reference nucleic acid molecule.

Somatic gene therapy has been explored as a possible treatment for hemophilia A. Gene therapy is a particularly appealing treatment for hemophilia because of its potential to cure the disease through continuous endogenous production of FIX following a single administration of vector. Haemophilia B is well suited for a gene replacement approach because its clinical manifestations are entirely attributable to the lack of a single gene product (FIX) that circulates in minute amounts (200 ng/ml) in the plasma.

A FIX protein of the invention can be produced in vivo in a mammal, e.g., a human patient, using a gene therapy approach to treatment of a bleeding disease or disorder selected from the group consisting of a bleeding coagulation disorder, hemarthrosis, muscle bleed, oral bleed, hemorrhage, hemorrhage into muscles, oral hemorrhage, trauma, trauma capitis, gastrointestinal bleeding, intracranial hemorrhage, intra-abdominal hemorrhage, intrathoracic hemorrhage, bone fracture, central nervous system bleeding, bleeding in the retropharyngeal space, bleeding in the retroperitoneal space, and bleeding in the illiopsoas sheath would be therapeutically beneficial. In one embodiment, the bleeding disease or disorder is hemophilia. In another embodiment, the bleeding disease or disorder is hemophilia B. This involves administration of an optimized FIX encoding nucleic acid operably linked to suitable expression control sequences. In certain embodiment, these sequences are incorporated into a viral vector. Suitable viral vectors for such gene therapy include adenoviral vectors, lentiviral vectors, baculoviral vectors, Epstein Barr viral vectors, papovaviral vectors, vaccinia viral vectors, herpes simplex viral vectors, and adeno associated virus (AAV) vectors. The viral vector can be a replication-defective viral vector. In other embodiments, an adenoviral vector has a deletion in its E1 gene or E3 gene. When an adenoviral vector is used, the mammal can not be exposed to a nucleic acid encoding a selectable marker gene. In other embodiments, the sequences are incorporated into a non-viral vector known to those skilled in the art.

All of the various aspects, embodiments, and options described herein can be combined in any and all variations.

All publications, patents, and patent applications mentioned in this specification are herein incorporated by reference to the same extent as if each individual publication, patent, or patent application was specifically and individually indicated to be incorporated by reference.

Having generally described this invention, a further understanding can be obtained by reference to the examples provided herein. These examples are for purposes of illustration only and are not intended to be limiting.

The application claims benefit to U.S. Provisional Application No. 62/019,069, filed Jun. 30, 2014, and U.S. Provisional Application No. 62/168,565, filed May 29, 2015, which are incorporated herein by reference in their entireties.

EXAMPLES

Example 1: Codon Optimization by GENSCRIPT OPTIMUMGENE™

The factor IX nucleotide sequence was codon optimized using GENSCRIPT OPTIMUMGENE™ codon optimization technology. (GenScript Corp., New Jersey, USA). The GENSCRIPT OPTIMUMGENE™ codon optimization technology is described in Burgess-Brown et al., Protein Expr Purif. 59(1):94-102 (2008).

The following human codon usage data was used for optimization:

| CODON | AMINO ACID | FRACTION | FREQUENCY/THOUSAND |
|---|---|---|---|
| TTT | F | 0.45 | 16.9 |
| TCT | S | 0.18 | 14.6 |
| TAT | Y | 0.43 | 12.0 |
| TGT | C | 0.45 | 9.9 |
| TTC | F | 0.55 | 20.4 |
| TCC | S | 0.22 | 17.4 |
| TAC | Y | 0.57 | 15.6 |
| TGC | C | 0.55 | 12.2 |
| TTA | L | 0.07 | 7.2 |
| TCA | S | 0.15 | 11.7 |
| TAA | * | 0.28 | 0.7 |
| TGA | * | 0.52 | 1.3 |
| TTG | L | 0.13 | 12.6 |
| TCG | S | 0.06 | 4.5 |
| TAG | * | 0.20 | 0.5 |
| TGG | W | 1.00 | 12.8 |
| CTT | L | 0.13 | 12.8 |
| CCT | P | 0.28 | 17.3 |
| CAT | H | 0.41 | 10.4 |
| CGT | R | 0.08 | 4.7 |
| CTC | L | 0.20 | 19.4 |
| CCC | P | 0.33 | 20.0 |
| CAC | H | 0.59 | 14.9 |
| CGC | R | 0.19 | 10.9 |
| CTA | L | 0.07 | 6.9 |
| CCA | P | 0.27 | 16.7 |
| CAA | Q | 0.25 | 11.8 |
| CGA | R | 0.11 | 6.3 |
| CTG | L | 0.41 | 40.3 |
| CCG | P | 0.11 | 7.0 |
| CAG | Q | 0.75 | 34.6 |
| CGG | R | 0.21 | 11.9 |
| ATT | I | 0.36 | 15.7 |
| ACT | T | 0.24 | 12.8 |
| AAT | N | 0.46 | 16.7 |
| AGT | S | 0.15 | 11.9 |
| ATC | I | 0.48 | 21.4 |
| ACC | T | 0.36 | 19.2 |
| AAC | N | 0.54 | 19.5 |
| AGC | S | 0.24 | 19.4 |
| ATA | I | 0.16 | 7.1 |
| ACA | T | 0.28 | 14.8 |
| AAA | K | 0.42 | 24.0 |
| AGA | R | 0.20 | 11.5 |
| ATG | M | 1.00 | 22.3 |
| ACG | T | 0.12 | 6.2 |
| AAG | K | 0.58 | 32.9 |
| AGG | R | 0.20 | 11.4 |
| GTT | V | 0.18 | 10.9 |
| GCT | A | 0.26 | 18.6 |
| GAT | D | 0.46 | 22.3 |
| GGT | G | 0.16 | 10.8 |
| GTC | V | 0.24 | 14.6 |
| GCC | A | 0.40 | 28.5 |
| GAC | D | 0.54 | 26.0 |
| GGC | G | 0.34 | 22.8 |
| GTA | V | 0.11 | 7.0 |
| GCA | A | 0.23 | 16.0 |
| GAA | E | 0.42 | 29.0 |
| GGA | G | 0.25 | 16.3 |
| GTG | V | 0.47 | 28.9 |
| GCG | A | 0.11 | 7.6 |
| GAG | E | 0.58 | 40.8 |
| GGG | G | 0.25 | 16.4 |

Codon usage was adjusted to human bias with the human codon adaptation index (CAI) changing from 0.72 (wild type human factor IX) to 0.87 (codon optimized factor IX). G/C content was increased from 41.17% to 51.37% and peaks of G/C content in a 60 bp window were removed. A destabilizing emement (ATTTA) and an antiviral motif (TGTGT) were eliminated. In addition, the optimized factor IX sequence was adjusted to avoid a number of sites, including mRNA secondary structure, cryptic splicing sites, premature PolyA sites, internal chi sites, ribosomal sites, CpG islands, RNA instability motif, repeat sequences (direct repeat, reverse repeat, and Dyad repeat), and restriction sites that may interfere with cloning. Table 2 shows the removal of cis-acting elements and antiviral motifs in human factor IX sequence.

TABLE 2

Removal of cis-acting elements and antiviral motifs in human factor IX sequence.

| CIS-Acting Elements or antiviral motifs | Original | Optimized |
|---|---|---|
| Splice(GGTAAG) | 0 | 0 |
| Splice(GGTGAT) | 0 | 0 |
| PolyA(AATAAA) | 0 | 0 |
| PolyA(ATTAAA) | 0 | 0 |
| Destabilizing(ATTTA) | 1 | 0 |
| PolyT(TTTTTT) | 0 | 0 |
| PolyA(AAAAAAA) | 0 | 0 |
| Antiviral Motifs | 1 | 0 |

Table 3 shows the removal of repeat sequences in human FIX nucleotide sequence.

TABLE 3

Removal of repeat sequences in human factor IX sequence.

Original

Max Direct Repeat: Size: 11 Distance: 379 Frequency: 2
Max Inverted Repeat: Size: 9 Tm: 20.4 Start Positions: 184, 726
Max Dyad Repeat: Size: 10 Tm: 24.0 Start Positions: 720, 1287

Optimized

Max Direct Repeat: Size: 9 Distance: 840 Frequency: 2
Max Inverted Repeat: Size: 9 Tm: 10.2 Start Positions: 950, 30
Max Dyad Repeat: Size: 11 Tm: 38.4 Start Positions: 164, 1267

The resulting sequence of optimized human factor IX gene is shown in FIG. 1.

Example 2: Expression Constructs

All constructs is made in the Invitrogen pcDNA™4 vector backbone, which contains a human cytomegalovirus immediate-early (CMV) promoter, a QBI SP163 translation enhancer, and a ZEOCIN™ resistance gene for selection. Standard molecular cloning techniques are employed and all the constructs are confirmed by DNA sequencing.

A base vector, pcDNA4-FIX that uses native codon and drives expression of wild-type factor IX, is constructed in pcDNA4 backbone (Invitrogen).

Additional constructs are produced by replacing the wild-type factor IX sequence with several FIX variants using BsiWI and XhoI sites. These FIX variants include: 1) pcDNA4-FIX-R338L that uses native codon and drives the expression of a R338L factor IX variant; 2) pcDNA4-FIXco-R338L that uses the codon optimized sequence and drives the expression of a R338L factor IX variant.

Example 3: Expression Analysis of Codon Optimization in HemB Mice

To ask whether the codon optimization result in increased factor IX protein expression, expression plasmid pcDNA-FIXco-R338L and the control pcDNA-FIX-R338L is introduced into HemB mice via hydrodynamic injection. Subsequently, FIX protein and activity are monitored in each injected mouse by FIX ELISA and activity assays.

Hydrodynamic injection is an efficient and safe non-viral method to deliver genes to the liver in small animals, such as mice and rats. The protein of interest is produced in the liver and can be detected within 24 hours post-injection.

HemB mice weighing 20-35 grams are injected via intravenous tail vein injection with either pcDNA-FIXco-R338L, or the control pcDNA-FIX-R338L. Injections are made up with 10 ug naked plasmid DNA free of endotoxin in 0.9% sterile saline solution, to a total volume of 2 ml. Injections are performed rapidly, taking no more than 4-7 seconds to inject the full 2 ml DNA solution. Mice are closely monitored for two hours after injection, or until normal activity resumed. At 24 hours post-injection, samples are collected via retro orbital blood collection; plasma is prepared and stored at −80° C. for further analysis.

A FIX ELISA assay is used to measure the factor IX protein level in plasma from dosed mice using a goat anti-human FIX IgG antibody (Enzyme Research Laboratories) for capture and a goat anti-human FIX-HRP conjugate as a detection antibody (Enzyme Research Laboratories).

A factor IX activity assay is used to monitor the factor IX activity level in plasma with the use of the MLA Electra 1600C (Medical Laboratory Automation/Instrument Laboratories). Briefly, plasma samples are mixed with equal volumes of human FIX-deficient plasma (Diagnostica Stago; catalog no. 00724) and cephalin-containing ellagic acid activator (activated partial thromboplastin time [aPTT]-soluble activator; Helena Laboratories; catalog no. 5389), and, after 4 minutes of incubation, 5 mM calcium chloride (25 mM stock; Instrumentation Laboratory; catalog no. 020006910) is added, and the time to clot is measured. Activity is calculated on the basis of a calibration curve of clotting times versus activity unit concentration (in IU/mL) of serial dilutions of a World Health Organization FIX standard.

Example 4: Codon Optimization and Plasmid Construction

A codon-optimized factor IX (FIX) generated by GEN-SCRIPT OPTIMUMGENE™ technology (i.e., SEQ ID ON: 1) is renamed here as FIX-R338L-co1. Five additional FIX variants were generated and named as FIX-R338-co2, FIX-R338-co3, FIX-R338-co4, FIX-R338-co5, and FIX-R338-co6 by controlling the codon usage bias, which was measured by the codon adaptation index (CAI) and the relative synonymous codon usage (RSCU). An online tool Eugene was used to facilitate this process as described in Gaspar et al., 2012, *Bioinformatics* 28:2683-84. EuGene: maximizing synthetic gene design for heterologous expression. As shown in Table 4 all these five variants were adjusted to CAI>95%, and RSCU>2.4 from the 72% and 0.853 of the wild type, respectively.

In addition to the overall increase of the CAI, the five variants were also designed into 3 classes as illustrated in FIG. 6: 1) High CAI at N-terminal half of the coding sequence (FIX-R338L-co2 and -co3); 2) High CAI at C-terminal half of the coding sequence (FIX-R338L-co5 and -co6), and 3) even distribution of high CAI (FIX-R338L-co4). We reason that, if higher CAI is translated to faster protein translation, then these 3 classes would represent different rate of protein synthesis from the start to finish. So FIX-R338L-co5 and -co6 would start relatively slower through the N-terminal half, and then accelerate to the end of translation, which would be preferred for protein folding, and post-translational modification during translation without slowing down the overall protein synthesis. The opposite is FIX-R338L-co2 and -co3.

To ensure the stability of the mRNA, All the FIX variants were adjusted to avoid a number of sites, including cryptic splicing sites, premature polyA sites, RNA instability motif (ARE), repeat sequences. Second, the codon usage was changed to human bias, and GC content was adjusted as well. Sequence of these variants were listed below.

Example 5: Codon Optimization and Plasmid Construction

Figure 7:
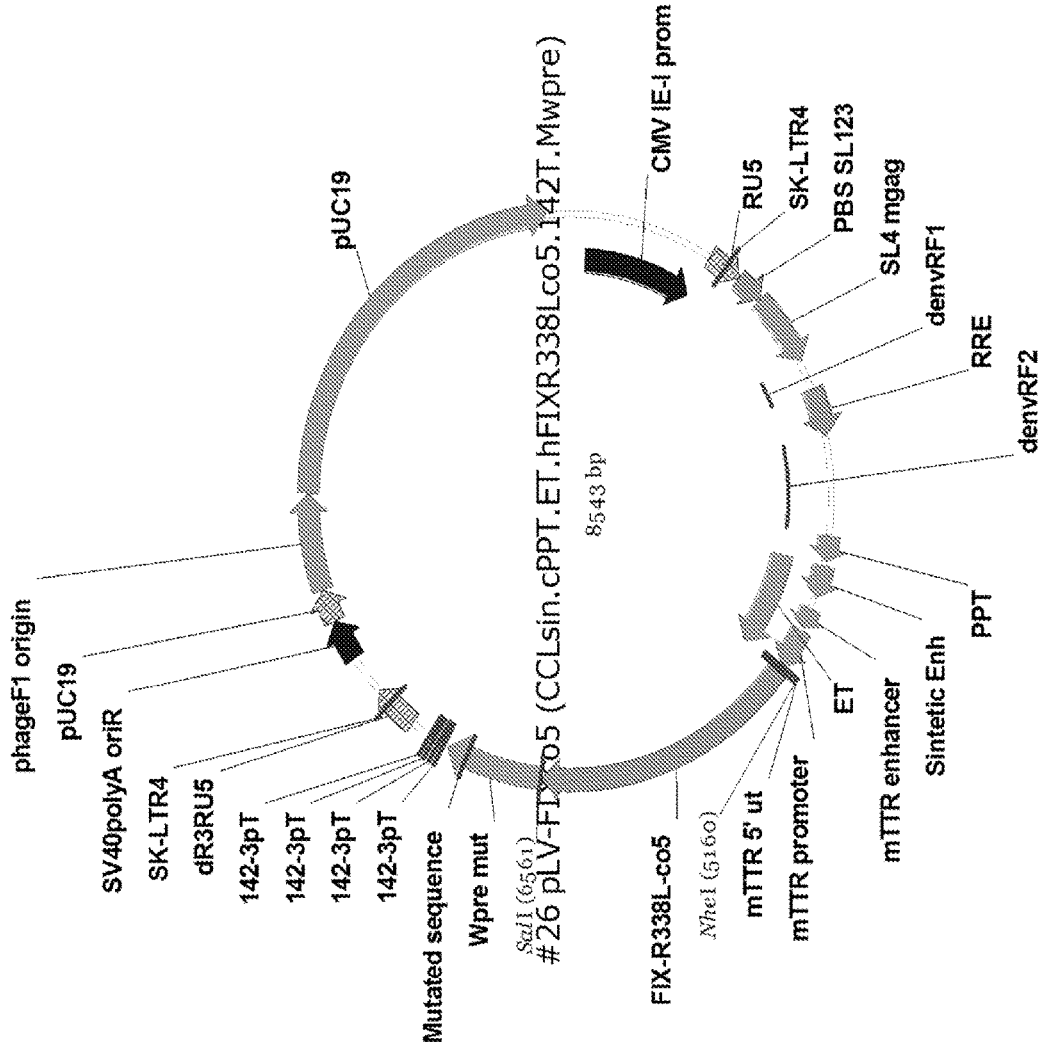
FIG. 7 exemplifies a lentiviral plasmid coding for a FIX variant. The plasmid shown (pLV-FIX-R338L-co5) codes for FIX-co5 and was produced by introducing the FIX-R338L-co5 variant sequence under the control of an ET promoter into a lentiviral vector using NheI and SalI restriction sites.

The FIX variants were cloned into lentiviral vector under the control of ET promoter using NheI and SalI sites, and resulting plasmids (Table 5, plasmids coding for FIX variants) was exemplified in FIG. 7. (pLV-FIX-R338L-co5).

TABLE 5

| Codon Optimized FIX Nucleotide Sequences | |
|---|---|
| Plasmid ID | SEQ ID no. |
| FIX-194 | Unmodified FIX under ET promoter in pcDNA |
| FIX-192 | codon optimized FIX-co1 under ET promoter in pcDNA |
| LV-FIX-R338L-co1 | codon optimized FIX-co1 with R338L under ET promoter in LV-expression system |
| LV-FIX-R338L-c2 | codon optimized FIX-co2 with R338L under ET promoter in LV-expression system |
| LV-FIX-R338L-co3 | codon optimized FIX-co3 with R338L under ET promoter in LV-expression system |
| LV-FIX-R338L-co4 | codon optimized FIX-co4 with R338L under ET promoter in LV-expression system |
| LV-FIX-R338L-co5 | codon optimized FIX-co4 with R338L under ET promoter in LV-expression system |

TABLE 4

| Codon Optimization Parameters of FIX variants | | | | | | | |
|---|---|---|---|---|---|---|---|
| | WT | FIX-R338L-co1 | FIX-R338L-co2 | FIX-R338L-co3 | FIX-R338L-co4 | FIX-R338L-co5 | FIX-R338L-co6 |
| Codon Adaptation Index (CAI) | 0.72 | 0.87 | 0.96 | 0.97 | 1 | 0.96 | 0.96 |
| GC Content | 41% | 51.6% | 60.0% | 60.3% | 62.9% | 59.9% | 59.3% |
| Relative Synonymous Codon Usage (RSCU) | 0.853 | 1.68 | 2.49 | 2.62 | 2.74 | 2.48 | 2.44 |
| Codon Pair Bias | 0.115 | 0.16 | 0.34 | 0.13 | 0.10 | 0.28 | 0.33 |
| Effective number of codons | 51.5 | 41.7 | 24.9 | 23.4 | 20.0 | 24.9 | 25.5 |

TABLE 5-continued

Codon Optimized FIX Nucleotide Sequences

| Plasmid ID | SEQ ID no. |
|---|---|
| LV-FIX-R338L-co6 | codon optimized FiX-co6 with R338L under ET promoter in LV-expression system |

Example 6: FIX-Co1 (FIX-192) Improves Expression In Vivo by 3-Fold Over the Unmodified FIX (FIX-194)

To compare the expression of FIX-co1 to unmodified FIX, their coding sequence was placed under an ET promoter and cloned into pcDNA3 backbone, where the CMV promoter has been replaced by the ET promoter. The resulting plasmids (TABLE 5, plasmids coding for FIX variants), FIX-194 and FIX-192, drives the expression of wild type FIX and codon optimized FIX-co1, respectively. The expression of FIX-194 and FIX-192 were evaluated in HemB mice by hydrodynamic injection (as described above). The plasma samples were collected at 72 hours post injection, and the activity and antigen level of FIX were determined by FIX chromogenic assay and FIX ELISA assay, respectively.

Figure 8:
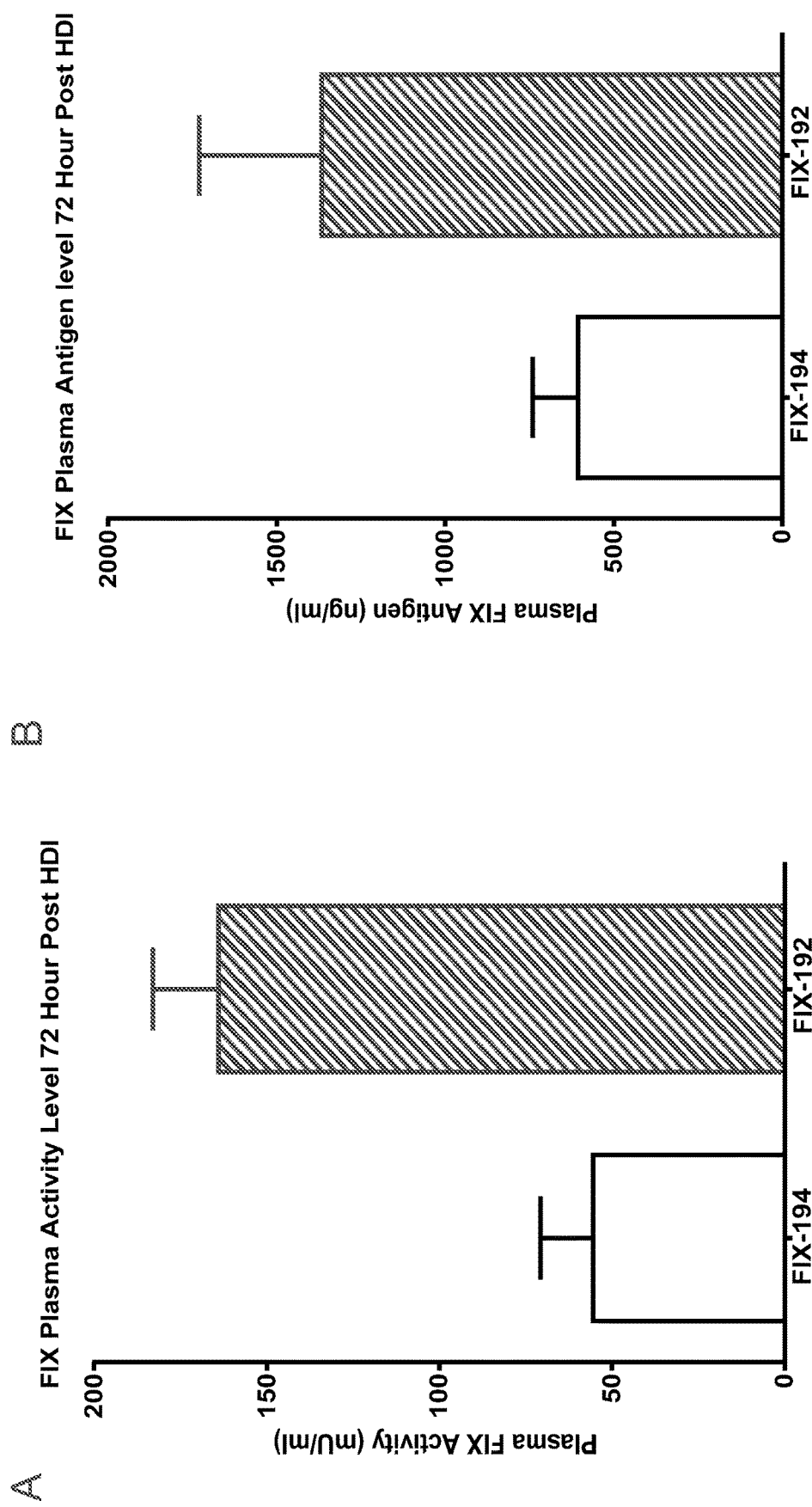
FIG. 8A shows plasma FIX activity (mU/mL) 72 hours after hydrodynamic injection of plasmid DNA encoding the FIX-192 and FIX-194 transgenes.
FIG. 8B shows plasma FIX antigen (ng/mL) 72 hours after hydrodynamic injection of plasmid DNA encoding the FIX-192 and FIX-194 transgenes. Two ml of plasmid solutions were administered into HemB mice via tail vein injection within 4-7 seconds. FIX-194 is unmodified FIX under ET promoter in pcDNA while FIX-192 is a codon optimized FIX-001 under ET promoter in pcDNA.

As shown in FIG. 8, at 72 hours after hydrodynamic injection of the expression plasmid at 10 ug DNA/mice, the plasma FIX activities were found to be 165±19 mU/mL and 56±15 mU/mL from the animals treated with FIX-192 (FIX-co1) and FIX-194 (unmodified FIX), respectively. Correlating with FIX activity, the circulating FIX antigen level was also higher with FIX-co1 treated animals at 1367±362 ng/mL, compared to 607±134 ng/mL post FIX-194 treatment. Together, these data indicate that the codon optimized FIX-co1 improved the expression over unmodified FIX by 3-fold.

Example 7: Evaluate the Expression of all Codon-Optimized FIX Variants by Hydrodynamic Injection In addition, a nature occurring variant R338L that increases the specificity of activity of FIX, was also incorporated into the codon optimized FIX variants and cloned into lentiviral plasmid backbone under the control of ET promoter (Table 5, plasmids encoding FIX variants). Expression driven by these constructs was evaluated in HemB mice by hydrodynamic injection at a dose of 5 ug DNA/mouse. Plasma samples were collected at 96 hr post plasmid DNA infusion and analyzed for circulating FIX activity and FIX antigen level by FIX chromogenic activity assay and FIX ELISA assay, respectively.

Figure 9:
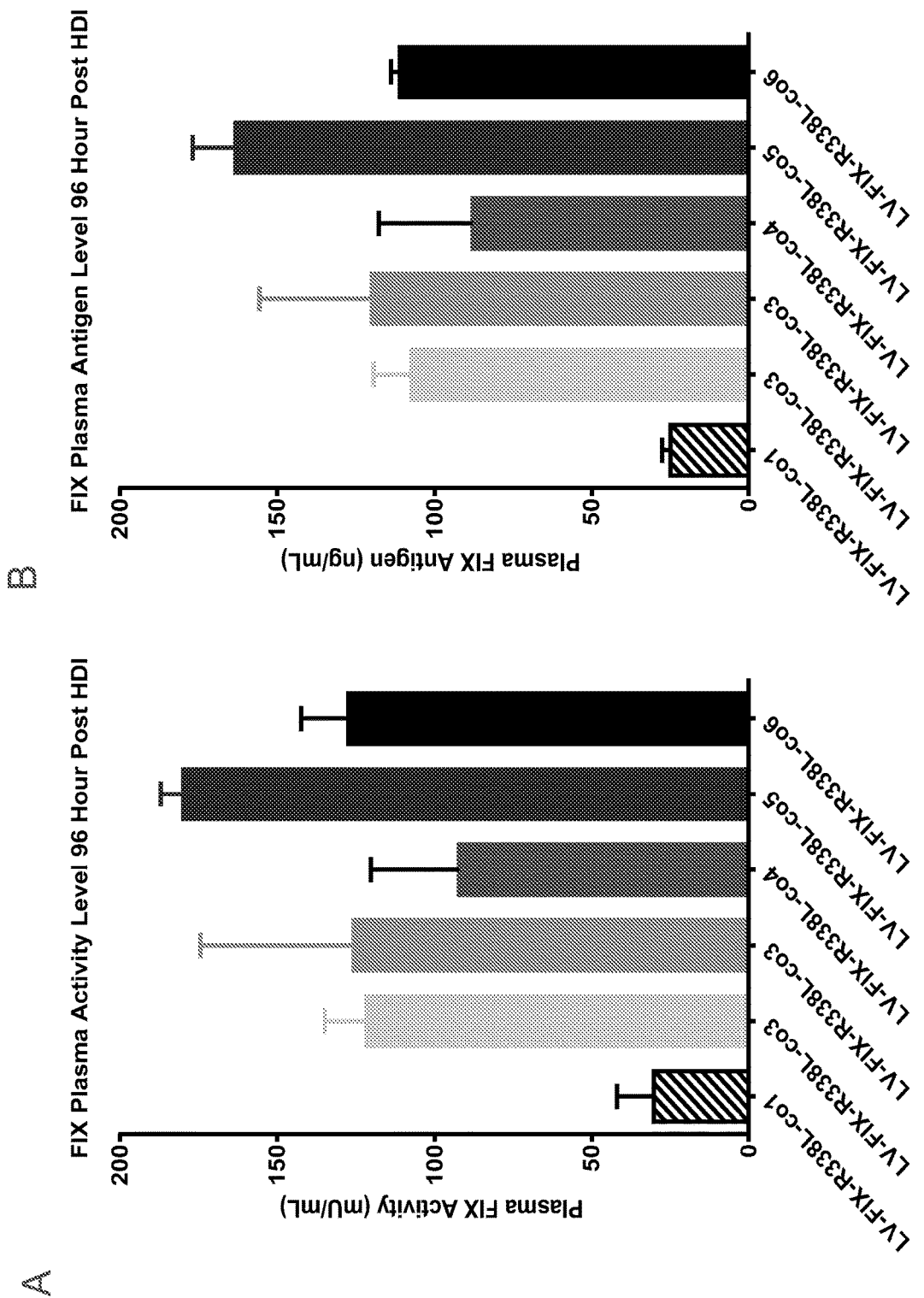
FIG. 9A shows plasma FIX activity (mU/mL) 96 hours after hydrodynamic injection of plasmid DNA encoding the six codon optimized FIX variants: (i) LV-FIX-R338L-co1, which is codon optimized FIX-co1 with R338L under ET promoter in LV-expression system; (ii) LV-FIX-R338L-co2, which is codon optimized FIX-co2 with R338L under ET promoter in LV-expression system; (iii) LV-FIX-R338L-co3, which is codon optimized FIX-co3 with R338L under ET promoter in LV-expression system; (iv) LV-FIX-R338L-co4, which is codon optimized FIX-co4 with R338L under ET promoter in LV-expression system; (v) LV-FIX-R338L-co5, which is codon optimized FIX-co5 with R338L under ET promoter in LV-expression system; and (vi) LV-FIX-R338L-co6, which is codon optimized FIX-co6 with R338L under ET promoter in LV-expression system.
FIG. 9B shows plasma FIX antigen (ng/mL) 96 hours after hydrodynamic injection of plasmid DNA encoding (i) LV-FIX-R338L-aco1; (ii) LV-FIX-R338L-co2; (iii) LV-FIX-R338L-co3; (iv) LV-FIX-R338L-co4; (v) LV-FIX-R338L-co5; and (vi) LV-FIX-R338L-co6.

The FIX activity and antigen in plasma sampled at 96 hours after injection were summarized in Table 6 and FIG. 9. All five codon-optimized FIX variants (FIX-R338L-co2 to -co6) drove at least 3.5-fold higher level of expression than that of FIX-R338L-co1, and the highest level was observed with pLV-FIX-R338L-co5, which resulted in 6 fold additional improvement in expression over FIX-R338-co1.

Examples 8: Evaluation of the Expression of Codon Optimized FIX Variants in HemB Mice by Lentiviral Vectors The positive effect of codon optimization on FIX expression level will be confirmed by Lentiviral vectors mediated long term FIX expression using Lenti virus encoding the codon optimized FIX transgenes. Lentiviral vectors encoding FIX-R338L-co1, -co2, -co3, -co5, -co6 were produced using transient transfection of 293T cells. Concentrated Lenti-viral vectors will be administered into HemB mice via intravenous injection, and circulating FIX level will be monitored for three months post Lenti vector infusion by FIX activity and antigen assays.

Example 9. FIX Codon Optimization Variants and Expression

Adeno-associated virus (AAV)-mediated human factor IX (FIX) gene therapy has demonstrated long-term FIX expression in Hemophilia B (HemB) patients with up to 6% circulating FIX activity, which, however, did not fully protect patients from spontaneous bleeds. In addition, the high AAV doses were associated with liver toxicity resulting in loss of FIX expression. Here we sought to maximize FIX expression by employing a variety of codon optimization strategies, which could potentially increase the circulating FIX levels or reduce the vector doses.

Six FIX variants were generated by using synonymous codons, which were adjusted to maintain FIX mRNA stability, and the codon usages were changed to human bias as indicated by higher human codon adaption index (CAI). In addition to the overall increase of the CAI, the distribution of high CAI was varied through the coding sequences to potentially modulate the rate of protein translation from the start to finish. Moreover, the R338L mutation was incorporated to increase the specific activity. All the variants were then cloned into expression plasmids and tested in HemB mice by hydrodynamic injection. Compared to the wild type FIX, the codon-optimized variants achieved 3 to 15-fold higher circulating FIX antigen level in HemB mice; in combination with R338L mutation, the circulating FIX activity level of the best variant was increased 75-fold or

TABLE 6

Circulating FIX activity and antigen level at 96 hr post FIX transgene infusion

| Plasmid ID | | pLV-FIX-R338L-co1 | pLV-FIX-R338L-c02 | LV-FIX-R338L-c03 | pLV-FIX-R338L-c04 | pLV-FIX-R338L-co5 | pLV-FIX-R338L-c06 |
|---|---|---|---|---|---|---|---|
| FIX activity (mU/mL) | | 30 ± 12 | 122 ± 13 | 126 ± 49 | 92 ± 28 | 159 ± 37 | 127 ± 15 |
| FIX antigen (ng/mL) | | 25 ± 2 | 108 ± 12 | 120 ± 35 | 88 ± 30 | 146 ± 33 | 111 ± 3 |
| Fold increase vs LV-FIX-R338L-co1 | Activity | 1 | 4.9 | 5.0 | 3.7 | 6.4 | 5.1 |
| | Antigen | 1 | 4.3 | 4.8 | 3.5 | 5.8 | 4.4 | higher. The long-term expression of these variants delivered by lentiviral vectors will be evaluated in HemB mice, which could identify an optimal FIX transgene for effective FIX gene therapy.

```
SEQUENCES
optimized human factor IX nucleotide sequence
                                                                              SEQ ID NO: 1
ATGCAGAGAGTCAACATGATTATGGCTGAGTCACCTGGGCTGATTACTATTTGCCTGCTG

GGCTACCTGCTGTCCGCCGAGTGTACCGTGTTCCTGGACCATGAGAACGCAAATAAGATC

CTGAACAGGCCCAAAAGATACAATAGTGGGAAGCTGGAGGAATTTGTGCAGGGCAACCTG

GAGAGAGAATGCATGGAGGAAAAGTGTAGCTTCGAGGAAGCCCGCGAGGTGTTTGAAAAT

ACAGAGCGAACCACAGAGTTCTGGAAGCAGTATGTGGACGGCGATCAGTGCGAGAGCAAC

CCCTGTCTGAATGGCGGAAGTTGCAAAGACGATATCAACTCATACGAATGCTGGTGTCCT

TTCGGGTTTGAAGGCAAAAATTGCGAGCTGGACGTGACATGTAACATTAAGAATGGACGG

TGCGAGCAGTTTTGTAAAAACTCTGCCGATAATAAGGTGGTGTGCAGCTGTACTGAAGGA

TATCGCCTGGCTGAGAACCAGAAGTCCTGCGAACCAGCAGTGCCCTTCCCTTGTGGGAGG

GTGAGCGTCTCCCAGACTTCAAAACTGACCAGAGCAGAGACAGTGTTTCCCGACGTGGAT

TACGTCAACAGCACTGAGGCCGAAACCATCCTGGACAACATTACTCAGTCTACCCAGAGT

TTCAATGACTTTACTCGGGTGGTCGGGGGCGAGGATGCTAAACCAGGCCAGTTCCCCTGG

CAGGTGGTCCTGAACGGAAAGGTGGATGCATTTTGCGGAGGGTCTATCGTGAATGAGAAA

TGGATTGTCACCGCCGCTCACTGCGTGGAAACCGGAGTCAAGATCACAGTGGTCGCTGGG

GAGCACAACATTGAGGAAACAGAACATACTGAGCAGAAGCGGAATGTGATCCGCATCATT

CCTCACCATAACTACAATGCAGCCATCAACAAATACAATCATGACATTGCCCTGCTGGAA

CTGGATGAGCCTCTGGTGCTGAACAGCTACGTCACTCCAATCTGCATTGCTGACAAAGAG

TATACCAATATCTTCCTGAAGTTTGGATCAGGGTACGTGAGCGGCTGGGGAAGAGTCTTC

CACAAGGGCAGGAGCGCCCTGGTGCTCCAGTATCTGCGAGTGCCTCTGGTCGATCGAGCT

ACCTGTCTGAGGTCTACCAAGTTTACAATCTACAACAACATGTTCTGCGCTGGGTTTCAC

GAGGGAGGACGAGACTCCTGTCAGGGCGATTCTGGGGGCCCACATGTGACAGAGGTCGAA

GGCACCAGCTTCCTGACTGGCATCATTTCCTGGGGAGAGGAATGTGCAATGAAGGGAAAA

TACGGGATCTACACCAAAGTGAGCCGCTATGTGAACTGGATCAAGGAAAAAACCAAACTG

ACCTAATGA original human factor IX nucleotide sequence
                                                                              SEQ ID NO: 2
ATGCAGCGCGTGAACATGATCATGGCAGAATCACCAGGCCTCATCACCATCTGCCTTTTA

GGATATCTACTCAGTGCTGAATGTACAGTTTTTCTTGATCATGAAAACGCCAACAAAATT

CTGAATCGGCCAAAGAGGTATAATTCAGGTAAATTGGAAGAGTTTGTTCAAGGGAATCTA

GAGAGAGAATGTATGGAAGAAAAGTGTAGTTTTGAAGAAGCACGAGAAGTTTTTGAAAAC

ACTGAAAGAACAACTGAATTTTGGAAGCAGTATGTTGATGGAGATCAGTGTGAGTCCAAT

CCATGTTTAAATGGCGGCAGTTGCAAGGATGACATTAATTCCTATGAATGTTGGTGTCCC

TTTGGATTTGAAGGAAAGAACTGTGAATTAGATGTAACATGTAACATTAAGAATGGCAGA

TGCGAGCAGTTTTGTAAAAATAGTGCTGATAACAAGGTGGTTTGCTCCTGTACTGAGGGA

TATCGACTTGCAGAAAACCAGAAGTCCTGTGAACCAGCAGTGCCATTTCCATGTGGAAGA

GTTTCTGTTTCACAAACTTCTAAGCTCACCCGTGCTGAGACTGTTTTTCCTGATGTGGAC

TATGTAAATTCTACTGAAGCTGAAACCATTTTGGATAACATCACTCAAAGCACCCAATCA
```

-continued

```
TTTAATGACTTCACTCGGGTTGTTGGTGGAGAAGATGCCAAACCAGGTCAATTCCCTTGG

CAGGTTGTTTTGAATGGTAAAGTTGATGCATTCTGTGGAGGCTCTATCGTTAATGAAAAA

TGGATTGTAACTGCTGCCCACTGTGTTGAAACTGGTGTTAAAATTACAGTTGTCGCAGGT

GAACATAATATTGAGGAGACAGAACATACAGAGCAAAAGCGAAATGTGATTCGAATTATT

CCTCACCACAACTACAATGCAGCTATTAATAAGTACAACCATGACATTGCCCTTCTGGAA

CTGGACGAACCCTTAGTGCTAAACAGCTACGTTACACCTATTTGCATTGCTGACAAGGAA

TACACGAACATCTTCCTCAAATTTGGATCTGGCTATGTAAGTGGCTGGGGAAGAGTCTTC

CACAAAGGGAGATCAGCTTTAGTTCTTCAGTACCTTAGAGTTCCACTTGTTGACCGAGCC

ACATGTCTTCGATCTACAAAGTTCACCATCTATAACAACATGTTCTGTGCTGGCTTCCAT

GAAGGAGGTAGAGATTCATGTCAAGGAGATAGTGGGGGACCCCATGTTACTGAAGTGGAA

GGGACCAGTTTCTTAACTGGAATTATTAGCTGGGGTGAAGAGTGTGCAATGAAAGGCAAA

TATGGAATATATACCAAGGTATCCCGGTATGTCAACTGGATTAAGGAAAAAACAAAGCTC

ACTTGATAA
``` amino acid sequence of human R338L FIX
SEQ ID NO: 3

FIX Signal Peptide: MQRVNMIMAE SPGLITICLL GYLLSAEC
FIX Propeptide: TVFLDHENAN KILNRPKR

```
        1     YNSGKLEEFV QGNLERECME EKCSFEEARE VFENTERTTE FWKQYVDGDQ

51     CESNPCLNGG SCKDDINSYE CWCPFGFEGK NCELDVTCNI KNGRCEQFCK

101     NSADNKVVCS CTEGYRLAEN QKSCEPAVPF PCGRVSVSQT SKLTRAETVF

151     PDVDYVNSTE AETILDNITQ STQSFNDFTR VVGGEDAKPG QFPWQVVLNG

201     KVDAFCGGSI VNEKWIVTAA HCVETGVKIT VVAGEHNIEE TEHTEQKRNV

251     IRIIPHHNYN AAINKYNHDI ALLELDEPLV LNSYVTPICI ADKEYTNIFL

300     KFGSGYVSGW GRVFHKGRSA LVLQYLRVPL VDRATCLLST KFTIYNNMFC

351     AGFHEGGRDS CQGDSGGPHV TEVEGTSFLT GIISWGEECA MKGKYGIYTK

401     VSRYVNWIKE KTKLT
```

Potential Splice Site
SEQ ID NO: 4

GGTGAT

Potential Splice Site
SEQ ID NO: 5

GGTAAG

Destabilizing Sequence
SEQ ID NO: 6

ATTTA poly-T Sequence
SEQ ID NO: 7

TTTTTT poly-A Sequence
SEQ ID NO: 8

AAAAAA poly-A Sequence
SEQ ID NO: 9

AATAAA poly-A Sequence
SEQ ID NO: 10

ATTAAA antiviral motif
SEQ ID NO: 11

TGTGT

-continued

AU Rich Sequence Elements (ARE)

ATTTTATT
SEQ ID NO: 14

AU Rich Sequence Elements (ARE)

ATTTTTAA
SEQ ID NO: 15

CTP peptide

DPRFQDSSSSKAPPPSLPSPSRLPGPSDTPIL
SEQ ID NO: 17

CTP peptide

SSSSKAPPPSLPSPSRLPGPSDTPILPQ
SEQ ID NO: 18 albumin-binding peptides core sequence

DICLPRWGCLW
SEQ ID NO: 19

PAS Sequence

ASPAAPAPASPAAPAPSAPA
SEQ ID NO: 20

PAS Sequence

AAPASPAPAAPSAPAPAAPS
SEQ ID NO: 21

PAS Sequence

APSSPSPSAPSSPSPASPSS
SEQ ID NO: 22

PAS Sequence

APSSPSPSAPSSPSPASPS
SEQ ID NO: 23

PAS Sequence

SSPSAPSPSSPASPSPSSPA
SEQ ID NO: 24

PAS Sequence

AASPAAPSAPPAAASPAAPSAPPA
SEQ ID NO: 25

PAS Sequence

ASAAAPAAASAAASAPSAAA
SEQ ID NO: 26

SEQ ID NO: 27

SEQ ID NO: 28 human IgG1 amino acids 233-236

ELLG
SEQ ID NO: 29

XTEN AE42-4, protein sequence

GAPGSPAGSPTSTEEGTSESATPESGPGSEPATSGSETPASS
SEQ ID NO: 30

XTEN AE42-4, DNA sequence

GGCGCGCCAGGTTCTCCTGCTGGCTCCCCCACCTCAACAGAAGAGGGGACAAGCGAAAGC

GCTACGCCTGAGAGTGGCCCTGGCTCTGAGCCAGCCACCTCCGGCTCTGAAACCCCTGCC

TCGAGC
SEQ ID NO: 31

XTEN AE144-2A, protein sequence

TSTEPSEGSAPGSPAGSPTSTEEGTSTEPSEGSAPGTSTEPSEGSAPGTSESATPESGPG

TSTEPSEGSAPGTSESATPESGPGSEPATSGSETPGTSTEPSEGSAPGTSTEPSEGSAPG

TSESATPESGPGTSESATPESGPG
SEQ ID NO: 32

XTEN AE144-2A, DNA sequence

GGCGCGCCAACCAGTACGGAGCCGTCCGAGGGGAGCGCACCAGGAAGCCCGGCTGGGAGC

CCGACTTCTACCGAAGAGGGTACATCTACCGAACCAAGTGAAGGTTCAGCACCAGGCACC
SEQ ID NO: 33

-continued

TCAACAGAACCCTCTGAGGGCTCGGCGCCTGGTACAAGTGAGTCCGCCACCCCAGAATCC

GGGCCTGGGACAAGCACAGAACCTTCGGAAGGGAGTGCCCCTGGAACATCCGAATCGGCA

ACCCCAGAATCAGGGCCAGGATCTGAGCCCGCGACTTCGGGCTCCGAGACGCCTGGGACA

TCCACCGAGCCCTCCGAAGGATCAGCCCCAGGCACCAGCACGGAGCCCTCTGAGGGAAGC

GCACCTGGTACCAGCGAAAGCGCAACTCCCGAATCAGGTCCCGGTACGAGCGAGTCGGCG

ACCCCGGAGAGCGGGCCAGGTGCCTCGAGC

XTEN AE144-3B, protein sequence  
SEQ ID NO: 34

SPAGSPTSTEEGTSESATPESGPGSEPATSGSETPGTSESATPESGPGTSTEPSEGSAPG

TSTEPSEGSAPGTSTEPSEGSAPGTSTEPSEGSAPGTSTEPSEGSAPGTSTEPSEGSAPG

SPAGSPTSTEEGTSTEPSEGSAPG

XTEN AE144-3B, DNA sequence  
SEQ ID NO: 35

GGCGCGCCAAGTCCCGCTGGAAGCCCAACTAGCACCGAAGAGGGGACCTCAGAGTCCGCC

ACCCCCGAGTCCGGCCCTGGCTCTGAGCCTGCCACTAGCGGCTCCGAGACTCCTGGCACA

TCCGAAAGCGCTACACCCGAGAGTGGACCCGGCACCTCTACCGAGCCCAGTGAGGGCTCC

GCCCCTGGAACAAGCACCGAGCCCAGCGAAGGCAGCGCCCCAGGGACCTCCACAGAGCCC

AGTGAAGGCAGTGCTCCTGGCACCAGCACCGAACCAAGCGAGGGCTCTGCACCCGGGACC

TCCACCGAGCCAAGCGAAGGCTCTGCCCCTGGCACTTCCACCGAGCCCAGCGAAGGCAGC

GCCCCTGGGAGCCCCGCTGGCTCTCCCACCAGCACTGAGGAGGGCACATCTACCGAACCA

AGTGAAGGCTCTGCACCAGGTGCCTCGAGC

XTEN AE144-4A, protein sequence  
SEQ ID NO: 36

TSESATPESGPGSEPATSGSETPGTSESATPESGPGSEPATSGSETPGTSESATPESGPG

TSTEPSEGSAPGTSESATPESGPGSPAGSPTSTEEGSPAGSPTSTEEGSPAGSPTSTEEG

TSESATPESGPGTSTEPSEGSAPG

XTEN AE144-4A, DNA sequence  
SEQ ID NO: 37

GGCGCGCCAACGTCCGAAAGTGCTACCCCTGAGTCAGGCCCTGGTAGTGAGCCTGCCACA

AGCGGAAGCGAAACTCCGGGGACCTCAGAGTCTGCCACTCCCGAATCGGGGCCAGGCTCT

GAACGGCCACTTCAGGGAGCGAAACACCAGGAACATCGGAGAGCGCTACCCCGGAGAGC

GGGCCAGGAACTAGTACTGAGCCTAGCGAGGGAAGTGCACCTGGTACAAGCGAGTCCGCC

ACACCCGAGTCTGGCCCTGGCTCTCCAGCGGGCTCACCCACGAGCACTGAAGAGGGCTCT

CCCGCTGGCAGCCCAACGTCGACAGAAGAAGGATCACCAGCAGGCTCCCCCACATCAACA

GAGGAGGGTACATCAGAATCTGCTACTCCCGAGAGTGGACCCGGTACCTCCACTGAGCCC

AGCGAGGGGAGTGCACCAGGTGCCTCGAGC

XTEN AE144-5A, protein sequence  
SEQ ID NO: 38

TSESATPESGPGSEPATSGSETPGTSESATPESGPGSEPATSGSETPGTSESATPESGPG

TSTEPSEGSAPGSPAGSPTSTEEGTSESATPESGPGSEPATSGSETPGTSESATPESGPG

SPAGSPTSTEEGSPAGSPTSTEEG

XTEN AE144-5A, DNA sequence  
SEQ ID NO: 39

GGCGCGCCAACATCAGAGAGCGCCACCCCTGAAAGTGGTCCCGGGAGCGAGCCAGCCACA

TCTGGGTCGGAAACGCCAGGCACAAGTGAGTCTGCAACTCCCGAGTCCGGACCTGGCTCC

GAGCCTGCCACTAGCGGCTCCGAGACTCCGGGAACTTCCGAGAGCGCTACACCAGAAAGC

-continued

GGACCCGGAACCAGTACCGAACCTAGCGAGGGCTCTGCTCCGGGCAGCCCAGCCGGCTCT

CCTACATCCACGGAGGAGGGCACTTCCGAATCCGCCACCCCGGAGTCAGGGCCAGGATCT

GAACCCGCTACCTCAGGCAGTGAGACGCCAGGAACGAGCGAGTCCGCTACACCGGAGAGT

GGGCCAGGGAGCCCTGCTGGATCTCCTACGTCCACTGAGGAAGGGTCACCAGCGGGCTCG

CCCACCAGCACTGAAGAAGGTGCCTCGAGC

XTEN AE144-6B, protein sequence

SEQ ID NO: 40

TSTEPSEGSAPGTSESATPESGPGTSESATPESGPGTSESATPESGPGSEPATSGSETPG

SEPATSGSETPGSPAGSPTSTEEGTSTEPSEGSAPGTSTEPSEGSAPGSEPATSGSETPG

TSESATPESGPGTSTEPSEGSAPG

XTEN AE144-6B, DNA sequence

SEQ ID NO: 41

GGCGCGCCAACATCTACCGAGCCTTCCGAAGGCTCTGCCCCTGGGACCTCAGAATCTGCA

ACCCCTGAAAGCGGCCCTGGAACCTCCGAAAGTGCCACTCCCGAGAGCGGCCCAGGGACA

AGCGAGTCAGCAACCCCTGAGTCTGGACCCGGCAGCGAGCCTGCAACCTCTGGCTCAGAG

ACTCCCGGCTCAGAACCCGCTACCTCAGGCTCCGAGACACCCGGCTCTCCTGCTGGGAGT

CCCACTTCCACCGAGGAAGGAACATCCACTGAGCCTAGTGAGGGCTCTGCCCCTGGAACC

AGCACAGAGCCAAGTGAGGGCAGTGCACCAGGATCCGAGCCAGCAACCAGCGGGTCCGAG

ACTCCCGGGACCTCTGAGTCTGCCACCCCAGAGAGCGGACCCGGCACTTCAACCGAGCCC

TCCGAAGGATCAGCACCAGGTGCCTCGAGC

XTEN AG144-1, protein sequence

SEQ ID NO: 42

PGSSPSASTGTGPGSSPSASTGTGPGTPGSGTASSSPGSSTPSGATGSPGSSPSASTGTG

PGASPGTSSTGSPGTPGSGTASSSPGSSTPSGATGSPGTPGSGTASSSPGASPGTSSTGS

PGASPGTSSTGSPGTPGSGTASSS

XTEN AG144-1, DNA sequence

SEQ ID NO: 43

GGCGCGCCACCCGGGTCGTCCCCGTCGGCGTCCACCGGAACAGGGCCAGGGTCATCCCCG

TCAGCGTCGACTGGGACGGGACCCGGGACACCCGGTTCGGGGACTGCATCCTCCTCGCCT

GGTTCGTCCACCCCGTCAGGAGCCACGGGTTCGCCGGGAAGCAGCCCAAGCGCATCCACT

GGTACAGGGCCTGGGGCTTCACCGGGTACTTCATCCACGGGGTCACCGGGAACGCCCGGA

TCGGGGACGGCTTCCTCATCACCAGGATCGTCAACACCCTCGGGCGCAACGGGCAGCCCC

GGAACCCCTGGTTCGGGTACGCGTCGTCGAGCCCCGGTGCGAGCCCGGGAACAAGCTCG

ACAGGATCGCCTGGGGCGTCACCCGGCACGTCGAGCACAGGCAGCCCCGGAACCCCTGGA

TCGGGAACCGCGTCGTCAAGCGCCTCGAGC

XTEN AG144-A, protein sequence

SEQ ID NO: 44

GASPGTSSTGSPGSSPSASTGTGPGSSPSASTGTGPGTPGSGTASSSPGSSTPSGATGSP

GSSPSASTGTGPGASPGTSSTGSPGTPGSGTASSSPGSSTPSGATGSPGTPGSGTASSSP

GASPGTSSTGSPGASPGTSSTGSP

XTEN AG144-A, DNA sequence

SEQ ID NO: 45

GGCGCGCCAGGTGCCTCGCCGGGAACATCATCAACTGGTTCACCCGGGTCATCCCCCTCG

GCCTCAACCGGGACGGGTCCCGGCTCATCCCCCAGCGCCAGCACTGGAACAGGTCCTGGC

ACTCCTGGTTCCGGTACGGCATCGTCATCCCCGGGAAGCTCAACACCGTCCGGAGCGACA

GGATCACCTGGCTCGTCACCTTCGGCGTCAACTGGAACGGGGCCAGGGGCCTCACCCGGA

ACGTCCTCGACTGGGTCGCCTGGTACGCCGGGATCAGGAACGGCCTCATCCTCGCCTGGG

-continued

TCCTCAACGCCCTCGGGTGCGACTGGTTCGCCGGGAACTCCTGGCTCGGGGACGGCCTCG

TCGTCGCCTGGGGCATCACCGGGGACGAGCTCCACGGGGTCCCCTGGAGCGTCACCGGGG

ACCTCCTCGACAGGTAGCCCGGCCTCGAGC

XTEN AG144-B, protein sequence
SEQ ID NO: 46

GTPGSGTASSSPGSSTPSGATGSPGASPGTSSTGSPGTPGSGTASSSPGSSTPSGATGSP

GSSPSASTGTGPGSSPSASTGTGPGSSTPSGATGSPGSSTPSGATGSPGASPGTSSTGSP

GASPGTSSTGSPGASPGTSSTGSP

XTEN AG144-B, DNA sequence
SEQ ID NO: 47

GGCGCGCCAGGTACACCGGGCAGCGGCACGGCTTCGTCGTCACCCGGCTCGTCCACACCG

TCGGAGCTACGGGAAGCCCAGGAGCGTCACCGGGAACGTCGTCAACGGGGTCACCGGGT

ACGCCAGGTAGCGGCACGGCCAGCAGCTCGCCAGGTTCATCGACCCCGTCGGGAGCGACT

GGGTCGCCCGGATCAAGCCCGTCAGCTTCCACTGGAACAGGACCCGGGTCGTCGCCGTCA

GCCTCAACGGGGACAGGACCTGGTTCATCGACGCCGTCAGGGGCGACAGGCTCGCCCGGA

TCGTCAACACCCTCGGGGGCAACGGGGAGCCCTGGTGCGTCGCCTGGAACCTCATCCACC

GGAAGCCCGGGGGCCTCGCCGGGTACGAGCTCCACGGGATCGCCCGGAGCGTCCCCCGGA

ACTTCAAGCACAGGGAGCCCTGCCTCGAGC

XTEN AG144-C, protein sequence
SEQ ID NO: 48

GTPGSGTASSSPGASPGTSSTGSPGASPGTSSTGSPGASPGTSSTGSPGSSPSASTGTGP

GTPGSGTASSSPGASPGTSSTGSPGASPGTSSTGSPGASPGTSSTGSPGSSTPSGATGSP

GSSTPSGATGSPGASPGTSSTGSP

XTEN AG144-C, DNA sequence
SEQ ID NO: 49

GGCGCGCCAGGTACACCCGGATCGGGTACAGCGTCATCGAGCCCCGGTGCGTCACCTGGT

ACGTCGAGCACGGGGTCGCCAGGGGCGTCCCCTGGGACGTCCTCAACAGGCTCGCCCGGT

GCGTCACCCGGCACGTCGTCCACGGGTTCACCTGGTAGCTCCCCTTCCGCGTCCACTGGC

ACCGGGCCTGGAACTCCGGGGAGCGGCACAGCGAGCTCGTCGCCGGGAGCATCGCCTGGG

ACATCGAGCACCGGGTCGCCAGGAGCATCGCCCGGAACATCCAGCACAGGAAGCCCCGGC

GCGTCGCCCGGGACATCAAGCACAGGTTCCCCGGGATCGAGCACGCCGTCCGGAGCCACT

GGATCACCAGGGAGCTCGACACCTTCCGGCGCAACGGGATCGCCCGGAGCCAGCCCGGGT

ACGTCAAGCACTGGCTCCCCTGCCTCGAGC

XTEN AG144-F, protein sequence
SEQ ID NO: 50

GSSPSASTGTGPGSSPSASTGTGPGASPGTSSTGSPGASPGTSSTGSPGSSTPSGATGSP

GSSPSASTGTGPGASPGTSSTGSPGSSPSASTGTGPGTPGSGTASSSPGSSTPSGATGSP

GSSTPSGATGSPGASPGTSSTGSP

XTEN AG144-F, DNA sequence
SEQ ID NO: 51

GGCGCGCCAGGCTCCAGCCCCTCCGCGAGCACGGGAACCGGACCAGGTTCGTCACCCTCA

GCATCAACGGGACGGGACCGGGGCGTCACCAGGAACGTCCTCCACCGGCTCGCCGGGT

GCATCACCCGGAACGTCATCGACCGGATCGCCAGGGAGCTCGACGCCATCAGGCGCAACA

GGATCACCTGGCTCAAGCCCTAGCGCGTCAACCGGCACGGGTCCGGGTGCCTCCCCTGGC

ACGTCCAGCACCGGATCACCCGGATCGAGCCCATCCGCCTCAACCGGAACCGGACCCGGT

```
ACACCAGGGTCGGGAACAGCCTCCTCGTCACCAGGCTCCTCAACCCCCTCGGGAGCCACG

GGTTCGCCCGGTTCGTCAACGCCTTCCGGAGCAACTGGTAGCCCCGGAGCATCGCCAGGA

ACTTCGAGCACGGGTCGCCCGCCTCGAGC
``` original human factor IX amino acid sequence

SEQ ID NO: 52

```
MQRVNMIMAESPGLITICLLGYLLSAECTVFLDHENANKILNRPKRYNSGKLEEFVQGNLERECMEEKCSFEEAREVF

ENTERTTEFWKQYVDGDQCESNPCLNGGSCKDDINSYECWCPFGFEGKNCELDVTCNIKNGRCEQFCKNSADNKVVCS

CTEGYRLAENQKSCEPAVPFPCGRVSVSQTSKLTRAETVFPDVDYVNSTEAETILDNITQSTQSFNDFTRVVGGEDAK

PGQFPWQVVLNGKVDAFCGGSIVNEKWIVTAAHCVETGVKITVVAGEHNIEETEHTEQKRNVIRIIPHHNYNAAINKY

NHDIALLELDEPLVLNSYVTPICIADKEYTNIFLKFGSGYVSGWGRVFHKGRSALVLQYLRVPLVDRATCLRSTKFTI

YNNMFCAGFHEGGRDSCQGDSGGPHVTEVEGTSFLTGIISWGEECAMKGKYGIYTKVSRYVNWIKEKTKLT
``` nucleotide sequence of factor IX variant, R338L.

SEQ ID NO: 53

```
ATGCAGAGAGTCAACATGATTATGGCTGAGTCACCTGGGCTGATTACTATTTGCCTGCTGGGCTACCTGCTGTCCGCC

GAGTGTACCGTGTTCCTGGACCATGAGAACGCAAATAAGATCCTGAACAGGCCCAAAAGATACAATAGTGGGAAGCTG

GAGGAATTTGTGCAGGGCAACCTGGAGAGAGAATGCATGGAGGAAAAGTGTAGCTTCGAGGAAGCCCGCGAGGTGTTT

GAAAATACAGAGCGAACCACAGAGTTCTGGAAGCAGTATGTGGACGGCGATCAGTGCGAGAGCAACCCCTGTCTGAAT

GGCGGAAGTTGCAAAGACGATATCAACTCATACGAATGCTGGTGTCCTTTCGGGTTTGAAGGCAAAAATTGCGAGCTG

GACGTGACATGTAACATTAAGAATGGACGGTGCGAGCAGTTTTGTAAAAACTCTGCCGATAATAAGGTGGTGTGCAGC

TGTACTGAAGGATATCGCCTGGCTGAGAACCAGAAGTCCTGCGAACCAGCAGTGCCCTTCCCTTGTGGGAGGGTGAGC

GTCTCCCAGACTTCAAAACTGACCAGAGCAGAGACAGTGTTTCCCGACGTGGATTACGTCAACAGCACTGAGGCCGAA

ACCATCCTGGACAACATTACTCAGTCTACCCAGAGTTTCAATGACTTTACTCGGGTGGTCGGGGGCGAGGATGCTAAA

CCAGGCCAGTTCCCCTGGCAGGTGGTCCTGAACGGAAAGGTGGATGCATTTTGCGGAGGGTCTATCGTGAATGAGAAA

TGGATTGTCACCGCCGCTCACTGCGTGGAAACCGGAGTCAAGATCACAGTGGTCGCTGGGGAGCACAACATTGAGGAA

ACAGAACATACTGAGCAGAAGCGGAATGTGATCCGCATCATTCCTCACCATAACTACAATGCAGCCATCAACAAATAC

AATCATGACATTGCCCTGCTGGAACTGGATGAGCCTCTGGTGCTGAACAGCTACGTCACTCCAATCTGCATTGCTGAC

AAAGAGTATACCAATATCTTCCTGAAGTTTGGATCAGGGTACGTGAGCGGCTGGGGAAGAGTCTTCCACAAGGGCAGG

AGCGCCCTGGTGCTCCAGTATCTGCGAGTGCCTCTGGTCGATCGAGCTACCTGTCTGCTGTCTACCAAGTTTACAATC

TACAACAACATGTTCTGCGCTGGGTTTCACGAGGGAGGACGAGACTCCTGTCAGGGCGATTCTGGGGGCCCACATGTG

ACAGAGGTCGAAGGCACCAGCTTCCTGACTGGCATCATTTCCTGGGGAGAGGAATGTGCAATGAAGGGAAAATACGGG

ATCTACACCAAAGTGAGCCGCTATGTGAACTGGATCAAGGAAAAAACCAAACTGACCTAA
```

FIX-R338L-co2

SEQ ID NO: 54

```
ATGCAGAGGGTGAACATGATCATGGCCGAGAGCCCCGGCCTGATCACCATCTGCCTGCTGGGCTACCTGCTGAGCGCC

GAGTGCACCGTGTTCCTGGACCACGAGAACGCCAACAAGATCCTGAACAGGCCCAAGAGGTACAACAGCGGCAAGCTG

GAGGAGTTCGTGCAGGGCAACCTGGAGAGGGAGTGCATGGAGGAGAAGTGCAGCTTCGAGGAGGCCAGGGAGGTGTTC

GAGAACACCGAGAGGACCACCGAGTTCTGGAAGCAGTACGTGGACGGCGACCAGTGCGAGAGCAACCCCTGCCTGAAC

GGCGGCAGCTGCAAGGACGACATCAACAGCTACGAGTGCTGGTGCCCCTTCGGCTTCGAGGGCAAGAACTGCGAGCTG

GACGTGACCTGCAACATCAAGAACGGCAGGTGCGAGCAGTTCTGCAAGAACAGCGCCGACAACAAGGTGGTGTGCAGC

TGCACCGAGGGCTACAGGCTGGCCGAGAACCAGAAGAGCTGCGAGCCCGCCGTGCCCTTCCCCTGCGGCAGGGTGAGC

GTGAGCCAGACCAGCAAGCTGACCAGGGCCGAGACCGTGTTCCCCGACGTGGACTACGTGAACAGCACCGAGGCCGAG

ACCATCCTGGACAACATCACCCAGAGCACCCAGAGCTTCAACGACTTCACCAGAGTGGTGGGGGGCGAGGACGCCAAG

CCCGGCCAGTTCCCCTGGCAGGTCGTGCTGAATGGCAAAGTCGATGCCTTCTGCGGGGGCAGCATCGTCAACGAGAAG

TGGATTGTGACTGCCGCCCATTGCGTGGAAACCGGGGTGAAGATCACTGTGGTGGCTGGGGAGCACAACATCGAGGAA
```

-continued

ACCGAGCACACCGAGCAGAAGAGGAACGTGATCAGGATTATCCCCCATCACAACTACAATGCCGCCATCAATAAGTAC

AACCATGATATTGCCCTGCTGGAGCTGGATGAACCCCTGGTCCTGAACAGCTATGTGACTCCCATCTGCATTGCCGAC

AAGGAGTATACCAACATCTTCCTGAAATTTGGCAGCGGCTATGTCTCTGGCTGGGGCAGGGTGTTCCATAAGGGGAGG

AGCGCCCTGGTCCTGCAGTACCTGAGAGTGCCCCTGGTGGACAGGGCCACCTGCCTGCTGAGCACCAAGTTCACCATC

TACAACAATATGTTTTGCGCTGGCTTCCATGAGGGGGGCAGGGACAGCTGCCAGGGGGACAGCGGGGGCCCCCATGTG

ACTGAGGTGGAGGGCACCAGCTTCCTGACCGGCATCATCAGCTGGGGGGAGGAGTGCGCCATGAAGGGGAAGTATGGC

ATCTACACCAAAGTCTCCAGATACGTCAACTGGATCAAGGAGAAGACCAAGCTGACCTAA

FIX-R338L-co3
SEQ ID NO: 55
ATGCAGAGGGTGAACATGATCATGGCCGAGAGCCCCGGCCTGATCACCATCTGCCTGCTGGGCTACCTGCTGAGCGCC

GAGTGCACCGTGTTCCTGGACCACGAGAACGCCAACAAGATCCTGAACAGGCCCAAGAGGTACAACAGCGGCAAGCTG

GAGGAGTTCGTGCAGGGCAACCTGGAGAGGGAGTGCATGGAGGAGAAGTGCAGCTTCGAGGAGGCCAGGGAGGTGTTC

GAGAACACCGAGAGGACCACCGAGTTCTGGAAGCAGTACGTGGACGGCGACCAGTGCGAGAGCAACCCCTGCCTGAAC

GGCGGCAGCTGCAAGGACGACATCAACAGCTACGAGTGCTGGTGCCCCTTCGGCTTCGAGGGCAAGAACTGCGAGCTG

GACGTGACCTGCAACATCAAGAACGGCAGGTGCGAGCAGTTCTGCAAGAACAGCGCCGACAACAAGGTGGTGTGCAGC

TGCACCGAGGGCTACAGGCTGGCCGAGAACCAGAAGAGCTGCGAGCCCGCCGTGCCCTTCCCCTGCGGCAGGGTGAGC

GTGAGCCAGACCAGCAAGCTGACCAGGGCCGAGACCGTGTTCCCCGACGTGGACTACGTGAACAGCACCGAGGCCGAG

ACCATCCTGGACAACATCACCCAGAGCACCCAGAGCTTCAACGACTTCACCAGGGTGGTGGGCGGCGAGGACGCCAAG

CCCGGCCAGTTTCCCTGGCAGGTGGTGCTGAACGGCAAGGTGGACGCCTTCTGCGGCGGCAGCATCGTGAACGAGAAG

TGGATCGTGACCGCTGCCCATTGCGTGGAAACCGGCGTGAAGATCACCGTGGTGGCCGGCGAGCACAACATCGAAGAG

ACCGAGCACACCGAACAGAAAAGGAACGTGATCAGGATCATCCCTCACCATAACTACAATGCCGCCATTAACAAGTAC

AATCACGACATCGCTCTGCTGGAACTGGATGAACCCCTGGTGCTGAACAGCTACGTGACCCCTATCTGCATCGCCGAC

AAGGAGTATACTAACATCTTTCTGAAGTTTGGCAGCGGCTATGTGAGCGGCTGGGGCAGGGTGTTCCACAAAGGCAGG

AGCGCCCTGGTGCTGCAGTACCTGAGGGTGCCCCTGGTGGATAGGGCTACCTGCCTGCTGAGCACCAAGTTCACCATC

TACAACAACATGTTCTGTGCCGGCTTCCACGAAGGCGGCAGGGACTCTTGCCAGGGCGACAGCGGCGGCCCCCATGTG

ACCGAGGTGGAAGGCACTAGCTTTCTGACCGGCATCATCAGCTGGGGCGAGGAGTGCGCCATGAAGGGCAAGTACGGC

ATCTACACTAAGGTGAGCAGGTACGTGAACTGGATCAAAGAAAAGACCAAGCTGACCTAA

FIX-R338L-co4
SEQ ID NO: 56
ATGCAGAGGGTGAACATGATCATGGCCGAGAGCCCCGGCCTGATCACCATCTGCCTGCTGGGCTACCTGCTGAGCGCC

GAGTGCACCGTGTTCCTGGACCACGAGAACGCCAACAAGATCCTGAACAGGCCCAAGAGGTACAACAGCGGCAAGCTG

GAGGAGTTCGTGCAGGGCAACCTGGAGAGGGAGTGCATGGAGGAGAAGTGCAGCTTCGAGGAGGCCAGGGAGGTGTTC

GAGAACACCGAGAGGACCACCGAGTTCTGGAAGCAGTACGTGGACGGCGACCAGTGCGAGAGCAACCCCTGCCTGAAC

GGCGGCAGCTGCAAGGACGACATCAACAGCTACGAGTGCTGGTGCCCCTTCGGCTTCGAGGGCAAGAACTGCGAGCTG

GACGTGACCTGCAACATCAAGAACGGCAGGTGCGAGCAGTTCTGCAAGAACAGCGCCGACAACAAGGTGGTGTGCAGC

TGCACCGAGGGCTACAGGCTGGCCGAGAACCAGAAGAGCTGCGAGCCCGCCGTGCCCTTCCCCTGCGGCAGGGTGAGC

GTGAGCCAGACCAGCAAGCTGACCAGGGCCGAGACCGTGTTCCCCGACGTGGACTACGTGAACAGCACCGAGGCCGAG

ACCATCCTGGACAACATCACCCAGAGCACCCAGAGCTTCAACGACTTCACCAGGGTGGTGGGCGGCGAGGACGCCAAG

CCCGGCCAGTTCCCCTGGCAGGTGGTGCTGAACGGCAAGGTGGACGCCTTCTGCGGCGGCAGCATCGTGAACGAGAAG

TGGATCGTGACCGCCGCCCACTGCGTGGAGACCGGCGTGAAGATCACCGTGGTGGCCGGCGAGCACAACATCGAGGAG

ACCGAGCACACCGAGCAGAAGAGGAACGTGATCAGGATCATCCCCCACCACAACTACAACGCCGCCATCAACAAGTAC

AACCACGACATCGCCCTGCTGGAGCTGGACGAGCCCCTGGTGCTGAACAGCTACGTGACCCCCATCTGCATCGCCGAC

-continued

AAGGAGTACACCAACATCTTCCTGAAGTTCGGCAGCGGCTACGTGAGCGGCTGGGGCAGGGTGTTCCACAAGGGCAGG

AGCGCCCTGGTGCTGCAGTACCTGAGGGTGCCCCTGGTGGACAGGGCCACCTGCCTGCTGAGCACCAAGTTCACCATC

TACAACAACATGTTCTGCGCCGGCTTCCACGAGGGCGGCAGGGACAGCTGCCAGGGCGACAGCGGCGGCCCCCACGTG

ACCGAGGTGGAGGGCACCAGCTTCCTGACCGGCATCATCAGCTGGGGCGAGGAGTGCGCCATGAAGGGCAAGTACGGC

ATCTACACCAAGGTGAGCAGGTACGTGAACTGGATCAAGGAGAAGACCAAGCTGACCTAA

FIX-R338L-co5
SEQ ID NO: 57

ATGCAGAGGGTCAACATGATCATGGCTGAGTCTCCTGGCCTGATCACCATCTGCCTGCTGGGCTATCTGCTGTCCGCT

GAGTGCACTGTCTTCCTGGACCACGAGAACGCCAACAAGATCCTGAACAGGCCCAAGAGGTATAACTCTGGCAAGCTG

GAGGAGTTTGTGCAGGGGAACCTGGAGAGGGAGTGCATGGAGGAGAAGTGCAGCTTCGAGGAGGCCAGGGAGGTGTTT

GAGAACACTGAGAGGACCACCGAGTTCTGGAAGCAGTATGTGGACGGGGACCAGTGCGAGTCTAACCCTTGCCTGAAC

GGGGGCAGCTGCAAGGATGACATCAACAGCTATGAGTGCTGGTGCCCTTTCGGCTTCGAGGGCAAGAACTGCGAGCTG

GATGTGACCTGCAACATCAAGAACGGCAGGTGCGAGCAGTTCTGCAAGAACTCTGCCGACAACAAGGTGGTGTGCAGC

TGCACTGAGGGCTATAGGCTGGCTGAGAACCAGAAGAGCTGTGAGCCTGCTGTGCCCTTCCCCTGCGGCAGAGTGTCT

GTGAGCCAGACCAGCAAGCTGACCAGAGCTGAGACTGTCTTCCCCGACGTGGACTATGTGAACAGCACCGAGGCTGAG

ACCATCCTGGACAACATCACCCAGTCTACCCAGTCTTTCAACGACTTCACCAGAGTGGTGGGGGGCGAGGACGCCAAG

CCTGGCCAGTTCCCCTGGCAGGTCGTGCTGAACGGCAAAGTGGACGCCTTCTGCGGGGGCAGCATCGTCAACGAGAAG

TGGATCGTGACTGCTGCTCACTGCGTGGAAACCGGGGTGAAGATCACCGTGGTGGCCGGCGAGCACAACATCGAGGAG

ACCGAGCACACCGAGCAGAAGAGGAACGTGATCAGGATCATCCCCCACCACAACTACAACGCCGCCATCAACAAGTAC

AACCACGACATCGCCCTGCTGGAGCTGGACGAGCCCCTGGTGCTGAACAGCTACGTGACCCCCATCTGCATCGCCGAC

AAGGAGTACACCAACATCTTCCTGAAGTTCGGCAGCGGCTACGTGAGCGGCTGGGGCAGGGTGTTCCACAAGGGCAGG

AGCGCCCTGGTGCTGCAGTACCTGAGGGTGCCCCTGGTGGACAGGGCCACCTGCCTGCTGAGCACCAAGTTCACCATC

TACAACAACATGTTCTGCGCCGGCTTCCACGAGGGCGGCAGGGACAGCTGCCAGGGCGACAGCGGCGGCCCCCACGTG

ACCGAGGTGGAGGGCACCAGCTTCCTGACCGGCATCATCAGCTGGGGCGAGGAGTGCGCCATGAAGGGCAAGTACGGC

ATCTACACCAAGGTGAGCAGGTACGTGAACTGGATCAAGGAGAAGACCAAGCTGACCTAA

FIX-R338L-c06
SEQ ID NO: 58

ATGCAGAGGGTCAACATGATCATGGCTGAGTCTCCTGGCCTGATCACTATCTGCCTGCTGGGCTACCTGCTGAGCGCC

GAGTGCACTGTCTTCCTGGACCACGAGAACGCCAACAAGATCCTGAACAGGCCCAAGAGATACAACTCTGGCAAGCTG

GAGGAGTTTGTGCAGGGGAACCTGGAGAGGGAGTGCATGGAGGAGAAGTGCAGCTTCGAGGAGGCCAGGGAGGTGTTT

GAGAACACTGAGAGGACCACTGAGTTCTGGAAGCAGTATGTGGACGGGGACCAGTGCGAGTCTAACCCTTGCCTGAAC

GGGGGCAGCTGCAAGGATGACATCAACAGCTACGAGTGCTGGTGCCCTTTCGGCTTCGAGGGCAAGAACTGCGAGCTG

GATGTGACTTGCAACATCAAGAACGGCAGGTGCGAGCAGTTCTGCAAGAACTCTGCCGACAACAAAGTCGTGTGCAGC

TGCACTGAGGGCTACAGACTGGCTGAGAACCAGAAGAGCTGTGAGCCTGCTGTGCCCTTCCCCTGCGGCAGAGTGTCT

GTGAGCCAGACCAGCAAGCTGACCAGAGCCGAAACCGTGTTCCCCGACGTGGACTATGTGAACAGCACTGAGGCTGAG

ACCATCCTGGACAACATCACTCAGTCTACCCAGTCTTTCAACGACTTCACCAGAGTGGTGGGGGGCGAGGACGCCAAG

CCTGGCCAGTTCCCCTGGCAGGTCGTGCTGAACGGCAAGGTGGACGCCTTCTGCGGGGGCAGCATCGTCAACGAGAAG

TGGATCGTGACTGCCGCCCACTGCGTGGAGACTGGGGTGAAGATCACTGTGGTGGCTGGGGAGCACAACATCGAGGAA

ACCGAGCACACTGAGCAGAAGAGGAACGTGATCAGGATTATCCCCCACCACAACTACAACGCCGCCATCAACAAGTAC

AACCACGACATCGCCCTGCTGGAGCTGGATGAACCCCTGGTGCTGAACAGCTACGTGACCCCTATCTGCATCGCCGAC

AAGGAGTACACTAACATCTTCCTGAAGTTCGGCAGCGGCTACGTGAGCGGCTGGGGCAGGGTGTTCCACAAGGGCAGG

AGCGCCCTGGTGCTGCAGTACCTGAGGGTGCCCCTGGTGGACAGGGCCACCTGCCTGCTGAGCACCAAGTTCACCATC

TACAACAACATGTTCTGCGCCGGCTTCCACGAGGGCGGCAGGGACAGCTGCCAGGGCGACAGCGGCGGCCCCCACGTG

ACCGAGGTGGAGGGCACCAGCTTCCTGACCGGCATCATCAGCTGGGGCGAGGAGTGCGCCATGAAGGGCAAGTACGGC

ATCTACACCAAGGTGAGCAGGTACGTGAACTGGATCAAGGAGAAGACCAAGCTGACCTAA

What is claimed is:

1. An isolated nucleic acid molecule comprising a nucleotide sequence having at least 90% sequence identity to the sequence set forth in SEQ ID NO: 1, wherein the nucleotide sequence encodes a factor IX (FIX) polypeptide comprising the amino acid sequence set forth in in SEQ ID NO:3, wherein:
   (i) the nucleotide sequence comprises a human codon adaptation index that is increased relative to the sequence set forth in SEQ ID NO:2;
   (ii) the nucleotide sequence contains a higher percentage of G/C nucleotides compared to the percentage of G/C nucleotides in the sequence set forth in SEQ ID NO:2;
   (iii) the nucleotide sequence does not contain the splice site having the sequence set forth in SEQ ID NO: 4 or 5;
   (iv) the nucleotide sequence contains fewer destabilizing elements comprising the sequence set forth in SEQ ID NO: 6 relative to the sequence set forth in SEQ ID NO:2;
   (v) the nucleotide sequence contains less repeat sequences relative to the sequence set forth in SEQ ID NO:2;
   (vi) the nucleotide sequence contains less antiviral motifs comprising the sequence set forth in SEQ ID NO: 11 relative to the sequence set forth in SEQ ID NO:2;
   (vii) the nucleotide sequence does not contain a poly-T sequence;
   (viii) the nucleotide sequence does not contain a poly-A sequence comprising a sequence set forth in SEQ ID NO: 9, SEQ ID NO: 10, SEQ ID NO:8, or any combination thereof; or
   (xi) any combination of (i) to (viii).

2. The isolated nucleic acid molecule of claim 1, wherein:
   (i) the human codon adaptation index is at least about 0.75;
   (ii) the percentage of G/C nucleotides is at least about 42%;
   (iii) the nucleotide sequence contains no destabilizing element;
   (iv) the repeat sequences in the isolated nucleic acid molecule include direct repeat, inverted repeat, or dyad repeat sequences;
   (v) the nucleotide sequence contains no antiviral motif comprising the sequence set forth in SEQ ID NO: 11; or
   (vi) any combination of (i) to (v).

3. The isolated nucleic acid molecule of claim 1, which further comprises a heterologous nucleotide sequence.

4. The isolated nucleic acid molecule of claim 3, wherein the heterologous nucleotide sequence encodes a heterologous amino acid sequence that is a half-life extender.

5. The isolated nucleic acid molecule of claim 3, wherein the heterologous nucleotide sequence encodes a heterologous amino acid sequence, wherein the heterologous amino acid sequence is an immunoglobulin constant region or a portion thereof, transferrin, albumin, XTEN, or a PAS sequence.

6. The isolated nucleic acid molecule of claim 5, wherein the heterologous amino acid sequence is an Fc region.

7. The isolated nucleic acid molecule of claim 4, wherein the heterologous amino acid sequence is linked to the N-terminus or the C-terminus of the amino acid sequence encoded by the nucleotide sequence or inserted between two amino acids in the amino acid sequence encoded by the nucleotide sequence.

8. The isolated nucleic acid molecule of claim 3, which encodes a monomer-dimer hybrid molecule comprising Factor IX.

9. The isolated nucleic acid molecule of claim 1, operably linked to at least one transcription control sequence.

10. A vector comprising the nucleic acid molecule of claim 1.

11. A host cell comprising the nucleic acid molecule of claim 1.

12. The host cell of claim 11, wherein the host cell is a Chinese hamster ovary (CHO) cell, a human embryonic kidney (HEK) 293 cell, a baby hamster kidney (BHK) 21 cell, a PER.C6 cell, a NS0 cell, or a CAP cell.

13. The isolated nucleic acid molecule of claim 1, wherein the nucleotide sequence has at least 95% sequence identity to the sequence sete forth in SEQ ID NO: 1.

14. The isolated nucleic acid molecule of claim 1, wherein the nucleotide sequence comprises the sequence set forth in SEQ ID NO: 1.

15. The isolated nucleic acid molecule of claim 1, wherein the nucleotide sequence comprises a sequence set forth in SEQ ID NO: 53.

16. The isolated nucleic acid molecule of claim 5, wherein the heterologous amino acid sequence is an XTEN sequence.

17. An isolated nucleic acid molecule comprising a nucleotide sequence having at least 95% sequence identity to the sequence set forth in SEQ ID NO: 53, wherein the nucleotide sequence encodes a factor IX (FIX) polypeptide comprising the amino acid sequence set forth in SEQ ID NO: 3.

18. The isolated nucleic acid molecule of claim 17, wherein the nucleotide sequence has at least 99% sequence identity to the sequence set forth in the SEQ ID NO: 53.

19. The isolated nucleic acid molecule of claim 1, wherein the nucleotide sequence has at least 99% sequence identity to the sequence set forth in SEQ ID NO: 1.

20. An isolated nucleic acid molecule comprising a nucleotide sequence having at least 90% sequence identity to the sequence set forth in SEQ ID NO: 1, wherein the nucleotide sequence encodes a factor IX (FIX) polypeptide comprising the amino acid sequence set forth in SEQ ID NO: 3.

21. The isolated nucleic acid molecule of claim 20, wherein the nucleotide sequence has at least 95% sequence identity to the sequence set forth in SEQ ID NO: 1.

22. The isolated nucleic acid molecule of claim 20, wherein the nucleotide sequence comprises the sequence set forth in SEQ ID NO: 1.

* * * * *